United States Patent [19]
Shiokawa et al.

[11] Patent Number: 6,022,967
[45] Date of Patent: Feb. 8, 2000

[54] HETEROCYCLIC COMPOUNDS

[75] Inventors: Kozo Shiokawa, Kanagawa-ken; Shinichi Tsuboi, Tokyo; Shinzo Kagabu, Tokyo; Koichi Moriya, Tokyo, all of Japan

[73] Assignee: Nihon Bayer Agrochem K.K., Tokyo, Japan

[21] Appl. No.: 09/012,620

[22] Filed: Jan. 23, 1998

Related U.S. Application Data

[62] Division of application No. 08/662,096, Jun. 12, 1996, Pat. No. 5,750,704, which is a division of application No. 08/404,849, Mar. 15, 1995, Pat. No. 5,580,889, which is a division of application No. 08/169,902, Dec. 20, 1993, Pat. No. 5,428,032, which is a division of application No. 08/067,642, May 25, 1993, Pat. No. 5,461,167, which is a division of application No. 07/832,174, Feb. 6, 1992, Pat. No. 5,298,507, which is a division of application No. 07/557,292, Jul. 24, 1990, Pat. No. 5,204,360, which is a division of application No. 07/347,836, May 4, 1989, Pat. No. 5,001,138, which is a division of application No. 07/068,991, Jul. 1, 1987, Pat. No. 4,845,106, which is a division of application No. 06/821,621, Jan. 21, 1986, Pat. No. 4,742,060.

[30] Foreign Application Priority Data

| Feb. 4, 1985 | [JP] | Japan | 60-18627 |
| Feb. 4, 1985 | [JP] | Japan | 60-18628 |
| Feb. 12, 1985 | [JP] | Japan | 60-23683 |
| May 21, 1985 | [JP] | Japan | 60-106853 |
| May 21, 1985 | [JP] | Japan | 60-106854 |
| Oct. 3, 1985 | [JP] | Japan | 60-219082 |

[51] Int. Cl.$^7$ ...... C07D 239/06; C07D 403/06; C07D 401/06
[52] U.S. Cl. ...... 544/298; 544/333; 546/272.7
[58] Field of Search ...... 544/298, 333; 546/272.7

[56] References Cited

U.S. PATENT DOCUMENTS

| 3,933,809 | 1/1976 | Powell | 544/53 |
| 3,962,233 | 6/1976 | Roman | 544/53 |
| 4,015,001 | 3/1977 | Powell | 544/54 |
| 4,531,002 | 7/1985 | Powell | 544/54 |
| 4,560,690 | 12/1985 | Reiter | 546/280 |
| 4,616,025 | 10/1986 | Exer et al. | 514/342 |
| 4,647,570 | 3/1987 | Shiokawa et al. | 514/341 |
| 4,650,805 | 3/1987 | Jaen et al. | 546/280 |
| 4,678,795 | 7/1987 | Shiokawa et al. | 514/341 |
| 4,772,620 | 9/1988 | Shiokawa et al. | 514/341 |
| 4,803,277 | 2/1989 | Shiokawa et al. | 514/332 |
| 4,882,344 | 11/1989 | Shiokawa et al. | 514/342 |
| 4,988,712 | 1/1991 | Shiokawa et al. | 514/340 |
| 5,298,507 | 3/1994 | Shiokawa et al. | 514/341 |

FOREIGN PATENT DOCUMENTS

| 2 824 690 | 12/1979 | European Pat. Off. |
| 0 029 742 | 6/1981 | European Pat. Off. |
| 0 060 730 | 9/1982 | European Pat. Off. |
| 0 092 158 | 10/1983 | European Pat. Off. |
| 3 409 801 | 9/1984 | European Pat. Off. |
| 0 163 855 | 12/1985 | European Pat. Off. |
| 2 514 402 | 10/1976 | Germany . |
| 2 732 660 | 2/1979 | Germany . |
| 196877 | of 1984 | Japan . |
| 60/718386 | 11/1985 | Japan . |
| 2 055 796 | 3/1981 | United Kingdom . |
| 2140412 | 11/1984 | United Kingdom . |

OTHER PUBLICATIONS

Beilstein, Syst.–Nr. 4192/H 17, p. 977 (1984).
March Advanced Organic Chemistry Reaction, 4–2, pp. 636–637 (1985).
α–Methyl Functionalization of Electro–Poor Heterocycles, Synthesis, Newkome, et al., pp. 676–679 (1984).
A. A. Amos et al., "The Acidity of Nitroguanidine and its Homologues", Can. J. Chem., vol. 39, pp. 1787–1796 (1961).

*Primary Examiner*—Mukund J. Shah
*Assistant Examiner*—Bruck Kifle
*Attorney, Agent, or Firm*—Sprung Kramer Schaefer & Briscoe

[57] ABSTRACT

Novel insecticides of the formula

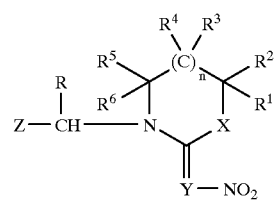

in which
n is 0 or 1,
X is S, O,

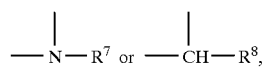

Y is N or

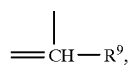

Z is a 5- or 6-membered nitrogen-containing heterocyclic ring, and
R to $R^9$ variously represent hydrogen or specified organic radicals.

3 Claims, No Drawings

HETEROCYCLIC COMPOUNDS

This is a division of application Ser. No. 08/662,096, filed on Jun. 12, 1996 now U.S Pat. No. 5,750,704, which is a divisional of application Ser. No. 08/404,849, filed on Mar. 15, 1995, now U.S. Pat. No. 5,580,889, which is a divisional of application Ser. No. 08/169,902, filed on Dec. 20, 1993, now U.S. Pat. No. 5,428,032, which is a divisional of application Ser. No. 08/067,642, filed on May 25, 1993, now U.S. Pat. No. 5,461,167, which is a divisional of application Ser. No. 07/832,174, filed on Feb. 6, 1992, now U.S. Pat. No. 5,298,507, which is a divisional of application Ser. No. 07/557,292, filed on Jul. 24, 1990, now U.S. Pat. No. 5,204,360, which is a divisional of application Ser. No. 07/347,836, filed on May 4, 1989, now U.S. Pat. No. 5,001,138, which is a divisional of application Ser. No. 07/068,991, filed on Jul. 1, 1987, now U.S. Pat. No. 4,845,106, which is a divisional of application Ser. No. 06/821,621, filed on Jan. 21, 1986, now U.S. Pat. No. 4,742,060.

The present invention relates to novel heterocyclic compounds, to processes for their preparation, to their use as insecticides.

It has already been disclosed that not only certain nitromethylene derivatives have insecticidal function, for instance, 1-benzyl-2-nitromethylene tetrahydropyrimidine (see DE-OS 2,514,402), but certain triazolidine derivatives have anti-tumor function against gastrointestinal tumor (see Japanese Laid-Open Patent Publication 196,877/1984).

Furthermore, 1-benzyl-2-nitroiminoimidazolidine has been described in Can. J. Chem., vol. 39, pages 1787–1796.

There have now been found novel heterocyclic compounds of the formula (I):

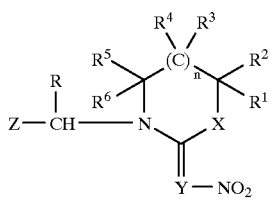

wherein
n represents 0 or 1,
$R^1$, $R^2$, $R^5$ and $R^6$ independently represent a hydrogen atom or an alkyl group, $R^3$ and $R^4$ independently represent a hydrogen atom, a hydroxy group or an alkyl group, where n represents 1, then $R^2$ may form a single bond, together with $R^5$,
X represents a sulfur atom, an oxygen atom,

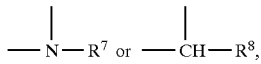

wherein
$R^7$ represents a hydrogen atom, a halogen atom, a hydroxy group, an alkoxy group, a benzyloxy group, an alkyl group which may be substituted by at least one substituent selected from the class consisting of alkoxy groups, alkylthio groups, a cyano group, halogen atoms, dialkylamino groups and trialkylsilyl, an alkenyl group which may be substituted by a halogen atom, an alkynyl group which may be substituted by a halogen atom, a phenyl group which may be substituted by an alkyl group and/or a halogen atom, a benzyl group which may be substituted by at least one substituent selected from the class consisting of a methyl group, a methoxy group, halogen atoms, halomethyl groups, halomethoxy groups and a nitro group, a formyl group, an alkenylcarbonyl group, an alkylcarbonyl group which may be substituted by at least one substituent selected from the class consisting of alkoxy groups, a phenoxy group, alkylthio groups, and halogen atoms, a benzoyl group which may be substituted by at least one substituent selected from the class consisting of halogen atoms, alkyl groups, halomethyl groups, alkoxy groups, haloalkoxy groups and a nitro group, a benzylcarbonyl group which may be substituted by an alkyl group and/or a halogen atom, an alkoxycarbonyl group which may be substituted by a halogen atom, an alkylthiocarbonyl group, a phenoxycarbonyl group which may be substituted by at least one substituent selected from the class consisting of methyl group, a methoxy group, halomethyl group, halomethoxy groups, halogen atoms and a nitro group, a phenylthiocarbonyl group which may be substituted by a halogen atom and/or an alkyl group, a benzyloxycarbonyl group, a monoalkyl- or dialkyl-aminocarbonyl group, a phenylaminocarbonyl group which may be substituted by at least one substituent selected from the class consisting of alkyl groups, haloalkyl groups and halogen atoms, a benzoylaminocarbonyl group which may be substituted by an alkyl group and/or a halogen atom, a phenylsulfonylaminocarbonyl group which may be substituted by an alkyl group and/or a halogen atom, a phenylthio group which may be substituted by an alkyl group and/or a halogen atom, an alkylsulfonyl group which may be substituted by a halogen atom, a phenylsulfonyl group which may be substituted by at least one substituent selected from the class consisting of alkyl groups, halogen atoms and a nitro group, an alkylcarbonylmethyl group, a phenacyl group which may be substituted by a halogen atom and/or an alkyl group, an organophosphono group, an organothionophosphono group, —CH$_2$W or —CO—W, wherein W represents a 5 to 6 membered heterocyclic group, containing at least one hetero atom selected from the class consisting of an oxygen atom, a sulfur atom and a nitrogen atom, which may be substituted by at least one substituent selected from the class consisting of halogen atoms, alkyl groups and haloalkyl groups, $R^8$ represents a hydrogen atom, an alkyl group, an aryl group or a benzyl group, Y represents a nitrogen atom or

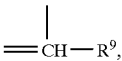

wherein
$R^9$ represents a hydrogen atom, a halogen atom, a hydroxy group, an alkoxy group, a benzyloxy group, an alkyl group which may be substituted by at least one substituent selected from the class consisting of halogen atoms, a hydroxy group, alkoxy groups, alkylthio groups, a cyano group, mono- or di-alkylamino groups, alkylcarbonyl groups, alkoxycarbonyl groups and phenoxycarbonyl groups, an alkenyl group which may be substituted by a halogen atom, an alkynyl group, a phenyl group which may be substituted by an alkyl group and/or a halogen atom, an alkylcarbonyl group which may be substituted by a halogen atom, an alkenylcarbonyl group, a benzoyl group which may be substituted by at least one substituent selected from the class consisting of halogen atoms, alkyl groups and alkoxy groups, an alkoxycarbonyl group which may be substituted by a halogen atom, an alkylthiocarbonyl group, a phenoxycarbonyl group which may be substituted by at least one substituent selected from the class consisting of halogen atoms, alkyl groups, alkoxy groups and a nitro group, a phenylthiocarbonyl group which may be substituted by an alkyl group and/or a halogen atom, a phenylthiocarbonyl group which may be substituted by an alkyl group and/or a halogen atom, a benzyloxycarbonyl group, a benzoylaminocarbonyl group which may be substituted by an alkyl group and/or a halogen atom, a phenylsulfonylaminocarbonyl group which may be substituted by an alkyl group and/or a halogen atom, an alkylsulfonylaminocarbonyl group, an alkylthio group, an alkylsulfonyl group which may be substituted by a halogen atom, a phenylthio group which may be substituted by an alkyl group and/or a halogen atom, a phenylsulfonyl group which may be substituted by an alkyl group and/or a halogen atom, in addition, $R^9$ may form a bis-form of the formula (I), via a methylene group, R represents a hydrogen atom or an alkyl group, and Z represents a 5 to 6 membered heterocyclic group containing at least one hetero atom selected from the class consisting of an oxygen atom, a sulfur atom and a nitrogen atom, which may be substituted by at least one substituent selected from the class consisting of halogen atoms, alkyl groups, haloalkyl groups, a nitro group, a cyano group, alkoxy groups, alkylthio groups, alkylsulfinyl groups, alkylsulfonyl groups, alkenyl groups, haloalkoxy group, haloalkylthio groups, haloalkenyl groups, acylamino groups, haloacylamino groups, alkoxycarbonyl groups, a thiocyanato group, alkynyl groups, an amino group, alkylamino groups, dialkylamino groups, a carboxy group, a hydroxy group, a mercapto group, cycloalkyl groups, an oxo group, a thioxo group, haloalkenylthio groups, alkoxyalkyl groups, alkoxycarbonylamino groups, a carbamoyl group, acyl groups, alkylaminocarbonyl groups, dialkylaminocarbonyl groups, a formyl group, aryl groups optionally substituted by a substituent selected from the class consisting of halogen atoms, alkyl groups, halogenoalkyl groups, alkoxy groups, a nitro group and a cyano group, aryloxy groups optionally substituted by the substituent as that shown for the above aryl groups, and aralkyl groups optionally substituted by the same substituent as that shown for the aryl groups, provided that where $R^1$, $R^2$, $R^3$, $R^4$, $R^5$ and $R^6$ represent hydrogen atoms simultaneously, X represents

and Y represents

then Z must not stand for the pyridyl group.

In the case of compounds according to the formula (I) having the following formula (Ia):

(Ia)

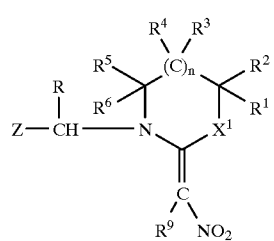

wherein
n, $R^1$, $R^2$, $R^3$, $R^4$, $R^5$, $R^6$, R, $R^9$ and Z have the same meanings as stated above,
$X^1$ represents a sulfur atom, a oxygen atom or the following group

$R^{10}$ means, in the definition of $R^7$, other groups than acyl groups including sulfonyl groups and phosphono groups,
the compounds of the formula (Ia) are obtained when
(a) the compounds of the formula (II)

(II)

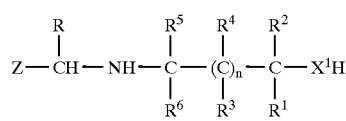

wherein
n, $R^1$, $R^2$, $R^3$, $R^4$, $R^5$, $R^6$, R, $X^1$ and Z have the same meanings as stated above,
are reacted with the compounds of the formula (III)

(III)

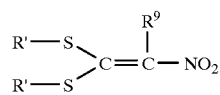

wherein
R' represents a lower alkyl or a benzyl group, or the two R's may form a ring, together with two sulfur atoms to which they are bonded and $R^9$ has the same meaning as stated above,
if appropriate, in the presence of inert solvents,
(b) the compounds of the above formula (II) are reacted with the compounds of the formula (IV)

(IV)

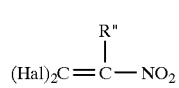

wherein
Hal represents a halogen atom and
R" represents a hydrogen atom, a halogen atom or a lower alkyl group,
if appropriate, in the presence of inert solvents and in the presence of acid acceptors, or
(c) the compounds of the above formula (II) are reacted with the compounds of the formula (V)

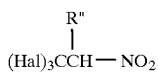 (V)

wherein
Hal and R" have the same meanings as stated above,
if appropriate, in the presence of inert solvents and in the presence of acid acceptors.

In the case of compounds according to the formula (I) having the following formula (Ib):

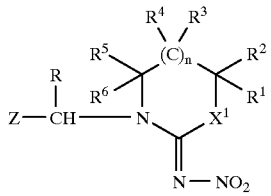 (Ib)

wherein
n, $R^1$, $R^2$, $R^3$, $R^4$, $R^5$, $R^6$, R, $X^1$ and Z have the same meanings as stated above,
the compounds of the formula (Ib) are obtained when
(d) the compounds of the aforesaid formula (II) are reacted with nitroguanidine of the following formula

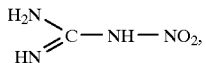

if appropriate, in the presence of inert solvents.
In the case of the formula (I) having the following formula (Ic)

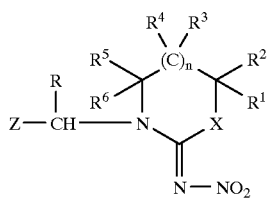 (Ic)

wherein
n, $R^1$, $R^2$, $R^3$, $R^4$, $R^5$, $R^6$, X, R and
Z have the same meanings as stated above, the compounds of the formula (Ic) are obtained
when
(e) the compounds of the formula (VI)

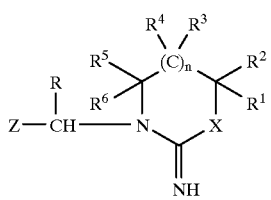 (VI)

wherein
n, $R^1$, $R^2$, $R^3$, $R^4$, $R^5$, $R^6$, X, R and

Z have the same meanings as stated above,
are reacted with fuming nitric acid, if appropriate, in the presence of inert solvent.

The compounds of the formula (I) are obtained when
(f) the compounds of the formula (VII)

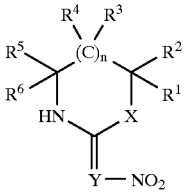 (VII)

wherein
n, $R^1$, $R^2$, $R^3$, $R^4$, $R^5$, $R^6$, X and Y have the same meanings as stated above,
are reacted with the compounds of the formula (VIII)

(VIII)

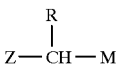

wherein
R and Z have the same meaning as stated above,
M represents a halogen atom or $-OSO_2T$, and
T represents a lower alkyl group, a phenyl group or a tolyl group,
if appropriate, in the presence of inert solvents and in the presence of acid acceptors.

The novel heterocyclic compounds exhibit powerful insecticidal properties.

Surprisingly, the heterocyclic compounds according to the invention exhibit a substantially greater and much more excellent insecticidal action than the closest known compounds from the aforementioned prior art.

In addition, the heterocyclic compounds according to the invention also exhibit a remarkable insecticidal action against harmful insects, in particular sucking insects typified by insects of Hemiptera such as aphids, plant hoppers and leaf hoppers, which have acquired resistance to organic phosphate and carbamate type-insecticides caused by long term use.

Among the novel heterocyclic compounds according to the invention, of the formula (I), preferred compounds are those in which
n represents 0 or 1,
$R^1$, $R^2$, $R^5$ and $R^6$ independently represent a hydrogen atom or an alkyl group having 1 to 4 carbon atoms, $R^3$ and $R^4$ independently represent a hydrogen atom, a hydroxy group or an alkyl group having 1 to 4 carbon atoms,
X represents a sulfur atom, an oxygen atom,

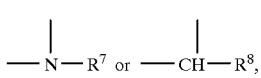

$R^7$ represents a hydrogen atom, a fluorine atom, a chlorine atom, a bromine atom, a hydroxy group, an alkoxy group having 1 to 4 carbon atoms, a benzyloxy group, an alkyl group having 1 to 4 carbon atoms which may be substituted by at least one member selected from the class consisting off alkoxy groups having 1 to 4 carbon atoms, alkylthio groups having 1 to 4 carbon atoms, a cyano group, a fluorine atom, a chlorine atom, a bromine atom, a dimethylamino group and trimethylsilyl, an alkenyl group having 2 to 3 carbon atoms which may be substituted by a chlorine atom, an alkynyl group having 2 to 3 carbon atoms, a benzyl group which may be substituted by at least one substituent selected from the class consisting of a methyl group, a methoxy group, a fluorine atom, a chlorine atom, a bromine atom and a nitro group, a formyl group, an alkenylcarbonyl group having an alkenyl part with 2 to 3 carbon atoms, an alkyl group having 1 to 5 carbon atoms which may be substituted by at least one substituent selected from the class consisting of a methoxy group, a phenoxy group, a fluorine atom, a chlorine atom and a bromine atom, a benzoyl group which may be substituted by at least one substituent selected from the class consisting of a fluorine atom, a chlorine atom, a bromine atom, a methyl group, a trifluoromethyl group, a methoxy group, a difluoromethoxy group, a trifluoromethoxy group and a nitro group, a benzylcarbonyl group which may be substituted by at least one substituent selected from the class consisting of a fluorine atom, a chlorine atom and a bromine atom, an alkoxycarbonyl group having an alkyl with 1 to 4 carbon atoms which may be substituted by a fluorine atom and/or a chlorine atom, an alkylthiocarbonyl group having an alkyl with 1 to 4 carbon atoms, a phenoxycarbonyl group which may be substituted by at least one substituent selected from the class consisting of a methyl group, a fluorine atom, a chlorine atom and a bromine atom, a phenylthiocarbonyl group which may be substituted by at least one substituent selected from the class consisting of a methyl group, a fluorine atom, a chlorine atom and a bromine atom, a benzyloxycarbonyl group, a dimethylaminocarbonyl group, a phenylaminocarbonyl group which may be substituted by at least one substituent selected from the class consisting of a methyl group, a fluorine atom, a chlorine atom, and a bromine atom, a benzoylaminocarbonyl group which may be substituted by at least one substituent selected from the class consisting of a methyl group, a fluorine atom, a chlorine atom and a bromine atom, a phenylsulfonylaminocarbonyl group which may be substituted by at least one substituent selected from the class consisting of a fluorine atom, a chlorine atom and a bromine atom, a phenylthio group, an alkylsulfonyl group which may be substituted by a fluorine atom and/or a chlorine atom, a phenylsulfonyl group which may be substituted by at least one substituent selected from the class consisting of a methyl group, a fluorine atom, a chlorine atom, a bromine atom and a nitro group, a methylcarbonylmethyl group, a phenacyl group which may be substituted by a fluorine atom and/or a chlorine atom, an organophosphono group, an organothionophosphono group, —$CH_2$—W or —CO—W, W represents a 5 to 6 membered hetercyclic group, containing one or two hetero atoms selected from the class consisting of an oxygen atom, a sulfur atom and a nitrogen atom, which may be substituted by at least one substituent selected from the class consisting of a fluorine atom, a chlorine atom, a bromine atom and alkyl groups having 1 to 4 carbon atoms, $R^8$ represents a hydrogen atom, an alkyl group having 1 to 4 carbon atoms, a phenyl group or a benzyl group, Y represents a nitrogen atom or

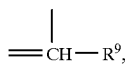

$R^9$ represents a hydrogen atom, a fluorine atom, a chlorine atom, a bromine atom, a hydroxy group, an alkoxy, group having 1 to 4 carbon atoms, a benzyloxy group, an alkyl group having 1 to 4 carbon atoms which may be substituted by at least one selected from the class consisting of a fluorine atom, a chlorine atom, a hydroxy group, an alkoxy group having 1 to 2 carbon atoms, alkylthio groups having 1 to 2 carbon atoms, a cyano group, a dimethylamino group, alkylcarbonyl groups having an alkyl with 1 to 2 carbon atoms and alkoxycarbonyl groups having an alkyl with 1 to 2 carbon atoms, an alkenyl group having 2 to 3 carbon atoms, a phenyl group, an alkylcarbonyl group having an alkyl with 1 to 4 carbon atoms which may be substituted by at least one selected from the class consisting of a methoxy group, a chlorine atom and a fluorine atom, an alkenylcarbonyl group having an alkenyl with 2 to 3 carbon atoms, a benzoyl group which may be substituted by at least one substituent selected from the class consisting of a fluorine atom, a chlorine atom, a bromine atom, a methoxy group and a methyl group, an alkoxycarbonyl group which may be substituted by a fluorine atom and/or a chlorine atom, an alkylthiocarbonyl group having an alkyl with 1 to 4 carbon atoms, a phenoxycarbonyl group which may be substituted by at least one substituent selected from the class consisting of a fluorine atom, a chlorine atom, a bromine atom, a methyl group, a methoxy group and a nitro group, a phenylthiocarbonyl group, a benzyloxycarbonyl group, a benzoylaminocarbonyl group which may be substituted by at least one substituent selected from the class consisting of a methyl group, a fluorine atom, a chlorine atom and a bromine atom, a phenylsulfonylaminocarbonyl group which may be substituted by at least one substituent selected from the class consisting of a methyl group, a fluorine atom, a chlorine atom and a bromine atom, an alkylsulfonylaminocarbonyl group having an alkyl with 1 to 4 carbon atoms, an alkylthio group having 1 to 4 carbon atoms, an alkylsulfonyl group which may be substituted by a fluorine atom and/or a chlorine atom, a phenylthio group which may be substituted by at least one substituent selected from the class consisting of a methyl group, a fluorine atom, a chlorine atom and a bromine atom, or a phenylsulfonyl group which may be substituted by at least one substituent selected from the class consisting of a methyl group, a fluorine atom, a chlorine atom and a bromine atom, in addition, $R^9$ may form a bis-form of the formula (I), via a methylene group, R represents a hydrogen atom or a methyl group, and Z represents a 5 to 6 membered heterocyclic group, containing one to three hetero atoms selected from the class consisting of an oxygen atom, a sulfur atom and a nitrogen atom, at least one of which is a nitrogen atom, which-may be substituted by at least one substituent selected from the class consisting of a fluorine atom, a chlorine atom, a bromine atom, alkyl groups having 1 to 4 carbon atoms which may be substituted by a fluorine atom and/or a chlorine atom, a nitro group, a cyano group, alkylsulfinyl groups having 1 to 4 carbon atoms, alkylsulfonyl groups having 1 to 4 carbon atoms, alkoxy groups having 1 to 4 carbon atoms which may be substituted by a fluorine atom and/or a chlorine atom, alkylthio groups having 1 to 4 carbon atoms which may be substituted by a fluorine atom and/or a chlorine atom, alkenyl groups having 2 to 3 carbon atoms which may be substituted by a chlorine atom, an acetamide group which may be substituted by a fluorine atom and/or a chlorine atom, alkoxycarbonyl groups having an alkyl with 1 to 4 carbon atoms, a thiocyanato group, alkynyl groups having 2 to 4 carbon atoms, an amino group, a methylamino group, a dimethylamino group, an acetyl group, a formyl group, a carboxy group, a hydroxy group, a mercapto group, cycloalkyl groups having 3 to 7 carbon atoms, an oxo group, a thioxo group, alkenylthio groups substituted by a fluorine atom, a chlorine atom and/or a bromine atom, alkoxyalkyl groups having 2 to 4 carbon atoms in total, alkylaminocarbonyl groups having an alkyl with 1 to 2 carbon atoms, dialkylaminocarbonyl groups having an alkyl with 1 to 2 carbon atoms, a phenyl group, a phenoxy group and a benzyl group, provided that where $R^1$, $R^2$, $R^3$, $R^4$, $R^5$ and $R^6$ represent hydrogen atoms simultaneously, X represents

and
Y represents

then Z must not stand for the pyridyl group.

Very particularly preferred heterocyclic compounds of the formula (I) are those in which n represents 0 or 1, $R^1$, $R^2$, $R^5$ and $R^6$ independently represent a hydrogen atom or a methyl group, $R^3$ and $R^4$ independently represent a hydrogen atom or a methyl group, X represents a sulfur atom, an oxygen atom or the following groups

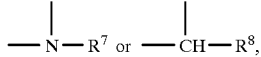

$R^7$ represents a hydrogen atom, an alkyl group which may be substituted by at least one substituent selected from the class consisting of a methoxy group, an ethoxy group, a methylthio group, an ethylthio group, a cyano group, a fluorine atom, a chlorine atom and a trimethylsilyl group, an allyl group which may be substituted by a chlorine atom, a propargyl group, a benzyl group which may be substituted by a methyl group and/or a chlorine atom, a formyl group, a vinylcarbonyl group, an alkylcarbonyl group having an alkyl with 1 to 3 carbon atoms which may be substituted by at least one substituent selected from the class consisting of methoxy group, a phenoxy group and a chlorine atom, a benzoyl group which may be substituted by at least one substituent selected from the class consisting of chlorine atom, a bromine atom, a methyl group, a trifluoromethyl group, a methoxy group and a nitro group, a benzylcarbonyl group which may be substituted by a chlorine atom, an alkoxycarbonyl group having an alkyl with 1 to 2 carbon atoms which may be substituted by a fluorine atom and/or a chlorine atom, an alkylthiocarbonyl group having an alkyl with 1 to 2 carbon atoms, a phenoxycarbonyl group which may be substituted by a methyl group and/or a chlorine atom, a phenylthiocarbonyl group which may be substituted by a chlorine atom, a benzyloxycarbonyl group, a dimethylaminocarbonyl group, a phenylaminocarbonyl group, a benzoylaminocarbonyl group, a phenylsulfonylaminocarbonyl group which may be substituted by a methyl group and/or a chlorine atom, a phenylthio group, a methylsulphonyl group which may be substituted by a chlorine atom, a phenylsulphonyl group which may be substituted by a methyl group, a methylcarbonylmethyl group, a phenacyl group which may be substituted by a chlorine atom, O,O-diethylthionophosphono group, O-ethyl-S-n-propylthiolophosphono group, —CH$_2$—W or —CO—W wherein W represents a 5 to 6 membered heterocyclic group, containing one or two hetero atoms selected from the class consisting of an oxygen atom, a sulfur atom and a nitrogen atom, which may be substituted by a fluorine atom, a chlorine atom, a bromine atom and a methyl group, $R^8$ represents a hydrogen atom, a methyl group, a phenyl group or a benzyl group, Y represents a nitrogen atom or

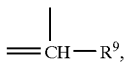

$R^9$ represents a hydrogen atom, a chlorine atom, a bromine atom, a hydroxy group, a methoxy group, a benzyloxy group, an alkyl group which may be substituted by at least one substituent selected from the class consisting of a fluorine atom, a chlorine atom, a hydroxy group, a methoxy group, a cyano group, a dimethylamino group, an acetyl group and a methoxycarbonyl group, an allyl group, a phenyl group, an acetyl group which may be substituted by a chlorine atom, a vinylcarbonyl group, an allylcarbonyl group, a benzoyl group, an alkoxycarbonyl group having an alkyl with 1 to 2 carbon atoms which may be substituted by a fluorine atom, n-butylthiocarbonyl group, a phenoxycarbonyl group which may be substituted by a chlorine atom and/or a methyl group, a phenylthiocarbonyl group, a benzyloxycarbonyl group, a benzoylaminocarbonyl group which may be substituted by a chlorine atom, a phenylsulfonylaminocarbonyl group which may be substituted by a methyl group, a methylsulfonylaminocarbonyl group, a propylthio group, a methylsulphonyl group which may be substituted by a fluorine atom and/or a chlorine atom, a phenylthio group which may be substituted by a chlorine atom, or a phenylsulphonyl group, in addition, $R^9$ may form a bis-form of the formula (I), via a methylene group, R represents a hydrogen atom or a methyl group, and Z represents a 5 to 6 membered heterocyclic group, containing one to three hetero atoms selected from the class consisting of an oxygen atom, a sulfur atom and a nitrogen atom, at least one of which is a nitrogen atom, which may be substituted by at least one substituent selected from the class consisting of a fluorine atom, chlorine atom, a brine atom, a methyl group, fluoroalkyl groups having 1 to 2 carbon atoms, a methoxy group, a methylthio group, a methylsulphinyl group, a methylsulphonyl group, a nitro group, a cyano group, a trifluoromethoxy group, a trifluoromethylthio group, an allyl group, an acetamide group, a methoxycarbonyl group, an acetyl group, a formyl group and a carboxyl group, provided that where $R^1$, $R^2$, $R^3$, $R^4$, $R^5$ and $R^6$ represent hydrogen atoms simultaneously, X represents

and

Y represents

then
Z must not stand for the pyridyl group.
Specifically, the following compounds may be mentioned:
3-(2-chloro-5-pyridylmethyl)-2-(nitromethylene) tetrahydro-2H-1,3-thiazine,
3-(2-chloro-5-pyridylmethyl)-2-(nitromethylene) thiazolidine,
3-(2-fluoro-5-pyridylmethyl)-2-(nitromethylene) tetrahydro-2H-1,3-thiazine,
3-(2-fluoro-5-pyridylmethyl)-2-(nitromethylene) thiazolidine,
3-(2-bromo-5-pyridylmethyl)-2-(nitromethylene) tetrahydro-2H-1,3-thiazine,
3-(2-bromo-5-pyridylmethyl)-2-(nitromethylene) thiazolidine,
3-(2-methyl-5-pyridylmethyl)-2-(nitromethylene) thiazolidine,
3-(2-methyl-5-pyridylmethyl)-2-(nitromethylene) tetrahydro-2H-1,3-thiazine,
3-(2-ethyl-5-pyridylmethyl)-2-(nitromethylene) thiazolidine,
3-(2-trifluoromethyl-5-pyridylmethyl)-2-(nitromethylene) tetrahydro-2H-1,3-thiazine,
3-(3-pyridylmethyl)-2-(nitromethylene) thiazolidine,
3-(3-pyridylmethyl)-2-(nitromethylene) tetrahydro-2H-1,3-thiazine,
3-(2-trifluoromethyl-5-pyridylmethyl)-2-(nitromethylene) thiazolidine,
1-(5-pyrazolylmethyl)-2-(nitromethylene) imidazolidine,
1-(5-chloro-1-methyl-3-pyrazolylmethyl)-2-(nitromethylene) imidazolidine,
1-(1-methyl-4-pyrazolylmethyl)-2-(nitromethylene)-tetrahydropyrimidine,
1-(1-methyl-4-pyrazolylmethyl)-2-(nitromethylene)-imidazolidine,
1-(3-trifluoromethyl-5-isoxazolylmethyl)-2-(nitromethylene) tetrahydropyrimidine,
1-(3-methyl-5-isoxazolylmethyl)-2-(nitromethylene)-imidazolidine,
1-(3-methyl-5-isoxazolylmethyl)-2-(nitromethylene)-tetrahydropyrimidine,
(1-(5-isoxazolylmethyl)-2-(nitromethylene) imidazolidine,
1-(2-methyl-5-thiazolylmethyl)-2-nitromethylene)-imidazolidine,
1-(2-chloro-5-thiazolylmethyl)-2-(nitromethylene)-tetrahydropyrimidine,
1-(2-trifluoromethyl-5-thiazolylmethyl)-2-(nitromethylene) imidazolidine,
1-(1,2,5-thiadiazol-3-ylmethyl)-2-(nitromethylene)-tetrahydropyrimidine,
1-(1,2,3-thiadiazol-5-ylmethyl)-2-(nitromethylene)-tetrahydropyrimidine,
1-(2-methyl-5-thiazolylmethyl)-2-(nitromethylene)-tetrahydropyrimidine,
1-(2-chloro-5-thiazolylmethyl)-2-(nitromethylene)-imidazolidine,
1-(1,2,5-thiadiazol-3-ylmethyl)-2-(nitromethylene)-imidazolidine,
1-(5-thiazolylmethyl)-2-(nitromethylene) tetrahydropyrimidine,
1-(5-pyrimidinylmethyl)-2-(nitromethylene)imidazolidine,
1-(2-methyl-5-pyrimidinylmethyl)-2-(nitromethylene)-imidazolidine,
1-(2-pyrazinylmethyl)-2-(nitromethylene)imidazolidine,
1-(2-methyl-5-pyrazinylmethyl)-2-(nitromethylene)-imidazolidine,
1-(2-chloro-5-pyrimidinylmethyl)-2-(nitromethylene)-tetrahydropyrimidine,
1-(2-chloro-5-pyrimidinylmethyl)-2-(nitromethylene)-imidazolidine,
1-(2-fluoro-5-pyrimidinylmethyl)-2-(nitromethylene)-imidazolidine,
1-(2-trifluoromethyl-5-pyrimidinylmethyl)-2-(nitromethylene)imidazolidine,
1-(2-chloro-5-pyrazinylmethyl)-2-(nitromethylene)-imidazolidine,
1-[1-(2-fluoro-5-pyrimidinyl)ethyl]-2-(nitromethylene)-imidazolidine,
1-(2-chloro-5-pyridylmethyl)-2-(nitroimino) tetrahydropyrimidine,
1-(2-chloro-5-pyridylmethyl)-2-(nitroimino)imidazolidine,
1-(2-trifluoromethyl-5-pyridylmethyl)-2-(nitroimino)-tetrahydropyrimidine,
1-(2-trifluoromethyl-5-pyridylmethyl)-2-(nitroimino)-imidazolidine,
1-(2-fluoro-5-pyridylmethyl)-2-(nitroimino) imidazolidine,
1-(2-bromo-5-pyridylmethyl)-2-(nitroimino)imidazolidine,
1-(2-methyl-5-pyridylmethyl)-2-(nitroimino)imidazolidine,
1-(2-methoxy-5-pyridylmethyl)-2-(nitroimino) imidazolidine,
1-(2-chloro-5-pyridylmethyl)-2-(nitromethylene)-pyrolidine,
1-(2-chloro-5-thiazolylmethyl)-2-(nitroimino) tetrahydropyrimidine,
1-(2-chloro-5-pyrimidinylmethyl)-2-(nitroimino)-imidazolidine,
1-(2-chloro-5-pyridylmethyl)-4-methyl-2-(nitromethylene) imidazolidine,
1-(2-chloro-5-pyridylmethyl)-3-(3-pyridylmethyl)-2-(nitromethylene) imidazolidine,
1-(2-chloro-5-pyridylmethyl)-2-(bromonitromethylene) imidazolidine,
1-(2-chloro-5-pyridylmethyl)-2-(1-nitro-2-oxopentylidene) imidazolidine,
ethyl nitro[3-(2-chloro-5-pyridylmethyl) thiazolidin-2-ylidene]acetate,
1-acetyl-3-(2-chloro-5-pyridylmethyl)-2-(nitroimino) imidazolidine, and
N-phenylsulfonyl-nitro[(1-(2-chloro-5-pyridylmethyl) imidazolidin-2-ylidene]acetamide.

If, in the process (a), for example, N-(1-methyl-4-pyrazolylmethyl) trimethylene diamine and 1-nitro-2,2-bis (methylthio) ethylene are used as starting materials, the course of the reaction can be represented by the following equation:

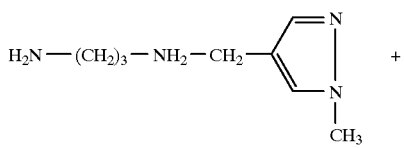

-continued

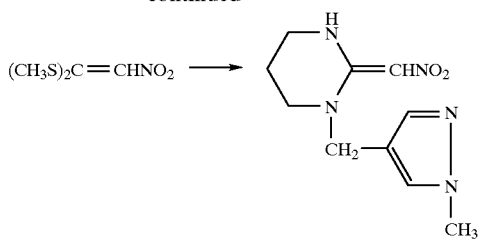

If, in the process (b), for example, 2-(2-methyl-5-pyrazinylmethylamino) ethanethiol and 2,2-dichloronitroethylene are used as starting materials, the course of the reaction can be represented by the following equation:

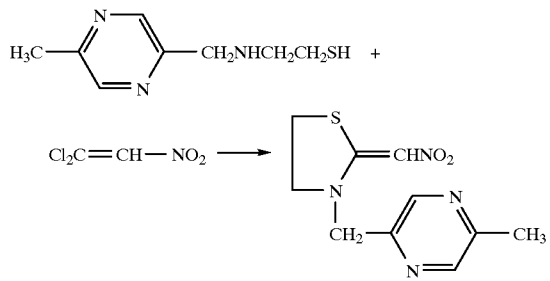

If, in the process (c), for example, 2-(2-chloro-5-thiazolylmethylamino)ethanethiol and 1,2,2,2-tetrachloro-1-nitroethane are used as starting materials, the course of the reaction can be represented by the following equation:

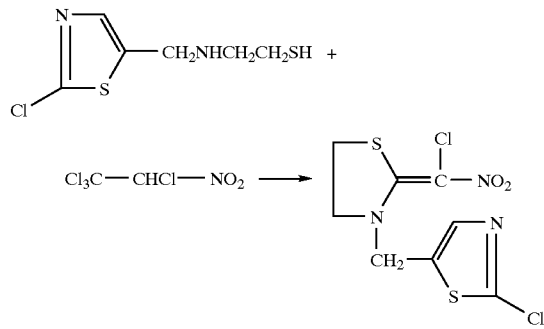

If, in the process (d), for example, N-(2-chloro-5-pyridylmethyl)trimethylenediamine and nitroguanidine are used as starting materials, the course of the reaction can be represented by the following equation:

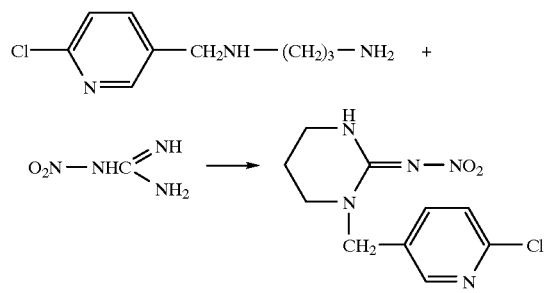

If, in the process (e), for example, 1-(2-chloro-5-pyridylmethyl)-2-iminoimidazolidine and fuming nitric acid are used as starting materials, the course of the reaction can be represented by the following equation:

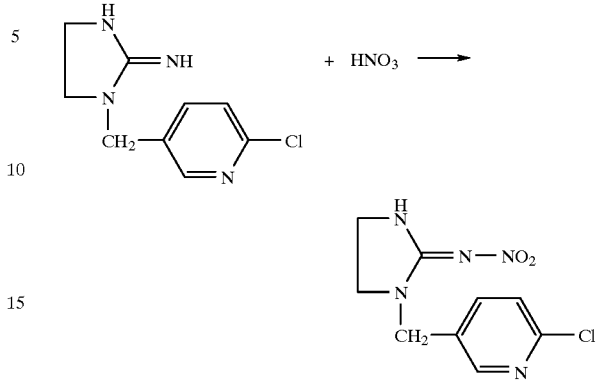

If, in the process (f), for example, 2-nitromethylenethiazolidine and 2-chloro-5-pyridylmethylchloride are used as starting materials, the course of the reaction can be represented by the following equation:

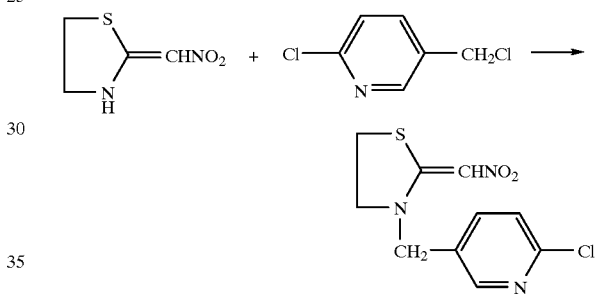

The formula (II) provides a general definition of the compounds required as a staring material in the process (a), based on aforesaid each definition of n, $R^1$, $R^2$, $R^3$, $R^4$, $R^5$, $R^6$, R, Z and $X^1$.

In the formula (II), n, $R^1$, $R^2$, $R^3$, $R^4$, $R^6$, R, Z and $X^1$ preferably have the meanings already given above.

The compounds of the formula (II) usable according to the invention include both known and novel ones.

The known examples have already been described in, for instance, Japanese Patent Application Nos. 26,020/1984, 72,966/1954 and 132,943/1984 Z. Anorg. Allgem. Chem., Vol. 312, pages 282–286, Khim. Geterotsikl. Soedin., 1974, No. 1, pages 122–123, Metody Poluch. Khim. Reactivon Prep., No. 17, pages 172–173, Issled. Obl. Geterotsikl. Soedin., 1971, pages 39–44, U.S. Pat. No. 4,018,931, Arch. Pharm., 1982, Vol. 315, pages 212–221, Metody Poluch. Khim. Reactivon Prep., 1967, pages 133–134, and Zh. Obshch Khim., Vol. 33, pages 1130–1135.

As examples, there may be mentioned the following:
N-(2-chloro-5-pyridylmethyl)2-aminoethanethiol,
N-(2-chloro-5-pyridylmethyl)3-aminopropanethiol,
N-(2-bromo-5-pyridylmethyl)2-aminoethanethiol,
N-(2-bromo-5-pyridylmethyl)3-aminopropanethiol,
N-(2-fluoro-5-pyridylmethyl)2-aminoethanethiol,
N-(2-fluoro-5-pyridylmethyl)3-aminopropanethiol,
N-[-(2-chloro-5-pyridyl)ethyl]2-aminoethanethiol,
N-(2,3-dichloro-5-pyridylmethyl)2-aminoethanethiol,
N-(3-chloro-2-fluoro-5-pyridylmethyl)2-aminoethanethiol,
N-(2-chloro-4-pyridylmethyl)2-aminoethanethiol,
N-(3-chloro-2-pyridylmethyl)2-aminoethanethiol, N-(5-chloro-2-pyridylmethyl)3-aminopropanethiol,
N-(3,5-dichloro-2-pyridylmethyl)2-aminoethanethiol,
N-(5-fluoro-2-pyridylmethyl)3-aminopropanethiol,
N-(6-bromo-2-pyridylmethyl)2-aminoethanethiol,
N-(2-chloro-3-pyridylmethyl)3-aminopropanethiol,
N-(5-chloro-3-pyridylmethyl)3-aminopropanethiol,
N-(5-bromo-3-pyridylmethyl)2-aminoethanethiol,
N-(5-fluoro-3-pyridylmethyl)2-aminoethanethiol,
N-[1-(2-fluoro-5-pyridyl)ethyl]-2-aminoethanethiol,
N-(2,4-dichloro-5-pyridylmethyl) 3-aminopropanethiol,
N-(2,4-dibromo-5-pyridylmethyl) 2-aminoethanethiol,
N-(2,6-difluoro-4-pyridylmethyl) 2-aminoethanethiol,
N-(2-fluoro-4-pyridylmethyl) 3-aminopropanethiol,
N-(2,6-dibromo-4-pyridylmethyl) 2-aminoethanethiol,
N-(3-bromo-2-fluoro-5-pyridylmethyl) 2-aminoethanethiol,
N-(2-chloro-3-fluoro-5-pyridylmethyl) 2-aminoethanethiol,
N-[1-(2-chloro-5-pyridyl) propyl]2-aminoethanethiol,
N-(3-pyridylmethyl) 2-aminoethanethiol,
N-(3-pyridylmethyl) 3-aminopropanethiol,
N-(4-pyridylmethyl) 2-aminoethanethiol,
N-(4-pyridylmethyl) 3-aminopropanethiol,
N-(2-methyl-5-pyridylmethyl) 2-aminoethanethiol,
N-(2-methyl-5-pyridylmethyl) 3-aminopropanethiol,
N-(2-ethyl-5-pyridylmethyl) 2-aminoethanethiol,
N-(2-allyl-5-pyridylmethyl) 2-aminoethanethiol,
N-(2-propargyl-5-pyridylmethyl) 2-aminoethanethiol,
N-(2-methoxy-5-pyridylmethyl) 3-aminopropanethiol,
N-(2-methylthio-5-pyridylmethyl) 2-aminopropanethiol,
N-(2-methylsulfonyl-5-pyridylmethyl) 2-aminoethanethiol,
N-(2-chloro-3-methyl-5-pyridylmethyl) 2-aminoethanethiol,
N-[1-(3-pyridyl) ethyl]3-aminopropanethiol,
N-(2-trifluoromethyl-5-pyridylmethyl) 2-aminoethanethiol,
N-(2-trifluoromethyl-3-pyridylmethyl) 3-aminopropanethiol,
N-(2-nitro-5-pyridylmethyl) 2-aminoethanethiol,
N-(2-nitro-5-pyridylmethyl) 3-aminopropanethiol,
N-(2-cyano-5-pyridylmethyl) 2-aminoethanethiol,
N-(2-cyano-5-pyridylmethyl) 3-aminopropanethiol,
N-(2-methylsulfinyl-5-pyridylmethyl) 2-aminoethanethiol,
N-(2-phenyl-5-pyridylmethyl) 2-aminoethanethiol,
N-(2-benzyl-5-pyridylmethyl) 2-aminoethanethiol,
N-(2-phenoxy-5-pyridylmethyl) 3-aminopropanethiol,
N-(2-trichloromethyl-5-pyridylmethyl) 2-aminoethanethiol,
N-[2-(2-ethoxyethyl)-5-pyridylmethyl]3-aminopropanethiol,
N-(2-methoxymethyl-5-pyridylmethyl) 2-aminoethanethiol,
N-(2-difluoromethoxy-5-pyridylmethyl) 2-aminoethanethiol,
N-(2-trifluoromethoxy-5-pyridylmethyl)-2-aminoethanethiol,
N-[2-(2,2,2-trifluoroethoxy)-5-pyridylmethyl]2-aminoethanethiol,
N-(2-chlorodifluoromethylthio-5-pyridylmethyl) 3-aminopropanethiol,
N-(2-trifluoromethylthio-5-pyridylmethyl) 2-aminoethanethiol,
N-(2-difluoromethyl-5-pyridylmethyl) 2-aminoethanethiol,
N-(2-trifluoromethylsulfonyl-5-pyridylmethyl) 2-aminoethanethiol,
N-(2-trifluoromethylsulfinyl-5-pyridylmethyl) 2-aminoethanethiol,
N-[2-(2,2-dichlorovinyl)-5pyridylmethyl) 2-aminoethanethiol,
N-(4-pyrimidinylmethyl) ethylenediamine,
N-(2-methyl-4-pyrimidinylmethyl) ethylenediamine,
N-(2-methyl-6-oxo-1H,6H-dihydropyrimidin-4-ylmethyl) trimethylenediamine,
N-(5-pyrimidinylmethyl) ethylenediamine,
N-(2-methyl-5-pyrimidinylmethyl) ethylenediamine,
N-(2-dimethylamino-5-pyrimidinylmethyl) ethylenediamine,
N-(2-dimethylamino-5-pyrimidinylmethyl) trimethylenediamine,
N-'2,4,6-trichloro-5-pyrimidinylmethyl) ethylenediamine,
N-(pyrazinylmethyl)ethylenediamine,
N-[1-(pyrazinyl)ethyl]ethylenediamine,
N-(2-methyl-5-pyrazinylmethyl)ethylenediamine,
N-(3-pyrazinylmethyl)ethylenediamine,
N-(2-chloro-4-pyrimidinylmethyl)ethylenediamine,
N-(4-chloro-6-pyrimidinylmethyl)ethylenediamine,
N-4-methyl-6-pyrimidinylmethyl)trimethylenediamine,
N-(2-fluoro-5-pyrimidinylmethyl)ethylenediamine,
N-[1-(2-fluoro-5-pyrimidinyl)ethyl]ethylenediamine,
N-(2-chloro-5-pyrimidinylmethyl)ethylenediamine,
N-(2-chloro-5-pyrimidinylmethyl)trimethylenediamine,
N-(2-isopropyl-5-pyrimidinylmethyl)ethylenediamine,
N-(2-chlorodifluoromethyl-5-pyrimidinylmethyl) ethylenediamine,
N-(2-trifluoromethyl-5-pyrimidinylmethyl) ethylenediamine,
N-(2-bromodifluoromethyl-5-pyrimidinylmethyl) ethylenediamine,
N-(2-methoxy-5-pyrimidinylmethyl)ethylenediamine,
N-(2-difluoromethoxy-5-pyrimidinylmethyl ethylenediamine,
N-(2-trifluoromethoxy-5-pyrimidinylmethyl) ethylenediamine,
N-[(2-(2,2,2-trifluoroethoxy)-5-pyrimidinylmethyl] trimethylenediamine,
N-(2-methylthio-5-pyrimidinylmethyl)ethylenediamine,
N-(2-ethylthio-5-pyrimidinylmethyl)ethylenediamine,
N-(2-difluoroethylthio-5-pyrimidinylmethyl) ethylenediamine,
N-(2-trifluoromethylthio-5-pyrimidinylmethyl) ethylenediamine,
N-[2-(2,2,2-trifluoroethylthio)-5-pyrimidinylmethyl]-ethylenediamine,
N-(2-nitro-5-pyrazinylmethyl) ethylenediamine,
N-(2-cyano-5-pyrazinylmethyl)trimethylenediamine,
N-(2-chloro-5-pyrazinylmethyl) ethylenediamine,
N-(2-trifluoromethyl-5-pyrazinylmethyl)ethylenediamine,
N-(3-fluoro-6-pyridazinylmethyl)ethylenediamine,
N-(3-methyl-6-pyridazinylmethyl)trimethylenediamine,
N-(4-pyridazinylmethyl)ethylenediamine,
N-(3-chloro-6-pyridazinylmethyl)ethylenediamine,
N-(4-pyridazinylmethyl)trimethylenediamine,
N-(3-trifluoromethyl-6-pyridazinylmethyl)ethylenediamine,
N-(1,3,5-triazin-2-ylmethyl)ethylenediamine,
N-(3-chloro-1,2,4-triazin-6-ylmethyl)ethylenediamine,
N-(3,5-dichloro-1,2,4-triazin-6-ylmethyl)ethylenediamine,
N-(3-chloro-1,2,4,5-tetrazin-6-ylmethyl)ethylenediamine,
N-(3-furylmethyl)-ethylene (or -trimethylene)diamine,
N-(furfuryl)-ethylene (or -trimethylene)diamine,
N-(5-methylfurfuryl)-ethylene (or -trimethylene)diamine,
N-(2-thienylmethyl)-ethylene (or -trimethylene)diamine,
N-(4-imidazolylmethyl)-ethylene (or -trimethylene) diamine,
N-(4-methyl-5-imidazolylmethyl)-ethylene (or -trimethylene)diamine,
N-(tetrahydrofurfuryl)-ethylene (or -trimethylene)-diamine,
N-(5-methyltetrahydrofurfuryl)ethylene (or -trimethylene) diamine,
N-(3-thienylmethyl)-ethylene (or -trimethylene)diamine,
N-(2-pyrrolylmethyl)-ethylene (or -trimethylene)diamine, N-(1-methyl-2-pyrrolylmethyl)-ethylene (or -trimethylene) diamine,
N-(5-methyl-2-thienylmethyl)-ethylene (or -trimethylene) diamine,
N-(5-bromo-2-thienylmethyl)-ethylene (or -trimethylene) diamine,
N-(5-cyanofurfuryl)-ethylene (or -trimethylene)diamine,
N-(5-trifluoromethylthio-2-thienylmethyl)-ethylene-(or -trimethylene)diamine,
N-[1-(2-thienyl)ethyl]-ethylene (or -trimethylene)diamine,
N-(5-methyl-3-isoxazolylmethyl)-ethylene (or -trimethylene)diamine,
N-(5-isoxazolylmethyl)-ethylene (or -trimethylene)-diamine,
N-(4-isoxazolylmethyl)-ethylene (or -trimethylene)-diamine,
N-(3-methyl-5-isoxazolylmethyl)-ethylene (or -trimethylene)diamine,
N-(3-methyl-5-isoxazolylmethyl)-ethylene (or -trimethylene)diamine,
N-(3-trifluoromethyl-5-isoxazolylmethyl)-ethylene-(or -trimethylene)diamine,
N-(3-chloro-5-isoxazolylmethyl)-ethylene (or -trimethylene)diamine,
N-(5-isothiazolylmethyl)-ethylene (or -trimethylene)-diamine,
N-(5-pyrazolylmethyl)-ethylene (or -trimethylene)-diamine,
N-(4-pyrazolylmethyl)-ethylene (or -trimethylene)-diamine,
N-(1-methyl-4-pyrazolylmethyl)-ethylene (or -trimethylene)diamine,
N-[1-(1-methyl-4-pyrazolyl)ethyl]-ethylene (or -trimethylene)diamine,
N-(1-ethyl-4-pyrazolylmethyl)-ethylene (or -trimethylene) diamine,
N-(1-isopropyl-4-pyrazolylmethyl)-ethylene (or -trimethylene)diamine,
N-(1-allyl-4-pyrazolylmethyl)-ethylene (or -trimethylene) diamine,
N-(1-tert-butyl-4-pyrazolylmethyl)-ethylene (or -trimethylene)diamine,
N-[1-(2,2,2-trifluoroethyl)-5-pyrazolylmethyl]-ethylene (or -trimethylene)diamine,
N-(3-methyl-5-pyrazolylmethyl)-ethylene (or -trimethylene)diamine,
N-(3-chloro-2-methyl-5-pyrazolylmethyl)-ethylene (or -trimethylene) diamine,
N-(2,3,5-trimethyl-4-pyrazolylmethyl)-ethylene (or -trimethylene)diamine,
N-(5-oxazolylmethyl)-ethylene (or -trimethylene)-diamine,
N-(4-methyl-5-oxazolylmethyl)-ethylene (or -trimethylene) diamine,
N-(4-thiazolylmethyl)-ethylene (or -trimethylene)-diamine,
N-(5-thiazolylmethyl)-ethylene (or -trimethylene)-diamine,
N-(2-methyl-5-thiazolylmethyl)-ethylene (or -trimethylene)-diamine,
N-(2-chloro-4-thiazolylmethyl)-ethylene (or -trimethylene)-diamine,
N-(2-chloro-5-thiazolylmethyl)-ethylene (or -trimethylene) diamine,
N-(2-trifluoromethyl-5-thiazolylmethyl)-ethylene (or -trimethylene)diamine,
N-(2-bromo-5-thiazolylmethyl)-ethylene (or -trimethylene) diamine,
N-(2,4-dichloro-5-thiazolylmethyl)-ethylene (or trimethylene)diamine,
N-(4-imidazolylmethyl)-ethylene (or -trimethylene)-diamine,
N-(1-methyl-2-imidazolylmethyl)-ethylene (or -trimethylene)diamine,
N-(1,2,4-triazol-5-ylmethyl)-ethylene (or -trimethylene) diamine,
N-(1-methyl-1,2,4-triazol-3-ylmethyl)-ethylene (or -trimethylene)diamine,
N-(1,2,5-thiadiazol-4-ylmethyl)-ethylene (or -trimethylene) diamine,
N-(1,2,3-thiadiazol-5-ylmethyl)-ethylene (or -trimethylene) diamine,
N-(3-methyl-1,2,4-oxadiazol-5-ylmethyl)-ethylene (or -trimethylene)diamine,
N-(1,3-dioxolan-2-ylmethyl)-ethylene (or -trimethylene) diamine,
N-(2,2-dimethyl-1,3-dioxolan-4-ylmethyl)-ethylene-(or -trimethylene)diamine,
N-(2-methyl-2-oxazolin-5-ylmethyl)-ethylene (or -trimethylene)diamine,
N-(2-trifluoromethyl-2-oxazolin-5-ylmethyl)-ethylene (or -trimethylene)diamine,
N-(3-pyrrolylmethyl)-ethylene (or -trimethylene)diamine,
N-(1-ethyl-2-pyrrolylmethyl)-ethylene (or -trimethylene) diamine,
N-(1-methyl-3-pyrrolylmethyl)-ethylene (or -trimethylene) diamine,
N-(5-methyl-3-thienyl)-ethylene (or -trimethylene)-diamine,
N-(1-ethyl-2-pyrrolylmethyl)-ethylene (or -trimethylene) diamine,
N-(1-methyl-3-pyrrolylmethyl)-ethylene (or -trimethylene) diamine,
N-(5-methyl-3-thienyl)-ethylene (or -trimethylene)-diamine,
N-(5-methyl-3-pyrrolylmethyl)-ethylene (or -trimethylene) diamine,
N-(1,5-dimethyl-3-pyrrolylmethyl)-ethylene (or -trimethylene)diamine,
N-(2,5-dimethyl-3-furylmethyl)-ethylene (or -trimethylene) diamine,
N-(2,5-dimethyl-3-thienylmethyl)-ethylene (or -trimethylene)diamine,
N-(5-fluoro-3-furylmethyl)-ethylene (or -trimethylene) diamine,
N-(4-chlorofurfuryl)-ethylene (or -trimethylene)diamine,
N-(5-chlorofurfuryl)-ethylene (or -trimethylene)-diamine,
N-(5-chloro-3-furylmethyl)-ethylene (or -trimethylene) diamine,
N-(5-chloro-3-thienylmethyl)-ethylene (or -trimethylene) diamine,
N-(5-chloro-1-methyl-3-pyrrolylmethyl)-ethylene (or -trimethylene)diamine,
N-(5-bromo-3-furylmethyl)-ethylene (or -trimethylene)-diamine,
N-(5-nitrofufuryl)-ethylene (or -trimethylene) diamine,
N-(4-nitro-2-thienylmethyl)-ethylene (or -trimethylene) diamine,
N-(5-nitro-2-thienylmethyl)-ethylene (or -trimethylene) diamine,
N-(1-methyl-5-nitro-3-pyrrolylmethyl)-ethylene (or -trimethylene) diamine,
N-(5-cyano-3-furylmethyl)-ethylene (or -trimethylene)-diamine,
N-(5-cyano-3-thienylmethyl)-ethylene (or -trimethylene) diamine,
N-(5-cyano-1-methyl-3-pyrrolylmethyl)-ethylene (or -trimethylene)diamine,
N-(5-trifluoromethylfurfuryl)-ethylene (or -trimethylene) diamine, N-(5-difluoromethylfurfuryl)-ethylene (or -trimethylene) diamine,
N-(5-trifluoromethyl-3-thienylmethyl)-ethylene (or -trimethylene)diamine,
N-(1-methyl-5-trifluoromethyl-3-pyrrolylmethyl)-ethylene (or -trimethylene)diamine,
N-(5-methoxy-2-thienylmethyl)-ethylene (or -trimethylene) diamine,
N-(5-methylthiofurfuryl)-ethylene (or -trimethylene) diamine,
N-(2,5-dimethylthio-3-thienylmethyl)-ethylene (or -trimethylene)diamine,
N-(5-trifluoromethylthiofurfuryl)-ethylene (or -trimethylene) diamine,
N-[5-(2,2-dichlorovinyl)-2-thienylmethyl]-ethylene-(or -trimethylene)diamine,
N-(5-ethoxycarbonylfurfuryl)-ethylene (or -trimethylene) diamine,
N-(5-formyl-2-thienylmethyl)-ethylene (or -trimethylene) diamine,
N-(3-isoxazlylmethyl)-ethylene (or -trimethylene)diamine,
N-(4-isoxazolylmethyl)-ethylne (or -trimethylene)diamine,
N-(3-ethyl-5-isoxazolylmethyl)-ethylene (or -trimethylene) diamine,
N-(3-isopropyl-5-isoxazolylmethyl)-ethylne (or -trimethylene diamine,
N-(3-fluoro-5-isoxazolylmethyl)-ethylene (or -trimethylene) diamine,
N-(3-bromo-5-isoxazolylmethyl)-ethylene (or -trimethylene) diamine,
N-(3-hydroxy-5-isoxazolylmethyl)-ethylene (or -trimethylene)diamine,
N-(3-nitro-5-isoxazolylmethyl)-ethylene (or -trimethylene) diamine,
N-(3-cyano-5-isoxazolylmethyl)-ethylene (or -trimethylene) diamine,
N-(3-difluoromethyl-5-isoxazolylmethyl)-ethylene (or -trimethylene)diamine,
N-(3-chloromethyl-5-isoxazolylmethyl)-ethylene (or -trimethylene)diamine,
N-(3-methoxymethyl-5-isoxazolylmethyl)-ethylene (or -trimethylene)diamine,
N-(3-isopropoxymethyl-5-isoxazolylmethyl)-ethylene (or -trimethylene)diamine,
N-(3-trichloromethyl-5-isoxazolylmethyl)-ethylene (or -trimethylene)diamine,
N-(3-methoxy-5-isoxazolylmethyl)-ethylene (or -trimethylene)diamine,
N-(3-trifluoromethoxy-5-isoxazolylmethyl)-ethylene (or -trimethylene)diamine,
N-(2,5-dimethyl-4-isoxazolylmethyl)-ethylene (or -trimethylene)diamine,
N-(3-isothiazolylmethylene)-ethylene (or -trimethylene) diamine,
N-(4-isothiazolylmethyl)-ethylene (or -trimethylene)-diamine,
N-(3-pyrazolylmethyl)-ethylene (or -trimethylene)diamine,
N-[1-(4-pyrazolyl)ethyl)-ethylene (or -trimethylene)-diamine,
N-(1-methyl-3-pyrazolylmethyl)-ethylene (or -trimethylene)diamine,
N-(1-methyl-5-pyrazolylmethyl)-ethylene (or -trimethylene)diamine,
N-(1-propyl-4-pyrazolylmethyl)-ethylene (or -trimethylene) diamine,
N-[1-(2,2,2-trifluoroethyl)-3-pyrazolylmethyl]-ethylene (or -trimethylene)diamine,
N-(5-chloro-1-ethyl-3-pyrazolylmethyl)-ethylene (or -trimethylene)diamine,
N-(5-chloro-1-isopropyl-3-pyrazolylmethyl)-ethylene (or -trimethylene)diamine,
N-(3-chloro-1-methyl-3-pyrazolylmethyl)-ethylene (or -trimethylene)diamine,
N-(5-trifluoromethyl-3-pyrazolylmethyl)-ethylene (or -trimethylene)diamine,
N-(1-methyl-5-trifluoromethyl-3-pyrazolylmethyl)-ethylene (or -trimethylene)diamine,
N-(1-methyl-3-trifluoromethyl-5-pyrazolylmethyl)-ethylene (or -trimethylene)diamine,
N-(4-oxazolylmethyl)-ethylene (or -trimethylene)diamine,
N-(2-methyl-4-oxazolylmethyl)-ethylene (or -trimethylene) diamine,
N-(2-methyl-5-oxazolylmethyl)-ethylene (or -trimethylene) diamine,
N-(2-fluoro-5-oxazolylmethyl)-ethylene (or -trimethylene) diamine,
N-(2-chloro-5-oxazolylmethyl)-ethylene (or -trimethylene) diamine,
N-(2-trifluoromethyl-5-oxazolylmethyl)-ethylene (or -trimethylene)diamine,
N-(2-methylthio-5-oxazolylmethyl)-ethylene (or -trimethylene)diamine,
N-(2-trifluoromethoxy-5-oxazolylmethyl)-ethylene (or -trimethylene)diamine,
N-(2,4-dimethyl-5-oxazolylmethyl)-ethylene (or -trimethylene)diamine,
N-(5-ethoxycarbonyl-2-oxazolylmethyl)-ethylene (or -trimethylene)diamine,
N-[1-(5-thiazolyl)ethyl]-ethylene (or -trimethylene)-diamine,
N-(2-methyl-4-thiazolylmethyl)-ethylene (or -trimethylene) diamine,
N-[1-(2-methyl-5-thiazolyl)ethyl]-ethylene (or -trimethylene)diamine,
N-(2-ethyl-5-thiazolylmethyl)-ethylene (or -trimethylene) diamine,
N-(2-isopropyl-5-thiazolylmethyl)-ethylene (or -trimethylene)diamine,
N-(4-methyl-5-thiazolylmethyl)-ethylene (or -trimethylene) diamine,
N-(2-fluoro-4-thiazolylmethyl)-ethylene (or -trimethylene) diamine,
N-(2-fluoro-5-thiazolylmethyl)-ethylene (or -trimethylene) diamine,
N-[1-(2-chloro-5-thiazolylmethyl)ethyl]-ethylene (or -trimethylene)diamine,
N-(2-nitro-4-thiazolylmethyl)-ethylene (or -trimethylene) diamine,
N-(2-nitro-5-thiazolylmethyl)-ethylene (or -trimethylene) diamine,
N-(2-cyano-4-thiazolylmethyl)-ethylene (or -trimethylene) diamine,
N-(2-cyano-5-thiazolylmethyl)-ethylene (or -trimethylene) diamine,
N-(2-methylthio-4-thiazolylmethyl)-ethylene (or -trimethylene)diamine,
N-(2-mercapto-5-thiazolylmethyl)-ethylene (or -trimethylene)diamine,
N-(2-methylthio-5-thiazolylmethyl)-ethylene (or -trimethylene)diamine,
N-(2-difluoromethylthio-5-thiazolylmethyl)-ethylene (or -trimethylene)diamine,
N-(2-trifluoromethylthio-5-thiazolylmethyl)-ethylene (or -trimethylene)diamine, N-(2-chlorodifluoromethylthio-5-thiazolylmethyl)-ethylene (or -trimethylene)diamine,
N-[2-(2,2,2-trifluoroethylthio)-5-thiazolylmethyl]-ethylene (or -trimethylene)diamine,
N-{2-[2-(2,3,3-trichloro)propenylthio]-5-thiazolylmethyl}-ethylene (or -trimethylene)diamine,
N-(2-thiocyanato-5-thiazolylmethyl)-ethylene (or -trimethylene)diamine,
N-(2-amino-4-thiazolylmethyl)-ethylene (or -trimethylene) diamine,
N-(2-acetamino-4-thiazolylmethyl)-ethylene (or -trimethylene)diamine,
N-(2-methoxy-4-thiazolylmethyl)-ethylene (or -trimethylene)diamine,
N-(2-methoxy-5-thiazolylmethyl)-ethylene (or -trimethylene)diamine,
N-(2-trifluoromethoxy-5-thiazolylmethyl)-ethylene (or -trimethylene)diamine,
N-(2-difluoromethoxy-5-thiazolylmethyl)-ethylene (or -trimethylene)diamine,
N-(2-chloromethyl-5-thiazolylmethyl)-ethylene (or -trimethylene)diamine,
N-(2-difluoromethyl-5-thiazolylmethyl)-ethylene (or -trimethylene)diamine,
N-(2-trifluoromethyl-5-thiazolylmethyl)-ethylene (or -trimethylene) diamine,
N-[(2-(1,1,2,2-tetrafluoroethyl)-5-thiazolylmethyl]-ethylene (or -trimethylene) diamine,
N-(2-cyclopropyl-5-thiazolylmethyl)-ethylene (or -trimethylene) diamine,
N-(2-imidazolylmethyl)-ethylene (or -trimethylene)-diamine,
N-(1-methyl-5-imidazolylmethyl)-ethylene (or -trimethylene) diamine,
N-(2-fluoro-4-imidazolylmethyl)-ethylene (or -trimethylene) diamine,
N-(2-chloro-4-imidazolylmethyl)-ethylene (or -trimethylene) diamine,
N-(4-nitro-2-imidazolylmethyl)-ethylene (or -trimethylene) diamine,
N-(4-trifluoromethylthio-4-imidazolylmethyl)-ethylene (or -trimethylene) diamine,
N-(1,2-dimethyl-4-imidazolylmethyl)-ethylene (or -trimethylene) diamine,
N-(1-methyl-2-trifluoromethyl-4-imidazolylmethyl)-ethylene (or -trimethylene) diamine,
N-(1-methyl-1,2,3-triazol-4-ylmethyl)-ethylene (or -trimethylene) diamine,
N-[(1-methyl-1,2,3-triazol-4-yl)ethyl]-ethylene (or -trimethylene) diamine,
N-(3-methyl-1,2,4-triazol-5-ylmethyl)-ethylene (or -trimethylene)diamine,
N-(3-trifluoromethyl-1,2,4-triazol-5-ylmethyl)-ethylene (or -trimethylene)diamine,
N-(1,2,4-oxadiazol-5-ylmethyl)-ethylene (or -trimethylene) diamine,
N-(1,3,4-oxadiazol-2-ylmethyl)-ethylene (or -trimethylene) diamine,
N-(1,2,3-oxadiazol-5-ylmethyl)-ethylene (or -trimethylene) diamine,
N-(3-trifluoromethyl-1,2,4-oxadiazol-5-ylmethyl)-ethylene (or -trimethylene)diamine,
N-(2-methyl-1,3,4-oxadiazol-5-ylmethyl)-ethylene (or -trimethylene)diamine,
N-(2-trifluoromethyl-1,3,4-oxadiazol-5-ylmethyl)-ethylene (or -trimethylene)diamine,
N-[2-(2,2,2-trifluoroethyl)-1,3,4-oxadiazol-5-ylmethyl]-ethylene (or -trimethylene)diamine,
N-(1,2,4-thiadiazol-5-ylmethyl)-ethylene (or -trimethylene) diamine,
N-(1,2,3-thiadiazol-4-ylmethyl)-ethylene (or -trimethylene) diamine,
N-[1-(1,2,3-thiadiazol-5-yl)ethyl]-ethylene (or -trimethylene)diamine,
N-(1,3,4-thiadiazol-2-yl)-ethylene (or -trimethylene) diamine,
N-[1-(1,3,4-thiadiazol-2-yl)ethyl]-ethylene (or -trimethylene)diamine,
N-(1,2,5-thiadiazol-3-ylmethyl)ethylene (or -trimethylene) diamine,
N-(3-methyl-1,2,4-thiadiazol-5-yl)-ethylene (or -trimethylene)diamine,
N-(4-methyl-1,2,3-thiadiazol-5-ylmethyl)-ethylene-(or -trimethylene)diamine,
N-(2-methyl-1,3,4-thiadiazol-5-ylmethyl)-ethylene-(or -trimethylene)diamine,
N-(2-trifluoromethyl-1,3,4-thiadiazol-5-ylmethyl)-ethylene (or -trimethylene)diamine,
N-(2-fluoro-1,3,4-thiadiazol-5-ylmethyl)-ethylene-(or -trimethylene)diamine,
N-(2-chloro-1,3,4-thiadiazol-5-ylmethyl)-ethylene-(or -trimethylene)diamine,
N-(3-chloro-1,2,5-thiadiazol-4-ylmethyl)-ethylene-(or -trimethylene)diamine,
N-[1-(3-tetrahydrofuryl)ethyl]-ethylene (or -trimethylene) diamine,
N-(3-tetrahydrothienylmethyl)-ethylene (or -trimethylene) diamine,
N-[1-(3-tetrahydrothienyl)ethyl]-ethylene (or -trimethylene) diamine,
N-(1-methyl-3-pyrrolidinylmethyl)-ethylene (or -trimethylene)diamine,
N-(1,3-oxathiolan-2-ylmethyl)-ethylene (or -trimethylene) diamine,
N-(1,3-dioxolan-4-ylmethyl)-ethylene (or -trimethylene) diamine,
N-(1,3-oxathiolan-4-ylmethyl)-ethylene (or -trimethylene) diamine,
N-(1,3-dithiolan-4-ylmethyl)-ethylene (or -trimethylene) diamine,
N-(thiazolidin-5-ylmethyl)-ethylene (or -trimethylene) diamine,
N-(4-methyl-1,3-dioxolan-2-ylmethyl)-ethylene (or -trimethylene)diamine,
N-(2-methyl-1,3-oxathiolan-4-ylmethyl)-ethylene (or -trimethylene)diamine,
N-(2-chloromethyl-1,3-dioxolan-4-ylmethyl)-ethylene (or -trimethylene)diamine,
N-(2-trifluoromethyl-1,3-dioxolan-4-ylmethyl)-ethylene (or -trimethylene)diamine,
N-(2-oxo-1,3-dioxolan-4-ylmethyl)-ethylene (or -trimethylene)diamine,
N-(3-formyl-thiazolidin-5-ylmethyl)-ethylene (or -trimethylene)diamine,
N-(3-acetyl-thiazolidin-5-ylmethyl)-ethylene (or -trimethylene)diamine,
N-(2,5-dihydrothiophen-2-ylmethyl)-ethylene (or -trimethylene)-diamine,
N-(1,1-dioxo-2,5-dihydrothiophen-3-ylmethyl)-ethylene (or -trimethylene)diamine,
N-(2-isoxazolin-5-ylmethyl)-ethylene (or -trimethylene) diamine,
N-(3-methyl-2-isoxazolin-5-ylmethyl)-ethylene (or -trimethylene)diamine,
N-(3-trifluoromethyl-2-isoxazolin-5-ylmethyl)-ethylene (or or -trimethylene)diamine, N-[3-(2,2,2-trifluoroethyl)-2-isoxazolin-5-ylmethyl]-ethylene (or -trimethylene)diamine,
N-(2,4-dimethyl-2-oxazolin-4-ylmethyl)-ethylene (or -trimethylene)diamine,
N-(2-methyl-2-thiazolin-4-ylmethyl)-ethylene (or -trimethylene)diamine,
N-(2-oxazolidinon-5-ylmethyl)-ethylene (or -trimethylene)diamine,
N-(3-methyl-2-oxo-1,3-oxazolan-5-ylmethyl)-ethylene (or -trimethylene)diamine,
N-(2-methylamino-5-thiazolylmethyl)-ethylene (or -trimethylene)diamine,
N-(2-trifluoroacetamide-5-thiazolylmethyl)-ethylene (or -trimethylene)diamine,
N-(3-methyl-2-thioxo-thiazolidin-5-ylmethyl)-ethylene (or -trimethylene)diamine,
N-(3-chloro-1,2,4-oxadiazol-5-ylmethyl)-ethylene (or -trimethylene)diamine,
N-(5-carboxy-2-oxazolylmethyl)-ethylene (or -trimethylene)diamine,
N-(2-dimethylamino-5-thiazolylmethyl)-ethylene (or -trimethylene)diamine,
N-(5-phenoxyfurfuryl)-ethylene (or -trimethylene)-diamine,
N-(1-phenyl-4-pyrazolylmethyl)-ethylene (or -trimethylene) diamine,
N-(1-benzyl-4-pyrazolylmethyl)-ethylene (or -trimethylene) diamine,
N-(2-phenyl-4-thiazolylmethyl)-ethylene (or -trimethylene) diamine,
N-(1-benzyl-2-imidazolylmethyl)-ethylene (or -trimethylene)diamine,
N-(2-methylsulfinyl-5-thiazolylmethyl)-ethylene (or -trimethylene)diamine,
N-(2-methylsulfonyl-5-thiazolylmethyl)-ethylene (or -trimethylene)diamine,
N-(2-methylthio-1,3,4-thiadiazol-5-ylmethyl)-ethylene (or -trimethylene)diamine,
N-(2-methylsulfonyl-1,3,4-thiadiazol-5-ylmethyl)-ethylene (or -trimethylene)diamine,
N-(2-dimethylamino-5-thiazolylmethyl)-ethylene (or -trimethylene)diamine,
N-(5-carbamoyl-2-thiazolylmethyl)-ethylene (or -trimethylene)diamine,
N-(5-methylaminocarbonyl-2-thiazolylmethyl)-ethylene (or -trimethylene)diamine,
N-(5-dimethylaminocarbonyl-2-thiazolylmethyl)-ethylene (or -trimethylene)diamine,
N-(3-pyridylmethyl)-ethylene (or -trimethylene) diamine,
N-[1-(3-pyridyl)ethyl]-ethylene (or -trimethylene) diamine,
N-[1-(3-pyridyl)propyl]-ethylene (or -trimethylene) diamine,
N-[2-methyl-1-(3-pyridyl)propyl]-ethylene (or -trimethylene)diamine,
N-(4-pyridylmethyl)-ethylene (or -trimethylene) diamine,
N-(5-chloro-2-pyridylmethyl)-ethylene (or -trimethylene) diamine,
N-(2-fluoro-5-pyridylmethyl)-ethylene (or -trimethylene) diamine,
N-(2-chloro-5-pyridylmethyl)-ethylene (or -trimethylene) diamine,
N-[1-(2-chloro-5-pyridyl)ethyl]-ethylene (or -trimethylene) diamine,
N-(2-nitro-5-pyridylmethyl)-ethylene (or -trimethylene) diamine,
N-(2-cyano-5-pyridylmethyl)-ethylene (or -trimethylene) diamine,
N-(2-amino-5-pyridylmethyl)-ethylene (or -trimethylene) diamine,
N-(2-acetamido-5-pyridylmethyl)-ethylene (or -trimethylene)diamine,
N-(2-dimethylamino-5-pyridylmethyl)-ethylene (or -trimethylene)diamine,
N-(2-ethoxycarbonyl-5-pyridylmethyl)-ethylene (or -trimethylene)diamine,
N-(2-acetyl-5-pyridylmethyl)-ethylene (or -trimethylene) diamine,
N-(2-chloro-3-methyl-5-pyridylmethyl)-ethylene (or -trimethylene)diamine,
N-(2-difluoromethyl-5-pyridylmethyl)-ethylene (or -trimethylene) diamine,
N-(5-trifluoromethyl-2-pyridylmethyl)-ethylene (or -trimethylene)diamine,
N-(2-trifluoromethyl-5-pyridylmethyl)-ethylene (or -trimethylene)diamine,
N-(2-bromodifluoromethyl-5-pyridylmethyl)-ethylene (or -trimethylene)diamine,
N-(2-chlorodifluoromethyl-5-pyridylmethyl)-ethylene (or -trimethylene)diamine,
N-(trichloromethyl-5-pyridylmethyl)-ethylene (or -trimethylene)diamine,
N-[2-(2-chloroethyl)-5-pyridylmethyl]-ethylene (or -trimethylene)diamine,
N-[2-(2-fluoroethyl)-5-pyridylmethyl]-ethylene (or -trimethylene)diamine,
N-[2-(2,2,2-trifluoroethyl)-5-pyridylmethyl]-ethylene (or -trimethylene)diamine,
N-(2-difluoroethoxy-5-pyridylmethyl)-ethylene (or -trimethylene)diamine,
N-(2-trifluoromethoxy-5-pyridylmethyl)-ethylene (or -trimethylene)diamine,
N-[2-(2,2,2-trifluoroethoxy)-5-pyridylmethyl]-ethylene (or -trimethylene)diamine,
N-[2-(trifluoromethylthio)-5-pyridylmethyl]-ethylene (or -trimethylene)diamine,
N-(2-formyl-5-pyridylmethyl)-ethylene (or -trimethylene) diamine,
N-(2-chlorodifluoromethylthio-5-pyridylmethyl)-ethylene (or -trimethylene)diamine,
N-[2-(2,2-dichlorovinyl)-5-pyridylmethyl]-ethylene (or -trimethylene) diamine,
N-(5-trifluoromethyl-2-pyridylmethyl)-ethylene (or -trimethylene)diamine,
N-(5-methyl-2-pyridylmethyl)-ethylene (or -trimethylene) diamine,
N-(6-methyl-2-pyridylmethyl)-ethylene (or -trimethylene) diamine,
N-(4-methyl-2-pyridylmethyl)-ethylene (or -trimethylene) diamine,
N-(5-ethyl-2-pyridylmethyl)-ethylene (or -trimethylene) diamine,
N-(5-butyl-2-pyridylmethyl)-ethylene (or -trimethylene) diamine,
N-(4,6-dimethyl-2-pyridylmethyl)-ethylene (or -trimethylene)diamine,
N-(3-chloro-2-pyridylmethyl)-ethylene (or -trimethylene) diamine,
N-(3,5-dichloro-2-pyridylmethyl)-ethylene (or -trimethylene)diamine,
N-(5-fluoro-2-pyridylmethyl)-ethylene (or -trimethylene) diamine,
N-(6-bromo-2-pyridylmethyl)-ethylene (or -trimethylene) diamine,
N-[2-(5-ethyl-2-pyridyl)ethyl]-ethylene (or -trimethylene) diamine,
N-(6-chloro-4-methyl-2-pyridylmethyl)-ethylene (or -trimethylene)diamine, N-(5-methyl-3-pyridylmethyl)-ethylene (or -trimethylene) diamine,
N-(2-methyl-5-pyridylmethyl)-ethylene (or -trimethylene) diamine,
N-(2-chloro-3-pyridylmethyl)-ethylene (or -trimethylene) diamine,
N-(5-chloro-3-pyridylmethyl)-ethylene (or -trimethylene) diamine,
N-(5-bromo-3-pyridylmethyl)-ethylene (or -trimethylene) diamine,
N-(2-bromo-5-pyridylmethyl)-ethylene (or -trimethylene) diamine,
N-(5-fluoro-3-pyridylmethyl)-ethylene (or -trimethylene) diamine,
N-(2-fluoro-5-pyridylmethyl)-ethylene (or -trimethylene) diamine,
N-[(1-(2-fluoro-5-pyridyl)ethyl]-ethylene (or -trimethylene) diamine,
N-[2-methyl-1-(2-fluoro-5-pyridyl)propyl]-ethylene (or -trimethylene) diamine,
N-(2-chloro-6-methyl-3-pyridylmethyl)-ethylene (or -trimethylene)diamine,
N-(2,4-dichloro-5-pyridylmethyl)-ethylene (or -trimethylene)diamine,
N-(2,6-dichloro-3-pyridylmethyl)-ethylene (or -trimethylene)diamine,
N-(2,4-dibromo-5-pyridylmethyl)-ethylene (or -trimethylene)diamine,
N-(2,4-difluoro-5-pyridylmethyl)-ethylene (or -trimethylene) diamine,
N-(2-methoxy-3-pyridylmethyl)-ethylene (or -trimethylene) diamine,
N-(2-methoxy-5-pyridylmethyl)-ethylene (or -trimethylene) diamine,
N-(2-ethoxy-5-pyridylmethyl)-ethylene (or -trimethylene) diamine,
N-(2-isopropoxy-5-pyridylmethyl)-ethylene (or -trimethylene)diamine,
N-(2-methylthio-5-pyridylmethyl)-ethylene (or -trimethylene)diamine,
N-(4-methyl-2-methylthio-5-pyridylmethyl)-ethylene (or -trimethylene)diamine,
N-(2-ethylthio-5-pyridylmethyl)-ethylene (or -trimethylene) diamine,
N-(2-methylsulfinyl-5-pyridylmethyl)-ethylene (or -trimethylene)diamine,
N-(2-methylsulfonyl-5-pyridylmethyl)-ethylene (or -trimethylene)diamine,
N-(4-chloro-2-fluoro-5-pyridylmethyl)-ethylene (or -trimethylene)diamine,
N-(6-chloro-2-methyl-3-pyridylmethyl)-ethylene (or -trimethylene)diamine,
N-(2-chloro-4-methyl-5-pyridylmethyl)-ethylene (or -trimethylene)diamine,
N-(2-allyl-5-pyridylmethyl)-ethylene (or -trimethylene) diamine,
N-(2-propargyl-5-pyridylmethyl)-ethylene (or -trimethylene)diamine,
N-(2,3-dichloro-5-pyridylmethyl)-ethylene (or -trimethylene)diamine,
N-[2-(1-propenyl)-5-pyridylmethyl]-ethylene (or -trimethylene)diamine,
N-(2-chloro-4-pyridylmethyl)-ethylene (or -trimethylene) diamine,
N-(2-fluoro-4-pyridylmethyl)-ethylene (or -trimethylene) diamine,
N-(2,6-dichloro-4-pyridylmethyl)-ethylene (or -trimethylene)diamine,
N-(2-methyl-4-pyridylmethyl)-ethylene (or -trimethylene) diamine,
N-[1-(2-chloro-4-pyridyl)ethyl]-ethylene (or -trimethylene) diamine,
N-(2-chloro-6-methyl-4-pyridylmethyl)-ethylene (or -trimethylene)diamine,
N-(2,6-dimethyl-4-pyridylmethyl)-ethylene (or -trimethylene)diamine,
N-(2-bromo-4-pyridylmethyl)-ethylene (or -trimethylene) diamine,
N-(2,6-dibromo-4-pyridylmethyl)-ethylene (or -trimethylene)diamine,
N-(2,6-dichloro-4-pyridylmethyl)-ethylene (or -trimethylene)diamine,
N-(3-chloro-2-fluoro-5-pyridylmethyl)-ethylene (or -trimethylene)diamine,
N-(3-bromo-2-fluoro-5-pyridylmethyl)-ethylene (or -trimethylene)diamine,
N-(2-chloro-3-fluoro-5-pyridylmethyl)-ethylene (or -trimethylene)diamine,
N-(3-chloro-2-methylthio-5-pyridylmethyl)-ethylene (or -trimethylene)diamine,
2-amino-1-(4-pyridylmethylamino)propane,
2-amino-2-methyl-(3-pyridylmethylamino)propane,
N-(4-pyridylmethyl)-2,2-dimethyltrimethylenediamine,
2-amino-1-(2-chloro-5-pyridylmethylamino)propane,
N-(2-chloro-5-pyridylmethyl)-2-methyltrimethylenediamine,
N-(3-pyridylmethyl)-N'-methylethylenediamine,
N-(2-chloro-5-pyridylmethyl)-N'-methylethylene (or -trimethylene)diamine,
N-(2-fluoro-5-pyridylmethyl)-N'-isopropyl-ethylenediamine,
N-(2-chloro-5-pyridylmethyl)-N'-benzylethylene-diamine,
N-(2-chloro-5-pyridylmethyl)-N'-(3-pyridylmethyl) ethylenediamine,
N-(2-chloro-5-pyridylmethyl)-N'-(1-methyl-4-pyrazolylmethyl)ethylenediamine,
2-methyl-2-(2-methyl-5-pyridylmethylamino)ethanethiol,
1-methyl-2-(2-chloro-5-pyridylmethylamino)ethanethiol,
2-(4-pyridylmethylamino)ethanol,
2-(3-pyridylmethylamino)ethanol,
3-(2-methyl-3-pyridylmethyl) propanol,
2-(2-methyl-5-pyridylmethyl) ethanol,
2-(2-chloro-5-pyridylmethyl)ethanol,
3-(2-trifluoromethyl-5-pyridylmethyl)propanol,
N-(1-methyl-4-pyrazolylmethyl)-2,2-dimethyl-trimethylenediamine,
N,N'-bis-(5-methyl-2-furfuryl)ethylenediamine,
N-(3-methyl-5-isoxazolylmethyl)-N'-(1-methyl-4-pyrazolylmethyl) ethylene (or -trimethylene) diamine,
2-(3-methyl-5-isoxazolylmethylamino)ethanethiol,
3-(1-isopropyl-4-pyrazolylmethylamino)propanethiol,
2-(1,2,5-thiadiazol-3-ylmethylamino)ethanethiol,
2-(2-trifluoromethyl-5-thiazolylmethylamino)ethanethiol,
2-(3-methyl-5-isoxazolylmethylamino)ethanol,
2-(4-isothiazolylmethylamino)ethanol,
2-(5-oxazolylmethylamino)ethanol,
2-(3-trifluoromethyl-5-isoxazolylmethylamino) ethanol,
2-(5-pyrimidinylmethylamino)ethanethiol,
2-(3-trifluoromethyl-6-pyridazinylmethylamino)-ethanethiol,
2-(2-methyl-5-pyrazinylmethylamino)ethanethiol,
2-(3-pyrazinylmethylamino)ethanol,
2-(3-chloro-6-pyridazinylmethylamino)ethanol,
2-amino-1-(2-pyradinylmethyl) aminopropane,
N-(5-pyrimidinylmethyl)-N'-(1-methyl-4-pyrazolylmethyl) ethylenediamine, and N-(3-chloro-6-pyridazinylmethyl)-N'-methyethylenediamine.

As aforesaid, the formula (II) includes novel compounds.

In the case of the formula (II) having the following formula (IIa):

$$Z-CH(R)-NH-C(R^5)(R^6)-(C)_n(R^4)(R^3)-C(R^2)(R^1)-X^2H \quad (IIa)$$

wherein n, $R^1$, $R^2$, $R^3$, $R^4$, $R^5$, $R^6$, R and Z have the same meanings as stated above, $X^2$ represents an oxygen atom or $$-N(-R^{10})-,$$

$R^{10}$ has the same meanings as stated above, the compounds of the formula (IIa) can be obtained when (g) the compounds of the aforesaid formula (VIII) are reacted with the compounds of the formula (IX)

$$H_2N-C(R^5)(R^6)-(C)_n(R^4)(R^3)-C(R^2)(R^1)-X^2H \quad (IX)$$

wherein n, $R^1$, $R^2$, $R^3$, $R^4$, $R^5$, $R^6$ and $X^2$ have the same meanings as stated above, if appropriate, in the presence of inert solvents and in the presence of acid acceptors.

If, in the process (g), for example, pyrazinylmethyl chloride and ethylenediamine are used as starting materials, the course of the reaction can be represented by the following equation:

[pyrazine-CH$_2$Cl] + H$_2$N—(CH$_2$)$_2$—NH$_2$ ⟶

[pyrazine-CH$_2$—NH—(CH$_2$)$_2$—NH$_2$]

The compounds of the formula (II) can be obtained when (h) the compounds of the formula (X)

$$Z-C(=O)-R \quad (X)$$

wherein

Z and R have the same meanings as stated above, are reacted with the compounds of the formula (XI)

$$H_2N-C(R^5)(R^6)-(C)_n(R^4)(R^3)-C(R^2)(R^1)-X^1H \quad (XI)$$

wherein $R^1$, $R^2$, $R^3$, $R^4$, $R^5$, $R^6$ and $X^1$ have the same meanings as stated above, and the resulting products are reduced, if appropriate, in the presence of inert solvents.

If, in the process (h), for example, 6-chloronicotinealdehyde and 3-aminopropanethiol are used as starting materials, the course of the reaction can be represented by the following equation:

[Cl-pyridine]-C(=O)-H + H$_2$N—(CH$_2$)$_3$—SH ⟶

[Cl-pyridine]-CH(cyclic N-S with (CH$_2$)$_3$) →+H→

[Cl-pyridine]-CH$_2$—NH—(CH$_2$)$_3$—SH

In addition, if, in the process (h), for example, 5-pyrimidinecarbaldehyde and ethylenediamine are used as the starting materials, the course of the reaction can be represented by the following equation:

[pyrimidine]-CHO + H$_2$N—(CH$_2$)$_2$—NH$_2$ ⟶

[pyrimidine]-CH=N—(CH$_2$)$_2$—NH$_2$ →+(H)→

[pyrimidine]-CH$_2$—NH—(CH$_2$)$_2$—NH$_2$

The compounds of the formula (VIII), in the process (g), are the same as the starting materials in the process (f), as mentioned hereinafter.

The compounds of the formula (IX) which include both known and novel ones, can be easily produced by known processes.

As examples of the formula (IX), there may be mentioned:

ethylenediamine, and trimethylenediamine. (see German Offenlegungsschrift 2,732,660 or French Patent No. 1,499,785).

There may also be mentioned 2-aminoethanol and 3-aminopropanole which are well known compounds in organic chemistry.

In addition, N-benzyl-ethylene (or trimethylene) diamines [see Japanese Laid-Open Patent Application No. 78,971/1985, German Offenlegungsschrift 2,514,402, German Offenlegungsschrift 2,732,660 and Japanese Patent Application No. 63,551/1985] and N-substituted alkyl-ethylene (or trimethylene) diamines which correspond to ethylenediamines or trimethylenediamines in the aforesaid formula (II) also included as examples of the formula (IX).

In the practice of process (g), the desired compounds of the formula (II) can be easily obtained by reacting the compounds of formula (VII) with the compounds of formula (IX) in inert solvents such as illustrated in process (a) to be described in detail hereinbelow.

The process (g) can be easily carried out by using more than 1 mole, for example about 5 moles, of the compounds of the formula (IX) per mole of the compounds of the formula (VIII) at a reaction temperature in the range of, for example, 0 to 50° C.

The compounds of the formula (X) used as the starting material in process (h) include for the most part known compounds.

As examples, there may be exemplified:
6-chloronicotinaldehyde,
6-bromonicotinaldehyde,
6-fluoronicotinaldehyde,
5-acetyl-2-chloropyridine,
5,6-dichloronicotinaldehyde,
5-chloro-6-fluoronicotinaldehyde,
2-chloro-4-pyridylcarbaldehyde,
3-chloro-2-pyridinecarbaldehyde,
3,5-dichloro-2-pyridinecarbaldehyde,
5-fluoro-2-pyridinecarbaldehyde,
6-bromo-2-pyridinecarbaldehyde,
2-chloronicotinaldehyde,
5-chloronicotinaldehyde,
5-bromonicotinaldehyde,
5-fluoronicotinaldehyde,
5-acetyl-2-fluoropyridine,
4,6-dichloronicotinaldehyde,
4,6-dibromonicotinaldehyde,
2,6-difluoro-4-pyridinecarbaldehyde,
2-fluoro-4-pyridinecarbaldehyde,
2,6-dibromo-4-pyridinecarbaldehyde,
5-bromo-6-fluoronicotinaldehyde,
6-chloro-5-fluoronicotinaldehyde,
2-chloro-5-propionylpyridine,
nicotinaldehyde,
4-pyridinecarbaldehyde,
6-methylnicotinaldehyde,
6-ethylnicotinaldehyde,
6-allylnicotinaldehyde,
6-propargylnicotinaldehyde,
6-methoxynicotinaldehyde,
6-methylthionicotinaldehyde,
6-methylsulfonylnicotinaidehyde,
6-chloro-4-methylnicotinaldehyde,
3-acetylpyridine,
6-nitronicotinaldehyde,
6-cyanonicotinaldehyde,
6-methylsulfinylnicotinaldehyde,
6-phenylnicotinaldehyde,
6-benzylnicotinaldehyde,
6-phenoxynicotinaldehyde,
6-(2-ethoxyethyl) nicotinaldehyde,
6-trichloromethylnicotinaldehyde,
6-methoxymethylnicotinaldehyde,
6-difluoromethoxynicotinaldehyde,
6-trifluoromethoxynicotinaldehyde,
6-(2,2,2-trifluoroethoxy)nicotinaldehyde,
6-chlorodifluoromethylthionicotinaldehyde,
6-trifluoromethylthionicotinaldehyde,
6-difluoromethylnicotinaldehyde,
6-trifluoromethylsulfonylnicotinaldehyde,
6-trifluoromethylsulfinylnicotinaldehyde,
6-(2,2-dichlorovinyl)nicotinaldehyde,
4-pyrimidinecarbaldehyde,
2-methyl-4-pyrimidinecarbaldehyde,
2-methyl-6-oxo-1H,6H-dihydropyrimidine-4-carbaldehyde,
5-pyrimidinecarbaldehyde,
2-methyl-5-pyrimidinecarbaldehyde,
2-dimethylamino-5-pyrimidinecrbaldehyde,
2,4,6-trichloro-5-pyrimidinecarbaldehyde,
pyrazylcarbaldehyde,
acetylpyrazine,
2-methyl-5-pyrazinecarbaldehyde,
3-pyridazinecarbaldehyde,
2-chloro-4-pyrimidinecarbaldehyde,
4-chloro-6-pyrimidinecarbaldehyde,
4-methyl-6-pyrimidinecarbaldehyde,
2-fluoro-5-pyrimidinecarbaldehyde,
5-acetyl-2-fluoropyrimidine,
2-chloro-5-pyrimidinecarbaldehyde,
2-isopropyl-5-pyrimidinecarbaldehyde,
2-chlorodifluoromethyl-5-pyrimidinecarbaldehyde,
2-trifluoromethyl-5-pyrimidinecarbaldehyde,
2-bromodifluoromethyl-5-pyrimidinecarbaldehyde,
2-methoxy-5-pyrimidinecarbaldehyde,
2-difluoromethoxy-5-pyrimidinecarbaldehyde,
2-trifluoromethoxy-5-pyrimidinecarbaldehyde,
2-(2,2,2-trifluoroethoxy)-5-pyrimidinecarbaldehyde,
2-methylthio-5-pyrimidinecarbaldehyde,
2-ethylthio-5-pyrimidinecarbaldehyde,
2-difluoroethylthio-5-pyrimidinecarbaldehyde,
2-trifluoromethylthio-5-pyrimidinecarbaldehyde,
2-nitro-5-pyrazinecarbaldehyde,
2-cyano-5-pyrazinecarbaldehyde,
2-chloro-5-pyrazinecarbaldehyde,
2-trifluoromethyl-5-pyrazinecarbaldehyde,
3-fluoro-6-pyridazinecarbaldehyde,
3-methyl-6-pyridazinecarbaldehyde,
4-pyridazinecarbaldehyde,
3-chloro-6-pyridazinecarbaldehyde,
3-trifluoromethyl-6-pyridazinecarbaldehyde,
1,3,5-triazine-2-carbaldehyde,
3-chloro-1,2,4-triazine-6-carbaldehyde,
3,5-dichloro-1,2,4-triazine-6-carbaldehyde, and
3-chloro-1,2,4,5-tetrazine-6-carbaldehyde.

The compounds of the formula (X) can be produced according to various conventional methods. They will be specifically described below.

For example, the pyridinecarbaldehydes of the formula (X) can be produced by reacting the corresponding vinylpyridines according to ozonolysis reaction (see J. org. chem., vol.26, 4912–4914) and in accordance with British Patent No. 2,002,368, 6-chloronicotinaldehyde can be derived from 2-chloro-5-pyridylcarbonitrile.

In general, moreover, the formula (X) may be produced without difficulty, according to a conventional method reducing the corresponding carboxylic acids and the esters thereof or by the Vilsmeyer reaction.

For example, pyridinecarbaldehydes also may be produced by reduction of the corresponding pyridinecarboxylic acids and the esters thereof (see Org. React., vol.8, 218–257).

The formula (X) also may be directly prepared by ring formation. For example, with regards to 4-pyrimidinecarbaldehyde, the corresponding 2-methylthio-4-methyl-6-pyrimidinecarbaldehyde acetal is obtained by reacting diethoxyacetylacetone with S-methylisothiourea. Subsequent reduction and treatment with hydrochloric acid give 4-methyl-6-pyrimidinecarbaldehyde. The use of diethoxyacetylacetone derivatives in this reaction can lead to the synthesis of similar compounds such as 4-pyrimidinecarbaldehyde, 2-methyl-4-pyrimidinecarbaldehyde and 2-trifluoromethyl-4-pyrimidinecarbaldehyde (described in Chem. Ber., vol. 97, pages 3407–3417). Many known methods of synthesizing 5-pyrimidinecarbaldehydes are known in the field of organic chemistry.

For example, 5-pyrimidinecarbaldehyde can be synthesized by introducing a formyl group into the 5-position of 4-hydroxy-6-oxodihydropyrimidine by the Vilsmeyer reaction, halogenating the product to form 4,6-dichloro-5-formylpyrimidine, and then dehalogenating the resulting compound (Liebigs Ann. Chem., vol. 766, pages 73–83; and Monatsh. Chem., vol. 96, pages 1567–1572). By applying this reaction, 2-alkyl-substituted and 2-haloalkyl-substituted 5-pyrimidinecarbaldehydes can be synthesized. 5-pyrimidinecarbaldehydes having other substituents at the 2-position are described in Japanese Laid-Open Patent Publication No. 59669/1984.

For example, 5-pyrimidinecarbaldehydes having substituents such as alkyl, alkoxy, alkylthio or alkylamino at the 2-position are obtained by reacting {2-[1(dimethylamino)-methylene]propanediylidene}bis [dimethylaminoperchlorate] (described in Collect. Czech. Chem. Comm., vol. 30, page 2125) with suitable amidine hydrochlorides.

As regards 5-pyrimidinecarbaldehydes having halogen at the 2-position, 2-chloro-5-pyrimidinecarbaldehyde can be obtained, for example, by chlorinating ethyl 2-oxo-1,2-dihydro-5-pyrimidinecarboxylate with phosphorus oxychloride to obtain ethyl 2-chloro-5-pyrimidinecarboxylate (Chem. Pharm. Bull., vol. 12, pages 804–808; a similar example in J. Org. Chem., vol. 29, pages 1740–1743), and reducing the resulting compound in a customary manner. Since the chlorine atom at the 2-position has activity, it may be converted to another substituent such as 2-fluoro by using potassium fluoride.

With regard to pyridazinecarbaldehydes, 3- and 4-pyridazinecarbaldehydes are described at page 213 of Monatsh. Chem., vol. 108, and methyl-substituted pyridazinecarbaldehydes, in J. Heterocycle. Chem., Vol. 17, page 1501.

Moreover, with regard to 5-membered heterocyclic-carbaldehydes, they will be specifically described below. Furfural is a known compound, and can easily permit introduction of a halogen atom into the furan ring. For example, 5-chlorofurfural and 4,5-dichlorofurfural can be synthesized from furfural (Zh. Org. Khim., Vol. 11, pages 1955–1958). 5-Nitrofurfural is also an easily available known compound. 5-Cyano-furfural is a compound described in Tetrahedron, Vol. 39, page 3881, and 5-phenoxyfurfural is a compound described in Chem. Pharm. Bull., Vol. 28, No. 9, page 2846. Furancarbaldehydes other than furfural, alkyl-substituted, particularly methyl-substituted, furfurals and other furancarbaldehydes are also known compounds and can be easily obtained.

Thiophene carbonyl aldehyde is a known compound, and a halogen atom can be easily introduced into the thiophene ring. For example, 2,3-dichloro-4-thiophene carbaldehyde can be synthesized from 3-thiophene carbaldehyde (Tetrahedron Vol., 32, pages 1403–1406). 2,3-Dibromo-5-thiophene carbaldehyde can be synthesized from 2-thiocarbaldehyde (J. Org. Chem., Vol. 41, page 2835). Alkyl-substituted, particularly methyl-substituted, thiophene carbaldehydes are also known compounds. Alkylthio-substituted or halogenoalkylthio-substituted thiophenonecarbaldehydes can be obtained by alkylating or haloalkylating mercapto-substituted thiophene carbaldehyde. For example, 2-methylthio-5-thiophenecarbaldehyde is a known compound described in Zh. Obshch. Khim., Vol. 34; pages 4010–4015. Generally, alkylthio-substituted or halogenoalkylthio-substituted heterocyclic carbaldehydes can be synthesized by the above methods.

Nitro-substituted thiophenecarbaldehydes can easily be synthesized by nitration or the thiophene ring. For example, 4-nitro-2-thiophenecarbaldehyde and 2-nitro-4-thiophenecarbaldehyde are known compounds described in Bull. Soc. Chim. France, 1963, pages 479–484.

Pyrrole carbaldehydes are known compounds. 1-Methyl-2-pyrrole carbaldehyde can be synthesized from 1-methylpyrrole by the Vilsmeir reaction or by methylating 2-pyrrole carbaldehyde (Beilstein, Vol. 21, I, page 279).

4-iso-Thiazole carbaldehyde can be synthesized from 4-isothiazolylcarboxylic acid (J. Medicin. Chem., Vol. 13, pages 1208–1212), and 5-isothiazole carbaldehyde can be synthesized from 5-isothiazolyl lithium (J. Chem. Soc. 1964, pages 446–451).

5-Pyrazole carbaldehyde and 3-methyl-5-pyrazole carbaldehyde can be synthesized by direct ring synthesis (Chem. Ber. Vol. 97, pages 3407–3417). By a similar method, 3-trifluoromethyl-5-pyrazole carbaldehyde can be synthesized.

A formyl group can be introduced into the 4-position or an N-alkyl or N-aryl pyrazole by the Vilsmeyer reaction. 4-Pyrazole carbaldehyde can be obtained by eliminating benzyl from N-benzyl-4-pyrazole carbaldehyde (J. Chem. Soc., 1957, pages 3314 and 1115).

4-Methyl-5-imidazole carbaldehyde and 1-methyl-5-imidazole carbaldehyde are known compounds (J. Pharm. Soc. Japan, Vol. 60, pages 184–188; J. A. C. S., Vol. 71, pages 2444–2448).

Many substituted thiazole carbaldehydes are known (Japanese Laid-Open Patent Publication No. 205,370/1984; Chem. Ab., Vol. 62, 7764d; Chem. Ber., Vol. 101, page 3872). For example, 2-chlorothiazole-5-carbaldehyde can be synthesized by lithiation with butyllithium followed by formylation. Substituted 1,3,4-thiadiazole carbaldehyde is are also known compounds (Japanese Laid-Open Patent Publication No. 206370/1984). 1,2,3-Thiadiazole-5-carbaldehyde is also a known compound (British Patent No. 1,113,705).

The compounds of the formula (XI), in the process (h) encompass the compounds of the aforesaid formula (IX).

In addition, as examples, 2-aminoethanethiol and 3-aminopropanethiol are exemplified (see J. Org. Chem., vol. 27, 4712–4713) and the aminoalkanethiols, based on them, also may be included.

For example, in the case of $X^3$ being a sulfur atom, the above process (h) can be carried out in the same way as described in J. Org. Chem., vol.27, 2452–2457 and 4712–4713.

In carrying out the process (c), as first-step, the thiazolidines or the tetrahydrothiazines can be produced, as intermediate products, by reacting the compounds of the formula (X) with the compounds of the formula (XI) in the presence of inert solvent, such as benzene, and, as next-step, the intermediates can be reduced by a reducing agent such as sodium boron hydride, lithium aluminum hydride, aluminum boron hydride, potassium boron hydride, etc., to produce the compounds of the formula (IIb).

In carring out the process (h) practically, the thiazolidines or the tetrahydrothiazines as intermediate products not only can be obtained by distilling off volatile matter following the reaction of the first-step, under reduced pressure, for instance, 1 mmHg, at 50–80° C., but also can be subjected to the reduction directly without the isolation.

In the case of $X^3$ being

according to process (h), the desired compound of the formula (IIb) can be obtained by heating the starting materials under reflux in an inert solvent (such as benzene), and directly reducing the reaction mixture in a customary manner without separating the intermediate Schiff base or imine, as will be specifically shown in a working example given hereinbelow.

In carrying out the process (h), more than 1 mole, for example about 5 moles, of the compounds of the formula (XI) are used preferably per mole of the compounds of the formula (X), and the reaction is preferably carried out under atmospheric pressure at a temperature of usually 0 to 100° C.

Moreover, as an alternative process for the preparation of the formula (II) in which $X^1$ is a sulfur atom, there also may be cited a process which comprises halogenating the compounds of the formula (II) in which $X^1$ is an oxygen atom by a halogenating agent such as thionylchloride, and thereafter reacting the resulting products with potassium hydrogen sulfide.

The compounds of the formula (III), in the process (a), include both known and novel compounds.

As examples of known compounds, there may be mentioned: (for example, see Chem. Ber., vol.100, 591–604)
1-nitro-2,2-bis(methylthio)ethylene,
1-nitro-2,2-bis(ethylthio)ethylene,
1-nitro-2,2-bis(benzylthio)ethylene, and
2-nitromethylene-1,3-dithiolane.

The above compounds can be produced in a customary manner which comprises reacting nitromethane with carbon disulfide in the presence of base and alkylating the resulting product.

If other nitroalkanes are used in place of nitromethane in said process, similar compounds corresponding to the formula (III) may be produced easily.

In addition, if the acyl-substituted nitromethanes are used in place of nitromethane in said process, the desired formula (III) may be produced.

For example, if benzoylnitromethane is used, 1-benzoyl-1-nitro-2,2-bismethylthioethylene, a novel compound, can be produced, and if acetylnitromethane is used, 1-acetyl-1-nitro-2,2-bis(methylthio)ethylene, a novel compound, can be produced easily.

The compounds of the formula (IV), in the process (b), are known. (see Chem. Abst., vol.44, 1011F, Japanese Laid-Open Patent Application No. 137,473/1984).

As examples, there may be mentioned:
2,2-dichloronitroethylene,
1,2,2-trichloronitroethylene,
1-fluoro-2,2-dichloronitroethylene,
1-methyl-2,2-dichloronitroethylene.

The compounds of the formula (V), in the process (c), are known. (see J. Org. Chem., vol.25, 1312, ibid, vol.28, 1281–1283, Chem. Ber., 75B, 1323–1330, Japanese Laid-Open Patent Application No. 48,978/1985).

As examples, there may be mentioned:
2,2,2-trichloro-1-nitroethane,
1,2,2,2-tetrachloro-1-nitroethane,
2,2,2-trifluoro-1-nitroethane.

The formula (VI) provides a general definition of the compounds required as a starting material in the process (e). based on aforesaid each definition of n, $R^1$, $R^2$, $R^3$, $R^4$, $R^5$, $R^6$, X, R and Z.

In the formula (VI), n, $R^1$, $R^2$, $R^3$, $R^4$, $R^5$, $R^6$, X, R and Z preferably have the meanings already given above.

The compounds of the formula (VI) include both known and novel ones. For example, 2-imino-3-(4-pyridylmethyl) thiazolidine has been disclosed in C. Med. Chem. vol.22, 237–247.

Other compounds of the formula (VI) also can be produced in the same way as disclosed in the above reference.

The compounds of the formula (VI), for example, can be produced by reacting the aforesaid compounds of the formula (II) with cyanogen halides.

Said reaction can be easily achieved by mixing the reactants with stirring in inert solvents, and the resulting products can be obtained in the form of a hydrohalide.

As specific examples of the formula (VI) (in the form of a hydrohalide), there may be mentioned:

Hydrobromides or hydrochlorides of
1-(2-chloro-5-pyridylmethyl)-2-iminoimidazolidine,
1-(2-chloro-5-pyrimidylmethyl)-2-iminotetrahydropyrimidine,
1-(2-fluoro-5-pyridylmethyl)-2-iminoimidazolidine,
1-(2-bromo-5-pyridylmethyl)-2-iminoimidazolidine,
1-(2-trifluoromethyl-5-pyridylmethyl)-2-iminoimidazolidine,
1-(2-methyl-5-pyridylmethyl)-2-iminoimidazolidine,
1-(3-pyridylmethyl)-2-iminoimidazolidine,
1-(3-pyridylmethyl)-2-tetrahydropyrimidine,
1-(2-trifluoromethoxy-5-pyridylmethyl)-2-iminoimidazolidine), and
1-(2-methoxy-5-pyridylmethyl)-2-iminoimidazolidine.

The formula (VII) provides a general definition of the compounds required as a starting material in the process (f), based on aforesaid each definition of n, $R^1$, $R^2$, $R^3$, $R^4$, $R^5$, $R^6$, X and Y.

In the formula (VII), n, $R^1$, $R^2$, $R^3$, $R^4$, $R^5$, $R^6$, X and Y preferably have the meanings already given above.

The compounds of the formula (VII) are for the most part, known.

As examples, there may be mentioned:
2-nitromethyleneimidazolidine,
2-nitromethylenetetrahydropyrimidine,
4,4-dimethyl-2-nitromethyleneimidazolidine,
3-methyl-2-nitromethyleneimidazolidine,
3-allyl-2-nitromethyleneimidazolidine,
3-propargyl-2-nitromethyleneimidazolidine,
3-(3-chloroallyl)-2-nitromethyleneimidazolidine,
3-acetyl-2-nitromethyleneimidazolidine,
3-chloroacetyl-2-nitromethyleneimidazolidine,
3-benzoyl-2-nitromethyleneimidazolidine,
3-p-tosyl-2-nitromethyleneimidazolidine,
2-nitromethylenethiazolidine,
2-nitromethylene-tetrahydro-2H-1,3-thiazine,
2-nitromethylene-5-methylthiazolidine,
2-nitromethyleneoxazolidine,
2-nitromethylene-4-methyloxazolidine,
2-nitromethylene-tetrahydro-2H-1,3-oxazine,
2-nitromethylenepyrolidine,
2-nitromethylenepiperidine,
2-(1-nitroethylidene)imidazolidine, 2-(1-nitro-2-fluoroethylidene)imidazolidine,
2-(phenyl, nitromethylene)imidazolidine,
2-(1-nitro-2,2,2-trifluoroethylidene)imidazolidine,
ethyl nitro(imidazolidin-2-ylidene)acetate,
n-butyl nitro(tetrahydropyrimidin-2-ylidene)acetate,
o-tolyl nitro(imidazolidin-2-ylidene)acetate,
p-chlorophenyl nitro(imidazolidin-2-ylidene)acetate,
p-nitrophenyl nitro(imidazolidin-2-ylidene)acetate,
2-(methylthionitromethylene) imidazolidine,
2-(propylthionitromethylene) imidazolidine,
2-[(4-chlorophenylthio)nitromethylene]imidazolidine,
2-(acetylnitromethylene)imidazolidine,
2-dinitromethylene)imidazolidine,
2-(benzoylnitromethylene)imidazolidine,
ethyl nitro(1-ethoxycarbonylimidazolidin-2-ylidene) acetate,
phenyl nitro(1-phenylthiocarbonylimidazolidin-2-ylidene) thiolacetate,
2-(phenylthionitromethylene)-1-phenylthioimidazolidine,
2-(1-nitroethylidene)-tetrahydro-2H-1,3-thiazine,
2-(1-nitro-3-butynylidene)thiazolidine,
2-(1-nitro-3-butynylidene)-tetrahydro-2H-1,3-thazine,
2-(1-nitro-2-phenylethylidene)thiazolidine,
2-(3-acetyl-1-nitropropylidene)-tetrahydro-2H-1,3-thiazine,
2-(3-cyano-1-nitropropylidene)-tetrahydro-2H-1,3-thazine,
methyl 4-nitro-4-(thiazolidin-2-ylidene)butyrate,
2-(2-ethylthio-1-nitroethylidene)-tetrahydro-2H-1,3-thiazine,
2-(2-dimethylamino-1-nitroethylidene)thiazolidine,
ethyl nitro(tetrahydro-2H-1,3-thazin-2-ylidene) acetate,
phenyl nitro(tetrahydro-2H-1,3-thiazin-2-ylidene) acetate,
2-formylnitromethylenethiazolidine,
2-acetylnitromethylene-tetrahydro-2H-1,3-thiazine,
2-benzoylnitromethylene-tetrahydro-2H-1,3-thiazine,
2-phenylthionitromethylene-tetrahydro-2H-1,3-thiazine,
ethyl nitro(oxazolidin-2-ylidene)acetate,
ethyl nitro(tetrahydro-2H-1,3-oxazin-2-ylidene) acetate,
3-methyl-2-nitromethylenepyrolidine,
3-fluoro-2-nitromethylenepiperidine,
methyl nitro(pyrrolidin-2-ylidene)acetate,
3-methylthio-2-nitromethylenepiperidine,
ethyl nitro(thiazolidine-2-ylidene)acetate,
2-nitroiminoimidazolidine,
4,4-dimethyl-2-nitroiminoimidazolidine,
2-nitroiminotetrahlydropyrimidine,
3-methyl-2-nitroiminoimidazolidine,
3-isopropyl-2-nitroiminoimidazolidine,
3-(2-ethoxyethyl) 2-nitroiminoimidazolidine,
3-ethoxycarbonyl-2-nitroiminoimidazolidine,
3-phenylthio-2-nitroiminoimidazolidine,
3-formyl-2-nitroiminoimidazolidine,
3-acetyl-2-nitroiminotetrahydropyrimidine,
3-(2-bromo-3,3-dimethylbutylyl) 2-nitroimidazolidine,
3-(2-trifluoromethylbenzoyl) 2-nitroiminoimidazolidine,
3-(2,4-dichloro-3-methylbenzoyl)-2-nitroiminoimidazolidine,
3-(4-methoxybenzoyl)-2-nitroiminoimidazolidine,
3-(3-chloropropylsulfonyl)-2-nitroiminoimidazolidine,
3-(2-difluoromethoxybenzoyl)-2-nitroiminotetrahlydropyrimidine,
3-phenoxycarbonyl-2-nitroiminoimidazolidine,
3-(2-froyl) 2-nitroiminotetrahlydropyrimidine,
3-(2-methylthiazol-5-ylcarbonyl)-2-nitroiminoimidazolidine,
3-(diethoxyphosphono)-2-nitroiminoimidazolidine,
3-(5-nitro-2-mmethylbenzenesulfonyl)-2-nitroiminoimidazolidine,
2-nitroiminothiazolidine,
2-nitroiminotetrahydro-2H-1,3-thiazine,
2-nitroiminoxazolidine,
4-methyl-2-nitroiminooxazolidine,
2-nitroiminopyrrolidine,
2-nitroiminopiperidine,
3-methyl-2-nitroiminopyrrolidine, and
2-nitroiminotetrahydro-2H-1,3-oxazine.

2-nitromethylene-imidazolidines (or tetrahydropyrimidines), of the above said formula (VII), are known compounds (see, for instance, Chem. Ber., vol.100, 591–604, Belgian Patent No. 821, 281, U.S. Pat. No. 3,971, 774).

In addition, N-acyl derivatives from 2-nitromethylene-imidazolidines (or tetrahydropyrimidines) can be produced by known processes (see Japanese Laid-Open Patent Application Nos. 67,473/1985 and 61,575/1985).

Moreover, in the case of another group, besides a nitro group, being attached to the methylene group of 2-nitromethylene-imidazolidines (or tetrahydropyrimidines), said compounds of the formula (VII) can be produced, in accordance with the known process described in U.S. Pat. Nos. 3,996,372, 4,002,765, 4,042,696, 4,052,411, 4,053,619, 4,053,622 and 4,053,623 and Japanese Laid-Open Patent Application No. 151,727/1977 and Belgian Patent No. 821,282.

2-nitromethylene-thiazolidines (or tetrahydro-2H-1,3-thiazines) are also, for the most part, known compounds which can be easily produced, for instance, by reacting aminoalkanethiols with the aforesaid formula (III) that may be replaced by the aforesaid formula (IV) or formula (V).

Moreover, 2-position of 2-nitromethylene-thiazolidines (or tetrahydro-2H-1,3-thiazines) may be substituted by various known processes to obtain desired starting materials of the formula (VII). (see U.S. Pat. Nos. 3,962,234, 4,022,775, 4,024,254, 4,044,128, 4,045,434 and 4,076,813, and Japanese Laid-Open Patent Application No. 151,882/1975).

2-nitromethylene-oxazolidines (or -tetrahydro-2H-1,3-oxazines) are also known compounds which can be produced by reacting aminoalkanols with the aforesaid formula (III) that may be replaced by the aforesaid formula (IV) or formula (V). [see Adv. Pestic. Sci., Plenary Lect. Symp. Pap. Int. Congr. Pestic. Chem. 4-th, 1978, 206–217 (ref. Chem. abst., vol. 91, 103,654), U.S. Pat. No. 3,907,790, Japanese Laid-Open Patent Application Nos. 151,882/1975 and 151, 727/1977].

2-nitromethylene-pyrrolidines (or piperidines) are also known compounds which, for example, can be produced by reacting 2-methoxypyrrolidine-1 with nitroalkanes. (see Netherland Patent Nos. 7,306,020 and 7,306,145).

2-nitroimino derivatives of the formula (VII) are also known compounds.

For instance, 2-nitroiminooxazolidines are described in J. Am. Chem. Soc., vol.73, 2213–2216.

2-nitroiminoimidazolidines, 2-nitroiminotetrahydropyrimidines and N-acetyl derivatives thereof are described in J. Am. Chem. Soc., vol.73, 2201–2205 and British Patent No. 2,055,796.

N-acyl derivatives, excluding N-acetyl derivatives, N-sulfenyl derivatives, N-sulfonyl derivatives and N-phosphono derivatives are novel compounds which may be produced in the same way as described in British Patent No. 2,055,796.

2-nitroimino-thiazolidines (or tetrahydro-2H-1,3-thiazines, 2-nitroimino-pyrrolidines or (piperidines) which can be produced by reacting nitroguanidine with the diamines, the aminoalkanols or the aminoalkanethiol, or by reacting 2-imino compound with nitric acid in the presence of sulfuric acid, are also described in the aforesaid British Patent.

The formula (VIII) provides a general definition of the compounds required as a starting material in the process (f), based on aforesaid each definition of Z and R.

In the formula (VIII), Z and R preferably have the meanings already given above.

The compounds of the formula (VIII) usable according to the invention include known compounds, for instance, those already disclosed in J. Org. Chem., vol.34, 3547, J. Medicin. Chem., vol.14, 211–213 and 557–558, 1971, U.S. Pat. No. 4,332,944, J. Heterocycl. Chem., 1979, vol.16, 333–337.

As examples, there may be mentioned:
3-picolyl chloride,
1-(3-pyridyl)ethyl chloride,
1-(3-pyridyl)propyl chloride,
2-methyl-1-(3-pyridyl)propyl chloride,
4-picolyl chloride,
5-chloro-2-pyridylmethyl chloride,
2-fluoro-5-pyridylmethyl chloride,
2-chloro-5-pyridylmethyl chloride,
1-(2-chloro-5-pyridyl)ethyl chloride,
2-nitro-5-pyridylmethyl chloride,
2-cyano-5-pyridylmethyl chloride,
2-amino-5-pyridylmethyl chloride,
2-acetamide-5-pyridylmethyl chloride,
2-dimethylamino-5-pyridylmethyl chloride,
2-ethoxycarbonyl-5-pyridylmethyl chloride,
2-acetyl-5-pyridylmethyl chloride,
2-chloro-3-methyl-5-pyridylmethyl chloride,
2-difluoromethyl-5-pyridylmethyl chloride,
5-trifluoromethyl-2-pyridylmethyl chloride,
2-bromodifluoromethyl-5-pyridylmethyl chloride,
2-chlorodifluoromethyl-5-pyridylmethyl chloride,
2-trichloromethyl-5-pyridylmethyl chloride,
2-(2-chloroethyl)-5-pyridylmethyl chloride,
2-(2-fluoroethyl)-5-pyridylmethyl chloride,
2-(2,2,2-trifluoroethyl)-5-pyridylmethyl chloride,
2-difluoroethoxy-5-pyridylmethyl chloride,
2-trifluoroethoxy-5-pyridylmethyl chloride,
2-(2,2,2-trifluoroethoxy)-5-pyridylmethyl chloride,
2-(trifluoromethylthio)-5-pyridylmethyl chloride,
2- formyl-5-pyridylmethyl chloride,
2-chlorodifluoromethylthio-5-pyridylmethyl chloride,
2-(2,2-dichlorovinyl)-5-pyridylmethyl chloride,
5-trifluoromethyl-2-pyridylmethyl chloride,
5-methyl-2 -pyridylmethyl chloride,
6-methyl-2-pyridylmethyl chloride,
4-methyl-2-pyridylmethyl chloride,
5-ethyl-2-pyridylmethyl chloride,
5-butyl-2-pyridylmethyl chloride,
4,6-dimethyl-2-pyridylmethyl chloride,
3-chloro-2-pyridylmethyl chloride,
3,5-dichloro-2-pyridylmethyl chloride,
5-fluoro-2-pyridylmethyl chloride,
6-bromo-2-pyridylmethyl chloride,
6-chloro-4-methyl-2-pyridylmethyl chloride,
5-methyl-3-pyridylmethyl chloride,
2-methyl-5-pyridylmethyl chloride,
2-chloro-3-pyridylmethyl chloride,
5-chloro-3-pyridylmethyl chloride,
5-bromo-3-pyridylmethyl chloride,
2-bromo-5-pyridylmethyl chloride,
5-fluoro-3-pyridylmethyl chloride,
2-fluoro-5-pyridylmethyl chloride,
1-(2-fluoro-5-pyridyl)ethyl chloride,
2-methyl-1-(2-fluoro-5-pyridyl)propyl chloride,
2-chloro-6-methyl-3-pyridylmethyl chloride,
2,4-dichloro-5-pyridylmethyl chloride,
2,6-dichloro-5-pyridylmethyl chloride,
2,4-dibromo-5-pyridylmethyl chloride,
2,4-difluoro-5-pyridylmethyl chloride,
2-methoxy-3-pyridylmethyl chloride,
2-methoxy-5-pyridylmethyl chloride,
2-ethoxy-5-pyridylmethyl chloride,
2-isopropoxy-5-pyridylmethyl chloride,
2-methylthio-3-pyridylmethyl chloride,
2-methylthio-5-pyridylmethyl chloride,
4-methyl-2-methylthio-5-pyridylmethyl chloride,
2-ethylthio-5-pyridylmethyl chloride,
2-methylsulfinyl-5-pyridylmethyl chloride,
2-methylsulfonyl-5-pyridylmethyl chloride,
4-chloro-2-fluoro-5-pyridylmethyl chloride,
6-chloro-2-methyl-3-pyridylmethyl chloride,
2-chloro-4-methyl-5-pyridylmethyl chloride,
2-allyl-5-pyridylmethyl chloride,
2-propargyl-5-pyridylmethyl chloride,
2,3-dichloro-5-pyridylmethyl chloride,
2-(1-propenyl)-5-pyridylmethyl chloride,
2-chloro-4-pyridylmethyl chloride,
2-fluoro-4-pyridylmethyl chloride,
2,6-dichloro-4-pyridylmethyl chloride,
2,6-difluoro-4-pyridylmethyl chloride,
2-methyl-4-pyridylmethyl chloride,
1-(2-chloro-4-pyridyl)ethyl chloride,
2-chloro-6-methyl-4-pyridylmethyl chloride,
2,6-dimethyl-4-pyridylmethyl chloride,
2-bromo-4-pyridylmethyl chloride,
2,6-dibromo- 4-pyridylmethyl chloride,
3-chloro-2-fluoro-5-pyridylmethyl chloride,
3-bromo-2-fluoro-5-pyridylmethyl chloride,
2-chloro-3-fluoro-5-pyridylmethyl chloride,
3-chloro-2-methylthio-5-pyridylmethyl chloride,
2-ethyl-5-pyridylmethyl chloride,
2-phenyl-5-pyridylmethyl chloride,
2-benzyl-5-pyridylmethyl chloride,
2-phenoxy-5-pyridylmethyl chloride,
2-(2-ethoxyethyl)-5-pyridylmethyl chloride,
2-methoxymethyl-5-pyridylmethyl chloride,
2-difluoromethoxy-5-pyridylmethyl chloride,
2-(2,2,2-trifluoroethoxy)-5-pyridylmethyl chloride,
2-trifluoromethylsulfonyl-5-pyridylmethyl chloride,
2-trifluoromethylsulfinyl-5-pyridylmethyl chloride,
3-furylmethyl chloride,
furfuryl chloride,
5-methylfurfuryl chloride,
2-thienylmethyl chloride,
4-imidazolylmethyl chloride,
4-methyl-5-imidazolylmethyl chloride,
tetrahydrofurfuryl chloride,
5-methyltetrahydrofurfuryl chloride,
3-thienylmethyl chloride,
2-pyrrolylmethyl chloride,
1-methyl-2-pyrrolylmethyl chloride,
5-methyl-2-thienylmethyl chloride,
5-bromo-2-thienylmethyl chloride,
5-cyanofurfuryl chloride,
5-trifluoromethylthio-2-thienylmethyl chloride,
1-(2-thienyl)ethyl chloride,
5-methyl-3-isoxazolylmethyl chloride,
5-isoxazolylmethyl chloride,
4-isoxazolylmethyl chloride,
3-methyl-5-isoxazolylmethyl chloride, 3-trifluoromethyl-5-isoxazolylmethyl chloride,
3-chloro-5-isoxazolylmethyl chloride,
5-isothiazolylmethyl chloride,
5-pyrazolylmethyl chloride,
4-pyrazolylmethyl chloride,
1-methyl-4-pyrazolylmethyl chloride,
1-(1-methyl-4-pyrazolyl)ethyl chloride,
1-ethyl-4-pyrazolylmethyl chloride,
1-isopropyl-4-pyrazolylmethyl chloride,
1-allyl-4-pyrazolylmethyl chloride,
1-tert-butyl-4-pyrazolylmethyl chloride,
1-(2,2,2-trifluoroethyl)-5-pyrazolylmethyl chloride,
3-methyl-5-pyrazolylmethyl chloride,
3-chloro-2-methyl-5-pyrazolylmethyl chloride,
2,3,5-trimethyl-4-pyrazolylmethyl chloride,
5-oxazolylmethyl chloride,
4-methyl-5-oxazolylmethyl chloride,
4-thiazolylmethyl chloride,
5-thiazolylmethyl chloride,
2-methyl-5-thiazolylmethyl chloride,
2-chloro-4-thiazolylmethyl chloride,
2-chloro-5-thiazolylmethyl chloride,
2-trifluoromethyl-5-thiazolylmethyl chloride,
2-bromo-5-thiazolylmethyl chloride,
2,4-dichloro-5-thiazolylmethyl chloride,
4-imidazolylmethyl chloride,
1-methyl-2-imidazolylmethyl chloride,
1,2,4-triazol-5-ylmethyl chloride,
1-methyl-1,2,4-triazol-3-ylmethyl chloride,
1,2,5-thiadiazol-4-ylmethyl chloride,
1,2,3-thiadiazol-5-ylmethyl chloride,
3-methyl-1,2,4-oxadiazol-5-ylmethyl chloride,
1,3-dioxolan-2-ylmethyl chloride,
2,2-dimethyl-1,3-dioxolan-4-ylmethyl chloride,
2-methyl-2-oxazolin-5-ylmethyl chloride,
2-trifluoromethyl-2-oxazolin-5-ylmethyl chloride,
3-pyrrolylmethyl chloride,
1-ethyl-2-pyrrolylmethyl chloride,
1-methyl-3-pyrrolylmethyl chloride,
5-methyl-3-thienyl chloride,
5-methyl-3-pyrrolylmethyl chloride,
1,5-dimethyl-3-pyrrolylmethyl chloride,
2,5-dimethyl-3-furylmethyl chloride,
2,5-dimethyl-3-thienylmethyl chloride,
5-fluoro-3-furylmethyl chloride,
4-chlorofurfuryl chloride,
5-chlorofurfuryl chloride,
5-chloro-3-furylmethyl chloride,
5-chloro-3-thienylmethyl chloride,
5-chloro-1-methyl-3-pyrrolylmethyl chloride,
5-bromo-3-furylmethyl chloride,
5-nitrofurfuryl chloride,
4-nitro-2-thienylmethyl chloride,
5-nitro-2thienylmethyl chloride,
1-methyl-5-nitro-3-pyrrolylmethyl chloride,
5-cyano-3-furylmethyl chloride,
5-cyano-3-thienylmethyl chloride,
5-cyano-1-methyl-3-pyrrolylmethyl chloride,
5-triflurormethylfurfuryl chloride,
5-difluoromethylfurfuryl chloride,
5-trifluoromethyl-3-thienylmethyl chloride,
1-methyl-5-trifluoromethyl-3-pyrrolylmethyl chloride,
5-methoxy-2-thienylmethyl chloride,
5-methylfurfuryl chloride,
2,5-dimethylthio-3-thienylmethyl chloride,
5-trifluoromethylthiofurfuryl chloride,
5-(2,2-dichlorovinyl)-2-thienylmethyl chloride,
5-ethoxycarbonylfurfuryl chloride,
5-formyl-2-thienylmethyl chloride,
3-isoxazolylmethyl chloride,
4-isoxazolylmethyl chloride,
3-ethyl-5-isoxazolylmethyl chloride,
3-isopropyl-5-isoxazolylmethyl chloride,
3-fluoro-5-isoxazolylmethyl chloride,
3-bromo-5-isoxazolylmethyl chloride,
3-hydroxy-5-isoxazolylmethyl chloride,
3-nitro-5-isoxazolylmethyl chloride,
3-cyano-5-isoxazolylmethyl chloride,
3-difluoromethyl-5-isoxazolylmethyl chloride,
3-chlorodifluoromethyl-5-isoxazolylmethyl chloride,
3-methoxymethyl-5-isoxazolylmethyl chloride,
3-isopropoxymethyl-5-isoxazolylmethyl chloride,
3-trichloromethyl-5-isoxazolylmethyl chloride,
3-methoxy-5-isoxazolylmethyl chloride,
3-trifluoromethoxy-5-isoxazolylmethyl chloride,
2,5-dimethyl-4-isoxazolylmethyl chloride,
3-isothiazolylmethyl chloride,
4-isothiazolylmethyl chloride,
3-pyrazolylmethyl chloride,
1-(4-pyrazolyl)ethyl chloride,
1-methyl-3-pyrazolylmethyl chloride,
1-methyl-5-pyrazolylmethyl chloride,
1-propyl-4-pyrazolylmethyl chloride,
1-(2,2,2-trifluoroethyl)-3-pyrazolylmethyl chloride,
5-chloro-1-ethyl-3-pyrazolylmethyl chloride,
5-chloro-1-isopropyl-3-pyrazolylmethyl chloride,
3-chloro-1-methyl-5-pyrazolylmethyl chloride,
5-trifluoromethyl-3-pyrazolylmethyl chloride,
1-methyl-5-trifluoromethyl-3-pyrazolylmethyl chloride,
1-methyl-3-trifluoromethyl-5-pyrazolylmethyl chloride,
4-oxazolylmethyl chloride,
2-methyl-4-oxazolylmethyl chloride,
2-methyl-5-oxazolylmethyl chloride,
2-fluoro-5-oxazolylmethyl chloride,
2-chloro-5-oxazolylmethyl chloride,
2-trifluoromethyl-5-oxazolylmethyl chloride,
2-methylthio-5-oxazolylmethyl chloride,
2-trifluoromethoxy-5-oxazolylmethyl chloride,
2,4-dimethyl-5oxazolylmethyl chloride,
5-ethoxycarbonyl-2-oxazolylmethyl chloride,
1-(5-thiazolyl)ethyl chloride,
2-methyl-4-thiazolylmethyl chloride,
1-(2-methyl-5-thiazolyl)ethyl chloride,
2-ethyl-5-thiazolylmethyl chloride,
2-isopropyl-5-thiazolylmethyl chloride,
4-methyl-5-thiazolylmethyl chloride,
2-fluoro-4-thiazolylmethyl chloride,
2-fluoro-5-thiazolylmethyl chloride,
1-(2-chloro-5-thiazolyl)ethyl chloride,
2-nitro-4-thiazolylmethyl chloride,
2-nitro-5-thiazolylmethyl chloride,
2-cyano-4-thiazolylmethyl chloride,
2-cyano-5-thiazolylmethyl chloride,
2-methylthio-4-thiazolylmethyl chloride,
2-mercapto-5-thiazolylmethyl chloride,
2-methylthio-5-thiazolylmethyl chloride,
2-difluoromethylthio-5-thiazolylmethyl chloride,
2-trifluoromethylthio-5-thiazolylmethyl chloride,
2-chlorodifluoromethylthio-5-thiazolylmethyl chloride,
2-(2,2,2-trifluoroethylthio)-5-thiazolylmethyl chloride,
2-[2-(2,3,3-trichloro)propenylthio]-thiazolylmethyl chloride,
2-thiocyanato-5-thiazolylmethyl chloride,
2-amino-4-thiazolylmethyl chloride, 2-acetamino-4-thiazolylmethyl chloride,
2-methoxy-4-thiazolylmethyl chloride,
2-methoxy-5-thiazolylmethyl chloride,
2-trifluoroethoxy-5-thiazolylmethyl chloride,
2-difluoromethoxy-5-thiazolylmethyl chloride,
2-chloromethyl-5-thiazolylmethyl chloride,
2-difluoromethyl-5-thiazolylmethyl chloride,
2-trifluoromethyl-5-thiazolylmethyl chloride,
2-(1,1,2,2-tetrafluoroethyl)-5-thiazolylmethyl chloride,
2-cyclopropyl-5-thiazolylmethyl chloride,
2-imidazolylmethyl chloride,
1-methyl-5-imidazolylmethyl chloride,
2-fluoro-4-imidazolylmethyl chloride,
2-chloro-4-imidazolylmethyl chloride,
4-nitro-2-imidazolylmethyl chloride,
2-trifluoromethylthio-4-imidazolylmethyl chloride,
1,2-dimethyl-4-imidazolylmethyl chloride,
1-methyl-2-trifluoromethyl-4-imidazolylmethyl chloride,
1-methyl-1,2,3-triazol-4-ylmethyl chloride,
1-(1-methyl-1,2,3-triazol-4-yl)ethyl chloride,
3-methyl-1,2,4-triazol-5-ylmethyl chloride,
3-trifluoromethyl-1,2,4-triazol-5-ylmethyl chloride,
1,2,4-oxadiazol-5-ylmethyl chloride,
1,3,4-oxadiazol-2-ylmethyl chloride,
1,2,3-oxadiazol-5-ylmethyl chloride,
3-trifluoromethyl-1,2,4-oxadiazol-5-ylmethyl chloride,
2- methyl-1,3,4-oxadiazol-5-ylmethyl chloride,
2-trifluoromethyl-1,3,4-oxadiazol-5-ylmethyl chloride,
2-(2,2,2-trifluoroethyl)-1,3,4-oxadiazol-5-ylmethyl chloride,
1,2,4-thiadiazol-5-ylmethyl chloride,
1,2,3-thiadiazol-4-ylmethyl chloride,
1-(1,2,3-thiadiazol-5-yl)ethyl chloride,
1,3,4-thiadiazol-2-ylmethyl chloride,
1-(1,3,4-thiadiazol-2-yl)ethyl chloride,
1,2,5-thiadiazol-3-ylmethyl chloride,
3-methyl-1,2,4-thiadiazol-5-ylmethyl chloride,
4-methyl-1,2,3-thiadiazol-5-ylmethyl chloride,
2-methyl-1,3,4-thiadiazol-5-ylmethyl chloride,
2-trifluoromethyl-1,3,4-thiadiazol-5-ylmethyl chloride,
2-fluoro-1,3,4-thiadiazol-5-ylmethyl chloride,
2-chloro-1,3,4-thiadiazol-5-ylmethyl chloride,
3-chloro-1,2,5-thiadiazol-4-ylmethyl chloride,
1-(3-tetrahydrofuryl)ethyl chloride,
3-tetrahydrothienylmethyl chloride,
1-(3-tetrahydrothienyl)ethyl chloride,
1-methyl-3-pyrrolydinylmethyl chloride,
1,3-oxathiolan-2-ylmethyl chloride,
1,3-dioxolan-4-ylmethyl chloride,
1,3-oxathiolan-4-ylmethyl chloride,
1,3-dithiolan-4-ylmethyl chloride,
thiazolidin-5-ylmethyl chloride,
4-methyl-1,3-dioxolan-2-ylmethyl chloride,
2-methyl -1,3-oxathiolan-4-ylmethyl chloride,
2-chloromethyl-1,3-dioxolan-4-ylmethyl chloride,
2-trifluoromethyl-1,3-dioxolan- 4-ylmethyl chloride,
2-oxo-1,3-dioxolan-4-ylmethyl chloride,
3-formyl-thiazolidin-5-ylmethyl chloride,
3-acetyl-thiazolidin-5-ylmethyl chloride,
3-thiolen-5-ylmethyl chloride,
2H,5H-1,1-dioxo-3-thiolen-3-ylmethyl chloride,
2-isoxazolin-5-ylmethyl chloride,
3-methyl-2-isoxazolin-5-ylmethyl chloride,
3-trifluoromethyl-2-isoxazolin-5-ylmethyl chloride,
3-(2,2,2-trifluoroethyl)-2-isoxazolin-5-ylmethyl chloride,
2,4-dimethyl-2-oxazolin-4-ylmethyl chloride,
2-methyl-1,3-thiazolin-4-ylmethyl chloride,
2-oxazolidon-5-ylmethyl chloride,
3-methyl-2-thiazolidinon-5-ylmethyl chloride,
2-methylamino-5-thiazolylmethyl chloride,
2-trifluoroacetamide-5-thiazolylmethyl chloride,
3-methyl-2-thioxo-thiazolidin-5-ylmethyl chloride,
3-chloro-1,2,4-oxadiazol-5-ylmethyl chloride,
5-carboxy-2-oxazolylmethyl chloride,
2-dimethylamino-5-thiazolylmethyl chloride,
5-phenoxyfurfuryl chloride,
1-phenyl-4-pyrazolylmethyl chloride,
1-benzyl-4-pyrazolylmethyl chloride,
2-phenyl-4-thiazolylmethyl chloride,
1-benzyl-2-imidazolylmethyl chloride,
2-methylsulfinyl-5-thiazolylmethyl chloride,
2-methylsulfonyl-5-thiazolylmethyl chloride,
2-carbamoyl-5-thiazolylmethyl chloride,
2-methylaminocarbonyl-5-thiazolylmethyl chloride,
2-dimethylaminocarbonyl-5-thiazolylmethyl chloride,
5-methylthio-1,3,4-thiadiazol-2-ylmethyl chloride,
5-methylsulfonyl-1,3,4-thiadiazol-2-ylmethyl chloride,
4-pyrimidinylmethyl chloride,
2-methyl-4-pyrimidinylmethyl chloride,
2-methyl-6-oxo-1H,6H-dihydropyrimidin-4-ylmethyl chloride,
5-pyrimidinylmethyl chloride,
2-methyl-5-pyrimidinylmethyl chloride,
2-dimethylamino-5-pyrimidinylmethyl chloride,
2,4,6-trichloro-5-pyrimidinylmethyl chloride,
pyrazinylmethyl chloride,
1-(pyrazinyl)ethyl chloride,
2-methyl-5-pyrazinylmethyl chloride,
3-pyridazinylmethyl chloride,
2-chloro-4-pyrimidinylmethyl chloride,
4-chloro-6-pyrimidinylmethyl chloride,
4-methyl-6-pyrimidinylmethyl chloride,
2-fluoro-5-pyrimidinylmethyl chloride,
1-(2-fluoro-5-pyrimidinyl)ethyl chloride,
2-chloro-5-pyrimidinylmethyl chloride,
2-isopropyl-5-pyrimidinylmethyl chloride, or bromide,
2-chlorodifluoromethyl-5-pyrimidinylmethyl chloride,
2-trifluoromethyl-5-pyrimidinylmethyl chloride,
2-bromodifluoromethyl-5-pyrimidinylmethyl chloride,
2-methoxy-5-pyrimidinylmethyl chloride,
2-difluoromethoxy-5-pyrimidinylmethyl chloride,
2-trifluoromethoxy-5-pyrimidinylmethyl chloride,
2-(2,2,2-trifluoroethoxy)-5-pyrimidinylmethyl chloride,
2-methylthio-5-pyrimidinylmethyl chloride,
2-ethylthio-5-pyrimidinylmethyl chloride,
2-difluoroethylthio-5-pyrimidinylmethyl chloride,
2-trifluoromethylthio-5-pyrimidinylmethyl chloride,
2-nitro-5-pyrazinylmethyl chloride,
2-cyano-5-pyrazinylmethyl chloride,
2-chloro-5-pyrazinylmethyl chloride,
2-trifluoromethyl-5-pyrazinylmethyl chloride,
3-fluoro-6-pyridazinylmethyl chloride,
3-methyl-6-pyridazinylmethyl chloride,
4-pyridazinylmethyl chloride,
3-chloro-6-pyridazinyl methyl chloride,
4-pyridazinylmethyl chloride,
3-trifluoromethyl-6-pyridazinylmethyl chloride,
1,3,5-triazin-2-ylmethyl chloride,
3-chloro-1,2,4-triazin-6-ylmethyl chloride,
3,5-dichloro-1,2,4-triazin-6-ylmethyl chloride, and
3-chloro-1,2,4,5-tetrazin-6-ylmethyl chloride.

In place of the chlorides hereinabove, the bromides or the p-toluensulfonates may also be exemplified. They will be specifically described below.

The halides hereinabove, for instance the chlorides, can be produced without difficulty by chlorination of the corresponding alcohols with thionylchloride.

For instance, 2-chloro-5-pyridylmethylchloride can be obtained by chlorination of 2-chloro-5-pyridylmethylalcohol with thionylchloride. (see J. Org. Chem., vol. 34, 3547).

The bromides may also be produced by bromination of a methyl group side-chain with N-bromosuccinimide.

Some of trifluoromethyl-substituted or trifluoromethoxy-substituted pyridyl alcohols are described in J. Med. Chem., vol. 13, pages 1124–1130. By using these synthesizing techniques, 2-methyl-5-trifluoromethyl pyridine obtained by reaction of 6-methylnicotinic acid with hydrofluoric acid and sulfur tetrafluoride is converted to an N-oxide, and the rearrangement reaction of the N-oxide can give 5-trifluoromethyl-2-pyridylmethyl alcohol.

This reaction can also be applied to the synthesis of 5-methyl-2-trifluoromethylpyridine from 5-methylpicolic acid. 2-Trifluoromethyl-5-pyridylmethyl bromide (or chloride), the desired starting substance, can be synthesized by mono-halogenating the aforesaid 5-methyl-2-trifluoromethylpyridine with N-bromosuccinimide or N-chlorosuccinimide.

2-Trifluoromethoxy-5-pyridylmethyl bromide (or chloride) can similarly be obtained by reacting 5-methyl-2-trifluoromethoxypyridine obtained from 2-hydroxy-5-methylpyridine, with N-bromosuccinimide or N-chlorosuccinimide.

Since the halogen at the ortho-position of the pyridine ring is active, a 2-haloalkoxy-5-pyridylmethyl alcohol can be synthesized, for example, by the reaction of 6-chloronicotinic acid with an excess of a sodium alkoxide. Reduction of this compound can give the starting 2-haloalkoxy-5-pyridylmethyl alcohol.

Halogenomethyl-substituted furans and thiophenes are known compounds. For example, 2-ethoxycarbonyl-5-chloromethylfuran is a known compound described in Liebigs Annalen der Chemie, Vol. 580, page 176. 2-Bromomethyl-5-trifluoromethylfuran is obtained by halogenating the side-chain of 2-methyl-5-trifluoromethylfuran with a-halogenating agent such as N-bromosuccinimide (NBS) (U.S. Pat. No. 3,442,913).

Many bromomethyl-substituted heterocyclic compounds can be obtained by brominating the corresponding methyl-substituted heterocyclic compounds with N-bromosuccinimide.

Halogenomethyl-substituted isoxazoles can be obtained by halogenating methylisoxazole with NBS, etc. or hydroxymethyl isoxazole can be easily converted to chloromethyl isoxazole by thionyl chloride. For example, 5-bromomethyl isoxazole is a compound described in German Offenlegungsschrift No. 2,716,687, and 4-bromomethylisoxazole is a compound described in Chem. Abst., Vol. 65, 2242h.

Chloromethyl-substituted heterocyclic compounds can be synthesized by chloromethylation reaction. 4-chloromethyl isoxazole and 4-chloromethyl-3,5-dimethylisoxazole described in Zh. Obshch. Khim., Vol. 34, pages 4010–4015 are good examples thereof. Furthermore, halogenomethyl-substituted isoxazoles can also be synthesized by direct ring synthesis. 3-Bromo-5-bromomethylisoxazole (Rend. Ist. Lombardo Sci. Pt. I. Classe Sci. Mat. e Nat., Vol. 94, paces 729–740, and 5-bromomethyl-3-methylisoxazole (Japanese Laid-Open Patent Publication No. 59156/1977) are good examples thereof.

5-Chloromethyl-3-trifluoromethyl isoxazole can be obtained by synthesizing 3-trifluoromethyl-5-hydroxymethyl isoxazole, and chlorinating it with thionyl chloride in accordance with the description of Bull. Chem. Soc. Japan, Vol. 57, pages 2184–2187. The use of other halogenoalkyls instead of trifluoromethyl in the above reaction can lead to the synthesis of the corresponding halogenoalkyl isoxazoles. As stated above, halogenoalkyl heterocyclic compounds can be easily obtained generally by treating the corresponding alcohols with halogenating agents typifies by thionyl chloride.

5-Chloromethyl-3-hydroxyisoxazole is synthesized in accordance with the description of Tetrahedron Letters, 1965, No. 25, pages 2077–2079. Chlorination of it with phosphonyl chloride, etc., can give 3-chloro-5-chloromethyl isoxazole.

Halogen-substituted halogenomethyl-substituted isothiazoles can be obtained, for example, by converting halogen-substituted methyl-substituted isothiazoles with halogenating agents such as NBS into halogen-substituted bromomethyl-substituted isothiazoles. 5-Bromo-3-bromomethylisothiazole (described in J. Chem. Soc., 1965. pages 7274–7276) is a good example.

4-Chloromethylpyrazole can be easily obtained by chlorinating 4-hydroxymethylpyrazole with thionyl chloride (J. A. C, S., Vol. 71, pages 3994–4000).

As regards halogeno-halogenomethylpyrazoles, 3-ethoxycarbonyl-5-hydroxy-1-methylpyrazole, for example, is synthesized in accordance with the description of Chem. Pharm. Bull., Vol. 31, No. 4, pages 1228–1234. Subsequent chlorination with phosphonyl chloride gives 5-chloro-1-methyl-3-pyrazolylcarbonyl chloride. Reduction of the chloride with sodium borohydride gives 5-chloro-3-hydroxymethyl-1-methylpyrazole.

Chlorination of this product in a customary manner can give 5-chloro-3-chloromethyl-1-methylpyrazole.

With regard to halogenomethyl-substituted oxazoles, chlorination of hydroxymethyloxazole with thionyl chloride, etc., can give chloromethyl oxazole. They can also be synthesized by direct ring synthesis.

For example, 5-bromomethyl-2-methyloxazole is a known compound (J. A. C. S., Vol. 104, pages 4461–4465) and 2-bromoethyl-5-ethoxycarbonyloxazole is also a known compound (Japanese Laid-Open Patent Publication No. 108771/1984).

4-Halogenomethylthiazoles can be directly synthesized, for example, by reacting dihalogenoacetones with thioacylamides such as thioacetamide (J. A. C. S., Vol. 56, pages 470–471, and ibid., Vol. 73, page 2936).

5-Halogenomethylthiazoles can be obtained by reacting a thioacylamide pith alpha-chloro-alpha-formylethyl acetate, reducing the resulting 5-ethoxycarbonylthiazole with lithium aluminum hydride in a customary manner, and halogenating the resulting 5-hydroxymethylthiazole. 5-Chloromethyl-2-methylthiazole described in Zh. Obshch. Khim., Vol. 32, pages 570–575 and J. A. C. S., Vol. 104, pages 4461–4465 is a good example.

Reaction of thiourea instead of the thioacylamide can give 2-amino-4-chloromethyl- or 2-amino-5-chloromethyl thiazole, and via diazotization, a halogen atom, etc., can further be introduced. This halogen is active and can be converted to a 2-alkoxy group by a sodium alkoxide (Japanese Laid-Open Patent Publication No. 5972/1979 and J. Chem. Soc., Perkin I, 1982, pages 159–164).

2-Halogeno-4- or 5-bromomethylthiazole can be synthesized by brominating 2-halogeno-4- or 5-methylthiazoles with NBS.

The use of ammonium dithiocarbamate (Org. Synthesis, Coll. Vol. III, page 763) instead of the thioacetamide above can give 4- or 5-halogenomethyl-2-mercaptothiazoles. Alkylation or haloalkylation can give 2-alkylthio-4- or 5-halogenomethylthiazoles, or 2-substituted alkylthio-4- or 5-halogenomethylthiazoles (J. A. C. S., Vol. 75, pages 102–103).

A halogenomethyl imidazole, for example, chloromethylimidazole, can be obtained by hydroxymethylating an N-alkylimidazole with formaldehyde, optionally dealkylating it to form hydroxyethylimidazole, and chlorinating it with thionyl chloride, etc.,in a customary manner (described in J. A. C. S., Vol. 71, pages 383–386). 4-Hydroxymethylimidazole as one example of the hydroxymethyl imidazole, can be directly synthesized from fructose, formaldehyde and ammonia (described in Org. Synthesis Coll., Vol. III, page 460).

Hydroxymethyltriazole can be synthesized, for example, in accordance with the procedure described in J. A. C. S., Vol. 77, pages 1538–1540, and chlorination of it can give chloromethyltriazole.

Halogenomethyloxadiazoles and halogenomethylthiazoles can be synthesized respectively by brominating methyl-substituted oxazole and methyl-substituted thiazole with NBS. 3-Bromomethyl-1,2,5-thiadiazole described in Japanese Laid-Open Patent Publication No. 24963/1974 and 3-bromomethyl-4-chloro-1,2,5-thiadiazole are good examples thereof. The halogenomethyl oxadiazoles and halogenomethylthiadiazoles can be synthesized by direct ring synthesis. For example, 5-chloro-3-chloromethyl-1,2,4-thiadiazole described in J. Org. Chem, Vol. 27, pages 2589–2592, 3-chloro-5-chloromethyl-1,2,4-oxadiazole described in West German OLS No. 2,054,342, and 5-chloromethyl-3-methyl-1,2,4-oxadiazole described in Bull. Soc. Chim. Belges., Vol. 73, paces 793–798 are good examples thereof. The 2-position substituted 5-chloromethyl -1,3,4-oxa(or thia)diazole described in French Patent No. 1,373,290) is another good example.

Chloromethyl-substituted heterocyclic compounds can be synthesized by reducing carboxylic acids or ester derivatives thereof with lithium aluminum hydride, etc. to convert them to alcohol derivatives, and further chlorinating the alcohol derivatives with thionyl chloride, etc. As examples thereof, Japanese Laid-Open Patent Publication No. 89633/1984 describes 5-chloromethyl-1,2,3-thiadiazole, 4-chloromethyl-1-methyl-1,2,3,5-tetrazole and 4-chloromethyl-1-methyl-1,2,3-triazole.

Halogenoalkyl-substituted, saturated or partially unsaturated heterocyclic compounds can be converted to chloromethyl-substituted products by, for example, chlorinating their alcohol derivatives in a customary manner.

Bromomethyldioxolane and bromomethyloxothiolane can be synthesized by reacting dimethyl bromoacetal with ethylene glycol, or reacting dimethyl bromoacetal with 2-mercaptoethanol or reacting an aldehyde or ketone with epibromohydrin. For example, 2-bromomethyl-1,3-dioxolane is described in Beilstein, Vol. 19, II, page 8.

As regards chloromethyl-substituted oxazoline compounds, 5-chloromethyl-3-methyl-2-isoxazoline can be synthesized in accordance with the description of Pak. J. Sci. Res., Vol. 30, pages 91–94. 5-Chloromethyl-3-trifluoromethyl-2-isoxazoline may be synthesized by chlorinating 3-trifluoromethyl-5-hydroxymethyl-2-isoxazoline described in Bull. Chem. Soc. Japan, Vol. 57, pages 2184–2187 in a customary manner. 5-Chloromethyl-2-methyl-oxazoline is a compound described in Tetrahedron, Vol. 34, pages 3537–3544.

4-Chloromethyl-2-methyl-2-thiazoline can be synthesized by chlorinating 4-hydroxymethyl-2-methyl-2-thiazoline described in Heterocycles, Vol. 4, pages 1687–1692. 5-Chloromethyl-3-methyl-oxazolidin-2-one is a compound described in West German OLS No. 1,932,219. 3-Bromomethyl-1,1-dioxo-3-thiolene is a compound described in U.S. Pat. No. 4,561,764 and can be synthesized by bromination with NBS.

5-Pyrimidinylmethyl alcohol is obtained from 5-pyrimidinecarbaldehyde, and 2-chloro-5-pyrimidinylmethyl alcohol, from 2-chloro-5-pyrimidinecarbaldehyde. 3-Pyridazinylmethyl alcohol can be synthesized from furfuryl acetate (Acta Chem. Scand. vol. 1, page 619). With regard to pyrazinyl alkyl halides, methylpyrazine or dimethylpyrazine which is easily available can be converted to chloromethylpyrazine by using N-chlorosuccinimide (Synthesis, 1984, pages 676–679). This reaction can be applied to methylpyrazines having other substituents and halo-substituted methylpyridazines such as 3-chloro-6-methylpyridazine (described in J. Chem. Soc., 1947, page 242), and by this reaction 3-chloro-6-pyridazinylmethyl chloride can be synthesized. Furthermore, 2-chloro-5-pyrimidinylmethyl bromide can be obtained from 2-chloro-5-methylpyrimidine (Reacts. Sposobnost. Org. Soedin., vol. 5, pages 624–837) and N-bromosuccinimide.

As described in J. Hetrocycl. Chem., vol. 19, page 407 and Chem. Pharm. Bull. , vol. 28, pages 3057 and 3063, ethyl 2-chloropyrazine-5-carboxylate can be synthesized, and reduced to the corresponding methanol 2,910,824).

As regards triazinyl alkyl halides, 2,5-triazin-2-ylmethyl chloride, for example, can be obtained by reacting 2-methyl-1,3,5-triazine with N-chlorosuccinimide (J. Org. Chem., vol. 29, pages 1527–1537). 3,5-Dichloro-6-methyl-1,2,4-triazine (described in J. Med. Chem., vol. 10, pages 883–887) and 3-chloro-6-methyl-1,2,4,5-tetrazine (J. Org. Chem., vol. 46, pages 5102–5109) can be chlorinated similarly by reaction with N-chlorosuccinimide.

In the formula (I) in which X is

or Y is

and which can be obtained by the above process (a), (b), (c), (d), (e) or (f), each hydrogen atom of the

group and the

group thereof may be substituted by or added to other groups.

As specific examples, some compounds having active olefinic linkage, such as methylvinylketone, ethylacrylate, and acrylonitrile can be reacted with the =CH— group by Michael type addition. (see Japanese Laid-Open Patent Application No. 151,882/1975).

Moreover, by Mannich reaction and others similar thereto, specifically, a dialkylaminomethyl group can be introduced to α-carbon atom of the nitromethylene group, and also active aldehydes such as formaldehyde and chloral may be added as well. (see Japanese Laid-Open Patent Application No. 151,882/1975)

In addition, each hydrogen atom of the above

group and

group can also be halogenated by a halogenating agent such as N-chlorosuccinimide, N-bromosuccinimide, perchloryl fluoride and halogen per se. (see U.S. Pat. Nos. 3,933,809 and 3,962,233, Japanese Laid-Open Patent Application No. 54,532/1974).

In the above cases, the formula (I) may have the following formula:

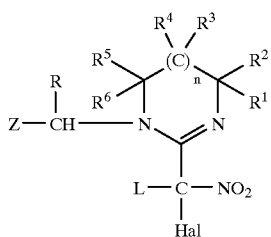

wherein
n, $R^1$, $R^2$, $R^3$, $R^4$, $R^5$, $R^6$, R, Z and Hal have the same meanings as stated above, and L represents a halogen atom, a phenylthio group or an alkoxycarbonyl group.

Glyoxalic acid and dimethylformaldehydedimethylacetal can also be reacted with α-carbon atom of the nitromethylene group, and said formula,(I) may have the following formula:

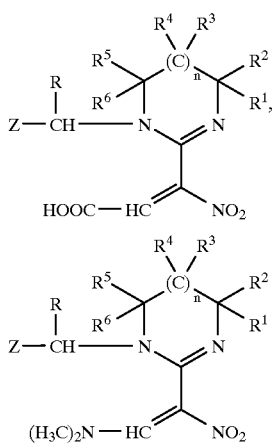

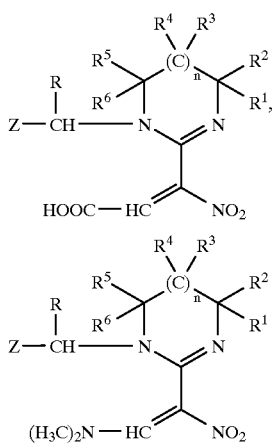

wherein
n, $R^1$, $R^2$, $R^3$, $R^4$, $R^5$, $R^6$, R and Z have the same meanings as stated above.

The nitrogen atom of the above

group and α-carbon atom of the nitromethylene group can independently be acylated, sulfenylated or sulfonylated. (see Netherland Patent No. 7,306,145, U.S. Pat. Nos. 3,985,736, 3,996,372, 4,020,061, 4,022,775, 4,052,411, 4,053,662 and 4,076,813).

Acylisocyanates and sulfonylisocyanates can be reacted with α-carbon atom of the nitromethylene group. (see U.S. Pat. Nos. 4,013,766, 4,025,634, 4,029,791 and 4,034,091).

The nitrogen atom of the above

group can also be alkylated (see Belgian Patent No. 321, 282) and by using said reaction, third-position of the imidazolidines or the tetrahydropyrimidines can be alkylated to obtain the corresponding formula (I).

In carrying out the process (a), suitable diluents may be all inert organic solvents.

Examples of such diluents include water; aliphatic, alicyclic and aromatic hydrocarbons (which may optionally be chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, diisopropyl ether, dibutyl ether, propylene oxide, dioxane and tetrahydrofuran; nitriles such as acetonitrile, propionitrile and acrylonitrile; alcohols such as methanol, ethanol, isopropanol, butanol and ethylene glycol; acid amides such as dimethylformamide and dimethylacetamide; sulfones and sulfoxides such as dimethyl sulfoxide and sulfolane; and bases such as pyridine.

The process (a) can be carried out over a wide temperature range. Generally, it can be carried out at a temperature between about –20° C. and the boiling point of the mixture, preferably between about 50° C. and about 120° C. Desirably, the reaction is carried out under normal atmospheric pressure, but it is also possible to operate under elevated or reduced pressures.

In the process (a), the desired novel compounds of the formula (I) can be obtained, for example, by reacting the compounds of the formula (II) with 1 to about 1.2 moles, preferably 1 to about 1.1 moles, per mole of the compounds of the formula (II), of the compounds of the formula (III) in an inert solvent such as an alcohol (e.g., methanol or ethanol) until the generation of mercaptan ceases.

In carrying out the processes (b) and (c), suitable diluents may be the above inert solvents exemplified for the process (a). As the base, for example, hydroxides, carbonates, bicarbonates and alcoholates of alkali metals, and tertiary amines such as triethylamine, diethylamine and pyridine may also be cited.

The processes (b) and (c) can be carried out over a broad temperature range, generally between about –20° C. and the boiling paint of the mixture, preferably between about 0° C. and about 50° C.

The reaction is carried out preferably under normal atomospheric pressure, but it is also possible to perform it under elevated or reduced pressure.

In the above processes (b) and (c), for example, about 1 to about 5 moles preferably about 2 to about 4 moles, of a base and about 0.9 to about 4 moles preferably about 1 to about 3 moles, of the compounds of the formulae (IV) or (V) can be used, per mole of the compounds of the formula (II).

In carrying out process (d), suitable diluents may be the above inert solvents exemplified for the process (a).

According to process (d), the desired compounds of the formula (I) can be easily obtained, for example, by reacting 1 mole of the compounds of the formula. (II) with 1 to about 1.2 moles, preferably 1 to about 1.1 moles, of nitroguanidine under heat in a water solvent.

The process (b) can be carried out at a temperature of, for example, about 0° C. to about 100° C., preferably about 30° C. to about 80° C. The reaction is preferably carried out under normal atmospheric pressure, but can also be carried out under elevated or reduced pressures.

In the practice of process (e), the compounds of the formula (VI) is usually dissolved in an acid such as conc. sulfuric acid prior to the reaction.

In carrying out the processes, the compounds of the formula (VI) and fuming nitric acid (with a purity of at least 98%) are reacted at low temperatures, preferably about 0° C. or lower to obtain the desired compounds of the formula (I) (by applying the method of British Patent Application No. 2,055,796).

The compound of general formula (VI) used in the above process is generally present in the form of a hydrohalide as a result of its synthesis as stated above, and usually it is neutralized in a customary manner before using it in the process (e).

In the practice of the process (f), suitable diluents may be the above inert organic solvents exemplified for the process (a). As the bases, for example, hydrides such as sodium hydride and potassium hydride, hydroxides and carbonates of alkali metals may also be cited.

The process (f) can be carried out over a broad temperature range, generally between about 0° C. and about 100° C., preferably betwen about 10° C. and about 80° C.

The reaction (f) is carried out preferably under normal atmospheric pressure, but it is also possible to perform it under elevated or reduced pressure.

In the process (f), the desired compounds of the formula (I) can be obtained, for example, by reacting the compounds of the formula (VII), in the presence of about 1.1 to 1.2 moles, per mole of the compound (VII), of sodium hydride as a base, with 1 to about 1.2 moles preferably 1 to about 1.1 moles, per mole of the compound (VII), of the compounds of the formula (VIII) in an inert solvent such as dimethylformamide. In the process (f), it is preferable for the reaction that the compound of general formula (VII) be converted in advance into its sodium salt by using sodium hydride. In view of the characteristics of sodium hydride, such a reaction is desirably carried out under a nitrogen gas atmosphere.

The compounds of the formula (I) in accordance with this invention include a tautomer as shown by the following formula.

In the case of X being NH and Y being CH,

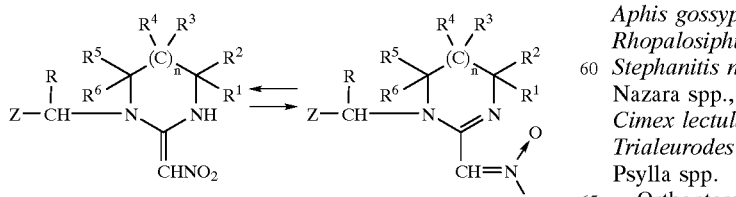

In the case of X being NH and Y being N,

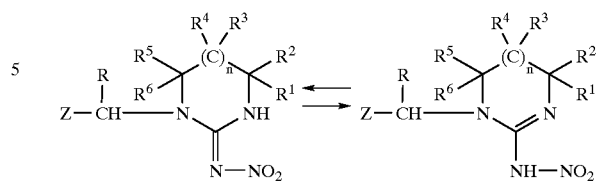

In addition, where Y is C-R⁹, the corresponding formula (I) may include E,Z-isomer.

The compounds of the formula (I) may also be present in the form of a salt. Examples of the salt are inorganic acid salts, sulfonate salts, organic acid salts and metal salts.

The active compounds according to the invention exhibit powerful insecticidal effects.

They can, therefore, be used as insecticides. The active compounds can be used for control and eradication of a wide range of pests, including sucking insects, bitting insects and other plant parasites, pests on stored grains and pests causing health hazards.

Examples of the pests are shown below.

Coleopterous insects
*Callosobruchus chinensis,*
*Sitophilus zeamais,*
*Tribolium castaneus,*
*Epilachna vigitoctomaculata,*
*Agriotes fuscicollis,*
*Anomala rufocuprea,*
*Leptinotarsa decemkineata,*
Diabrotica spp.,
*Monochamus alternatus,*
*Lissorhoptrus oryzophilus,* and
*Lyctus brunneus.*

Lepidopterous insects
*Lymantria dispar,*
*Malacosoma neustria,*
*Pieris rapae,*
*Spodoptera litura,*
*Mamestra brssicae,*
*Chilo suppressalis,*
*Pyrausta nubilalis,*
*Ephestia cautella,*
*Adoxophyes orana,*
*Carpocapsa pomonella,*
*Agrotis fucosa,*
*Galleria mellonella,*
*Plutella maculipennis,* and
*Phyllocnistis citrella.*

Hemipterous insects
*Nephotettix cincticeps,*
*Nilaparvata lugens,*
*Pseudococcus cometocki,*
*Unaspis yanonensis,*
*Myzus persicae,*
*Aphis pomi,*
*Aphis gossypii,*
*Rhopalosiphum pseudobrassicas,*
*Stephanitis nashi,*
Nazara spp.,
*Cimex lectularius,*
*Trialeurodes vaporariorum,* and
Psylla spp.

Orthopterous insects
*Blatella germanica,*
*Periplaneta americana,*

*Cryllotalpa africana,* and
*Locusta migratoria migratoriodes.*
Isopterous insects
*Deucotermes speratus,* and
*Coptotermes formosanus.*
Dipterous insects
*Musca domestica,*
*Aedes aegypti,*
*Hylemia platura,*
*Culex pipens,*
*Anopheles sinensis,* and
*Culex tritaeniorhynchus.*

In the field of veterinary medicine, the novel compounds of this invention are effective against various noxious animal parasites (endo- and ecto-parasites) such as insects and worms. Examples of such animal parasites are shown below.
Insects
Gastrophilus spp.,
Stomoxys spp.,
Trichodectes spp.,
Rhodnium spp., and
*Ctenocephalides canis.*

Substances having pesticidal activity against all of these pests may sometimes be referred to in this application simply as insecticides.

The active compounds can be converted into the customary formulations, such as solutions, emulsions, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamnide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as hyghly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 per cent by weight of active compound, preferably from 0.5 to 90 per cent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agent are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The following examples illustrate the present invention specifically. It should be noted, however, that the invention is not limited to them alone.

PREPARATIVE EXAMPLES

Example 1

(compound No. 1)

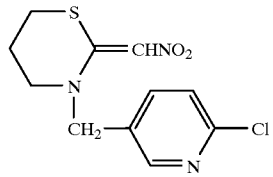

A mixture of N-(2-chloro-5-pyridylmethyl)3-aminopropanethiol (4.3 g), -nitro-2,2-bis(methylthio)

ethylene (3.3 g) and ethanol (40 ml) was heated under reflux or 10 hours in a stream of nitrogen. Aster the reaction, about ⅔ of ethanol was distilled off under reduced pressure. Ether was added little by little to the reaction mixture to precipitate crystals. The crystals were collected by filtration, and washed with a mixture of ethanol and ether to give the desired 3-(2-chloro-5-pyridymethyl)-2-nitromethylenetetrahydro-2H-1,3-thiazine (1.3 g) as yellow crystals.

m.p. 164–166° C.

Example 2

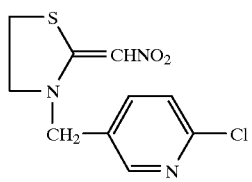

(compound No. 2)

2-Nitromethylenethiazolidine (2.9 g) was dissolved in dry acetonitrile (30 ml), and 60% sodium hydride (0.9 g) was added at room temperature in a stream of nitrogen. Subsequently, the mixture was stirred at room temperature until the generation of hydrogen ceased. Then, a solution of 2-chloro-5-pyridylmethyl chloride (3.2 g) in dry acetonitrile (5 ml) was added at room temperature, and the mixture was stirred at room temperature for 1 day. Acetonitrile was then distilled off under reduced pressure, and dichloromethane was added to the residue. The mixture was then washed with water. Dichloromethane was distilled off from the dichloromethane layer. The remaining oil was purified by silica gel column chromatography to give the desired 3-(2-chloro-5-pyridylmethyl)-2-nitromethylenethiazolidine (1.6 g).

mp. 177–179° C.

Example 3

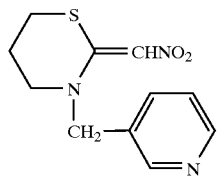

(compound No. 3)

A mixture of N-(3-pyridylmethyl)3-aminopropanethiol (1.8 g), 1-nitro-2,2-bis(methylthio)ethylene (1.7 g) and ethanol (40 ml) was heated under reflux for 5 hours under a nitrogen stream. After the reactions about ⅔ by volume of ethanol was distilled off under reduced pressure. Ether was added little by little to the reaction mixture to precipitate crystals. The crystals were collected by filtration, and washed with a mixture of ethanol and ether to give the desired 3-(3-pyridylmethyl) 2-nitromethylenetetrahydro-2H-1,3-thiazine (1.2 g).

mp. 143–146° C.

Example 4

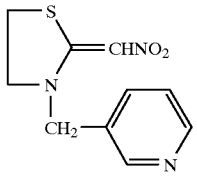

(compound No. 4)

2-Nitromethylenethiazolidine (2.9 g) was suspended in dry acetonitrile (30 ml), and 60% sodium hydride (0.9 g) was added under a nitrogen stream. Then, the mixture was stirred at room temperature until the generation of hydrogen ceased. A solution of 3-picolyl chloride (3.2 g) in dry acetonitrile (5 ml) was added, and the mixture was stirred at room temperature for 3 hours. Acetonitrile was distilled off under reduced pressure. Dichloromethane was added to the residue, and the mixture was washed with water. Dichloromethane was then distilled off from the dichloromethane layer. The remaining oily product was purified by column chromatography to give the desired 3-(3-pyridylmethyl)2-nitromethylenethiazolidine (0.5 g).

mp. 96–100° C.

Example 5

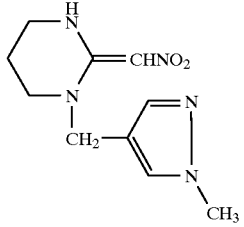

(compound No. 5)

A mixture of 16.8 g of N-(1-methyl-4-pyrazolylmethyl)-trimethylenedianine, 16.5 g of 1-nitro-2,2-bis(methylthio)ethylene and 200 ml of ethanol was heated under reflux until the generation of methylmercaptan ceased. The mixture was cooled, and the precipitated crystals were collected by filtration. Washing with methanol gave 16.6 g of the desired 1-(1-methyl-4-pyrazolylmethyl)2-(nitromethylene)tetrahydropyrimidine as pale yellow crystals.

mp. 186–190° C.

Example 6

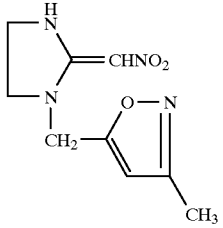

(compound No. 6)

A mixture of 15.5 g of N-(3-methyl-5-iso-xazolylmethyl)-ethylenedamine, 16.5 g of 1-nitro-2,2-bis(methylthio) ethylene and 200 ml of ethanol was heated under reflux until the generation of methylmercapan ceased. The period of about 3 hours was required. Then, the reaction mixture was cooled to room temperature, whereupon the desired product precipitated as crystals. The crystals were collected by filtration and washed with ethanol to give 12.5 g of 1-(3-methyl-5-isoxazolylmethyl)2-(nitromethylene)imidazolidine as yellow crystals.

mp. 168–170° C.

Example 7

(compound No. 7)

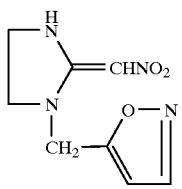

2-Nitromethylene imidazolidine (12.9 g) was dissolves in 60 ml of dry dimethylformamide, and 4.4 g of 60% sodium hydride was added little by little in a nitrogen stream at room temperature, and successively, the mixture was stirred at room temperature to 30° C. for 3 hours to form the sodium salt of the imidazolidine compound. Then, 11.8 g of 5-isoxazolylmethyl chloride was added at room temperature, and the mixture was stirred at room temperature for 24 hrs. The reaction mixture was carefully poured into 150 ml or ice water and extracted twice with dichloromethane. Dichloromethane was distilled off from the dichloromethane layers to give 12 g of the desired 1-(5-isoxazolylmethyl)2-(nitromethylene)imidazolidine as brown crystals.

mp. 156–158° C.

Example 8

(compound No. 8)

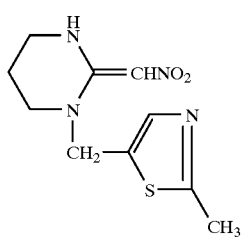

N-(2-Methyl-5-thiazolylmethyl)trimethylenediamine (18.5 g) was dissolved in 100 ml of acetonitrile, and 1-nitro-2,2-bis(methylthiio)ethylene (16.5 g) was added. With stirring, the mixture was refluxed for 6 hours. After the reaction, the reaction mixture was cooled to room temperature. The resulting crystals were collected by filtration and washed with methanol to give 10.2 g of the desired 1-(2-methyl-5-thiazolylmethyl)2-(nitromethylene)tetrahydropyrimidine.

mp. 204–207° C.

Example 9

(Compound No. 9)

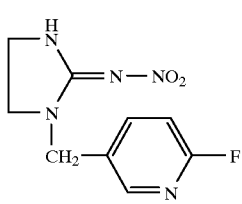

A mixture of 2-fluoro-5-pyridylmethyl bromide (9.5 g), 2-(nitroimino)imidazolidine (6.5 g), potassium carbonate (7.6 g) and acetonitrile (100 ml) was refluxed for 2 hours with stirring. After the reaction, the reaction mixture was cooled to room temperature, and cold water (100 ml) was added. The resulting crystals were collected by filtration and washed with ether to give slightly colored 1-(2-fluoro-5-pyridylmethyl)-2-(nitroimino)imidazolidine (6.0 g) as the desired compound.

mp. 121–124° C.

Example 10

(Compound No. 10)

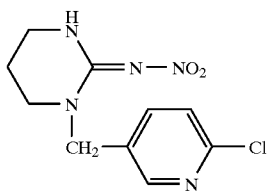

A solution composed of N-(2-chloro-5-pyridylmethyl)trimethylenediamine (10 g), nitroguanidine (5.7 g) and water (80 ml) was heated at 80° C. for 3 hours. The reaction mixture was cooled to room temperature, and extracted twice with 50 ml of dichloromethane. Dichloromethane was distilled off from the extracts, and the tarry residue was purified by silica gel column chromatography to give almost colorless 1-(2-chloro-5-pyridylmethyl)-2-(nitroimino)tetrahydropyrimidine (6.1 g).

mp. 113–117° C.

Example 11-i

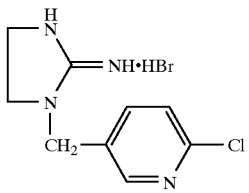

A solution of N-(2-chloro-5-pyridylmethyl)ethylenediamine (18.6 g) in toluene (200 ml) was stirred at room temperature, and cyanogen bromide (10.6 g) was added portionwise. Then, the mixture was further stirred. Since the desired 1-(2-chloro-5-pyridylmethyl)-2-iminoimidazolidine precipitated as a hydrobromide, the reaction mixture was filtered and the filtrate was washed with ether.

mp. 202–205° C.

Example 11-ii (Compound No. 11)

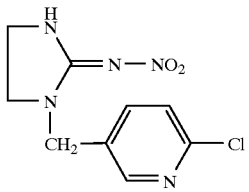

The hydrobromide (5.8 g) synthesized in Example 11-i was added to 98% sulfuric acid (30 ml) at 0° C. Then, with stirring, 2 ml of fuming nitric acid was added dropwise at 0° C. After the addition, the mixture was stirred at 0° C. for 2 hours. The reaction mixture was poured into ice water (100 g) and extracted with dichloromethane. Dichloromethane was distilled off from the extract under reduced pressure to give pale yellow crystals. The crystals were washed with ether to give 1-(2-chloro-5-pyridylmethyl)-2-(nitroimino) imidazolidine (1.5 g).

mp. 136–139° C.

Example 12

(Compound No. 12)

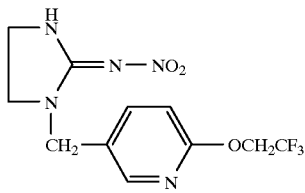

Sodium hydride (0.48 g) was added to a solution of 2,2,2-trifluoroethanol (2.4 g) in toluene (30 ml) was added, and the mixture was stirred until the generation of hydrogen ceased. As a result, 2,2,2-trifluoroethanol sodium salt was prepared. To the product were added 1-(2-chloro-5-pyridylmethyl)-2-(nitroimino)imidazolidine (5.1 g) synthesized by the method of Example 3 and a catalytic amount of 4-dimethylaminopyridine. The mixture was heated at 80° C. for 10 hours with stirring. After cooling the reaction mixture, the precipitated crystals were collected by filtration, washed with water and ether and then purified by silica gel chromatography to give 1-[2-(2,2,2-trifluoroethoxy)-5-pyridylmethyl]-2-(nitroimino)imidazolidine (1.5 g).

mp. 109–112° C.

Example 13

(Compound No. 13)

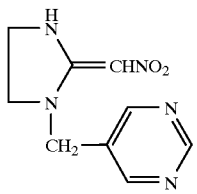

A mixture of N-(5-pyrimidinylmethyl)ethylenediamine (15.2 g), 1-nitro-2,2-bis(methylthio)ethylene (14.9 g) and ethanol (100 g) was refluxed with stirring until the generation of methylmercaptan ceased (for about 3 hours). The reaction mixture was cooled to room temperature, and the resultant crystals were collected by filtration. The crystals were washed with ethanol, and dried to give 1-(5-pyridylmethyl)-2-(nitromethylene)imidazolidine (12.7 g) as pale yellow crystals. This product decomposes at 236° C.

Example 14

(Compound No.14)

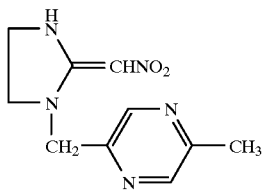

2-Nitromethyleneimidazolidine (12.9 g) was dissolved in dry dimethylformamide (100 ml), and at room temperature 60% oily sodium hydride (4.4 g) was added. The mixture was stirred at room temperature until the generation of hydrogen ceased. Then, 2-methyl-5-pyrazinylmethyl chloride (14.3 g was added at room temperature, and the mixture was stirred at 40° C. for 8 hours. After cooling to room temperature, the reaction mixture was added to 200 ml of water, and extracted with dichloromethane. On distilling off dichloromethane from the organic layer under reduced pressure, 1-(2-methyl-5-pyrazinylmethyl)-2-(nitromethylene)imidazolidine (5.4 g) was obtained as yellow crystals having a melting point of 163 to 166° C.

Example 15

(Compound No.15)

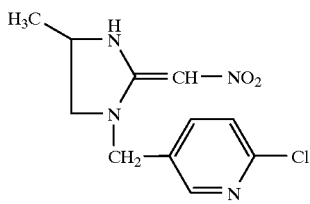

A mixture of 2 g of 2-amino-1-(2-chloro-5-pyridylmethylamino)propane, 1.6 g of 1-nitro-2,2-bis (methylthio)ethylene and 20 ml of methanol was refluxed for 5 hours with stirring. A crystaline product was precipitated after standing at room temperature. The product was filtered with suction, washed with methanol and then dried in vacuum. 1.9 g of 1-(2-chloro-5-pyridylmethyl)-4-methyl-2-(nitromethylene)imidazolidine was obtained in form of light yellow crystals.

mp. 170–174° C.

Example 16

(Compound No.16)

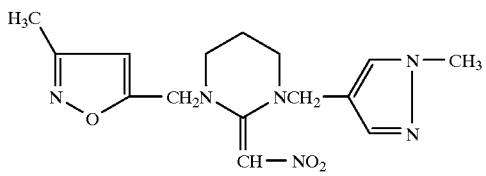

A mixture of 2.6 g of N-(3-methyl-5-isoxazolylmethyl)-N'-(1-methyl-4-pyrazolylmethyl)trimethylenediamine, 1.6 g of 1-nitro 2,2-bis(methylthio)ethylene and 10 ml of ethanol was refluxed for 15 hours with stirring. After the reaction, the ethanol was removed by vacuum distillation. The tarry residue was purified by chromatography on a silicagel column. The product, 0.7 g of 1-(3-methyl-5-isoxazolylmethyl-3-(1-methyl-4-pyrazolylmethyl)-2-(nitromethylene)tetrahydropyrimidine was obtained as a viscous oil.

$n_D^{20}$ 1.5670

Example 17

(Compound No.17)

6.6 g of finely powdered 1-nitro-2,2-bis(methylthio) ethylene was well mixed with 7.5 g of 2-(2-chloro-5-pyridylmethylamino)ethanol. The mixture was heated to 110–120° C. for 30 minutes or until the generation of methylmercaptan is ceased. The resulting oil was cooled to room temperature and purified by chromatography on a silicagel column. The product 3-(2-chloro-5-pyridylmethyl)-2-(nitromethylene) oxazolidine weighed 1.7 g.

mp. 123–124° C.

Example 18

(Compound No.18)

2.6 g of potassium hydroxide was dissolved in 20 ml of anhydrous ethanol. To the solution were added 3.7 g of 2-(2-methyl-5-pyrazinylmethylamino)ethanethiol under nitrogen atmosphere. The solution was then cooled to 0° C., and 3.0 g of 2,2-dichloro-1-nitroethylene was added dropwise at 0–10° C. After the addition, the mixture was stirred for 1 hour at 10° C. The ethanol was removed by vacuum distillation, chloroform was added to the residue and the chloroform layer was washed with 1% of sodium hydroxide solution and water. The chloroform layer was treated by usual manner, light yellow crystals of 3-(2-methyl-5-pyrazinylmethyl)-2-(nitromethylene)thiazolidine were obtained, and weighed 2.0 g.

mp. 147–150° C.

Example 19

(Compound No.19)

A mixture of 4.7 g of N-(1,2,5-thiadiazol-3-ylmethyl) ethylenediamine, 3.4 g of nitroguanidine and 20 ml of water was stirred at 50–60° C. for 1 hour then at 70° C. for 20 minutes. The resulting solution was then cooled slowly to 5° C., and the product was precipitated. The crystalline product was collected by filtration washed with water and methanol, and dried. The yield of 1-(1,2,5-thiadiazol-3-ylmethyl)-2-(nitroimino) imidazolidine was 2.9 g.

mp. 162–165° C.

Example 20

(Compound No.20)

A mixture of 2.9 g of 2-nitroiminothiazolidine, 2.9 g of anhydrous potassium carbonate, 3.2 g of 2-chloro-5-pyridylmethylchloride and 50 ml of acetonitrile was refluxed for 5 hours with vigorously stirring. After the reaction, most of the acetonitrile was removed by distillation and water was added to the residue. As the solid product was separated it was collected by filtration. The crude material was recrystallized from ethanol to give desired 3-(2-chloro-5-pyridylmethyl)-2-(nitroimino)thiazolidine.

yield 3.8 g mp. 137–138° C.

Example 21

(Compound No.21)

To a mixture of 1.3 g of finely powdered 2-nitroiminoimidazolidine and 30 ml of dry acetonitrile was added portionwise 0.4 g of sodium hydride (60% in oil) at room temperature and was stirred until the generation of hydrogen gas ceased. A solution of 1.7 g of 2-chloro-5-thiazolylmethylchloride in 10 ml of acetonitrile was then added dropwise at room temperature. After the addition, the mixture was stirred for 3 hours at room temperature and poured onto ice water. The organic layer was extracted with dichloromethane and the dichloromethane extract was washed with 1% sodium hydroxide solution and water. The product was solidified after evaporation of dichloromethane, washed with ether and dried. The desired 1-(2-chloro-5-thiazolylmethyl)-2-(nitroimino) imidazolidine weighed 1.4 g.

mp. 147–150° C.

Example 22

(Compound No.22)

By the procedure described in example 7 gummy substance was obtained from 2.3 g of ethyl nitro(tetrahydro- 2H-1,3-thiazin-2-ylidene)acetate and 1.6 g of 2-chloro-5-pyridylmethylchloride. This was triturated in ethanol and insoluble material was washed with hexane, then was purified by chromatography on a silicagel column. The desired ethyl [3-(2-chloro-5-pyridylmethyl)tetrahydro-2H-1,3-thiazin-2-ylidene]acetate weighed 0.2 g.

mp. 180–184° C.

Example 23

(Compound No.23)

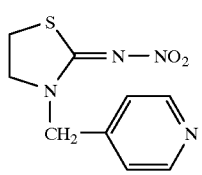

5.8 g of 2-imino-3-(4-pyridylmethyl)thiazolidine was added to 20 ml of conc. sulfuric acid at −5~0° C. 6 ml of fuming nitric acid was then added dropwise to the solution at the same temperature. After stirring for 30 minutes at 0~5° C., the reaction mixture was poured onto crushed ice. Twice extract with dichloromethan followed by treating in the usual way yielded 1.4 g of desired 2-nitroimino-3-(4-pyridylmethyl)thiazolidine.

mp. 151–152° C.

Example 24

(Compound No.24)

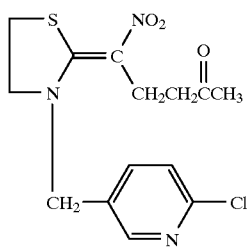

A mixture of 2.7 g of 3-(2-chloro-5-pyridylmethyl)-2-(nitromethylene) thiazolidine, 3.5 g of methyl vinylketone and 30 ml of chloroform was stirred for 2 days at 40° C. under nitrogen atmosphere. 3.5 g of methyl vinylketone was then added to the reaction mixture and stirred again for 2 days at the same temperature. After volatile material was removed in vacuum, the residue was purified by chromatography on silicagel column. The desired 3-(2-chloro-5-pyridylmethyl)-2-(1-nitro-4-oxopentylidene) thiazolidine weighed 0.1 g.

mp. 75–80° C.

Example 25

(Compound No.25)

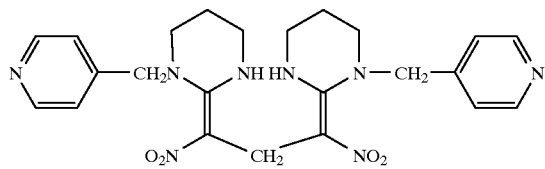

A mixture of 2.3 g of 1-(4-pyridylmethyl)-2-(nitromethylene)tetrahydropyrimidine, 0.5 g of paroforadehyde and 30 ml of dioxane was vigorously stirred for 2 hours at 70–80° C. After the reaction, the dioxane was evaporated to about one third of its volume under reduced pressure. The crystallized product was filtered and dried. The yield of desired bis-[δ-nitro-1-(4-pyridylmethyl)tetrahydropyrimidin-2-ylidenemethyl] methane was 1.8 g.

mp. 222–223° C.

Example 26

(compound No. 26)

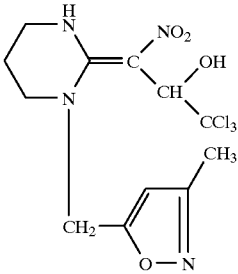

To a solution of 2.4 g of 1-(3-methyl-5-isoxazolylmethyl)-2-(nitromethylene)tetrahydropyrimidine and 30 ml of dry dichloromethane was added 1.6 g of trichloroacetaldehyde at room temperature. After stirring for 3 hours at 25–30° C., crystallized product was filtered, washed with ether and dried. The desired 1-(3-methyl-5-isoxazolylmethyl)-2-(1-nitro-2-hydroxy-3,3,3-trichloropropylidene)tetrahydropyrimidine weighed 3.1 g.

mp. 128–130° C. (decomp.)

Example 27

(Compound No. 27)

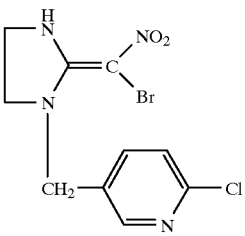

2.5 g of 1-(2-chloro-5-pyridylmethyl)-2-(nitromethylene) imidazolidine was dissolved in 40 ml of dry dichloromethane and 10 ml of water was added. A solution of 1.6 g of bromine in 10 ml of dichloromethane was added to the mixture within 10 minutes at 0–5° C. with stirring. After stirring for 10 minutes at 0–5° C., crystallized product was filtered, washed with cold water and a small quantity or dichloromethane and dried. The yield of 1-(2-chloro-5-pyridylmethyl)-2-(bromonitromethylene) imidazolidine was 2.5 g.

mp. 110–115° C. (decomp.)

Example 28

(Compound No. 28)

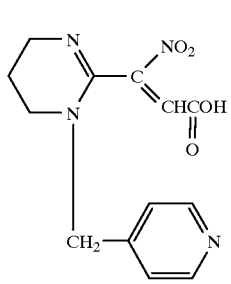

To a mixture of 1.2 g of finely powdered 1-(4-pyridylmethyl)-2-(nitromethylene)tetrahydropyrimidine in 20 ml of methanol was added 2 drops of conc. sulfuric acid and then 1.6 g of 25% aqueous glyoxylic acid. The mixture was stirred for 3 hours at room temperature. After adjusting to pH 7, the precipitated product was filtered, washed with water, methanol and ether respectively and dried. The desired 3-[1-(4-pyridylmethyl)-1H,4H,5H,6H-tetrahydropyrimidin-4-yl]3-nitro acrylic acid weighed 1.1 g.

mp. 150–155° C. (decomp.)

Example 29

(Compound No. 29)

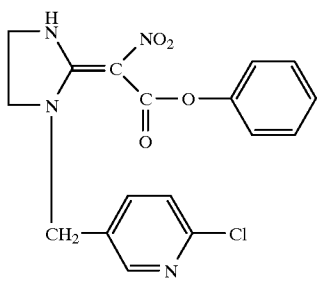

3.1 g of phenylchloroformate was added to a solution of 1.6 g of 1-methylimidazol in 50 ml of dichloromethane below 0° C. After stirring for 30 minutes at the same temperature, 2.5 g of 1-(2-chloro-5-pyridylmethyl)-(2-nitromethylene)imidazolidine was added to the mixture and the resulting mixture was stirred for 24 hours at room temperature. The mixture was then washed with water, 1% hydrochloric acid and 1% sodium hydroxide solution respectively. Removing the dichloromethane by distillation gives glassy phenyl nitro{1-(2-chloro-5-pyridylmethyl)-3-phenoxycarbonylimidazolidin-2-ylidene} acetate (3.2 g). This was then dissolved in 20 ml of dimethylformamide, 1.7 g of sodium carbonate was added to the solution, and the mixture was stirred for 3 days at room temperature. Water was then added and the organic layer was extracted with dichloromethane. The extract was washed with 1% sodium hydroxide solution and water. After evaporation of dichloromethane, the residue was purified by chromatography on a silicagel column. The desired product, phenyl nitro{1-(2-chloro-5-pyridylmethyl)imidazolidin-2-ylidene}acetate weighed 0.2 g. mp. 224–228° C. (decomp.)

Example 30

(Compound No. 30)

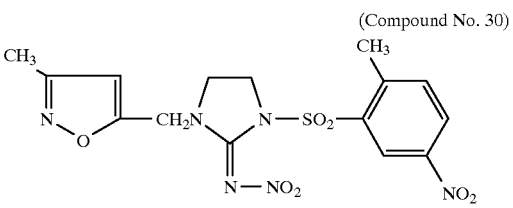

0.2 g of sodium hydride 60% in oil was added to a solution of 1.1 g of 1-(3-methylisoxazol-5-ylmethyl)-2-nitroiminoimidazolidine in 15 ml of dry dimethylformamide and the mixture was stirred until the generation of hydrogen gas ceased. 1.2 g of 2-methyl-5-nitrobenzenesulfonylchloride was then added to the mixture. After stirring for 1 day at room temperature, the reaction mixture was poured into ice water, and the organic layer was extracted with dichloromethane. The dichloromethane was removed by distillation to give crystalline product, and this was washed with ether. The desired 1-(2-methyl-5-nitrobenzenesulfonyl)-3-(3-methylisoxazol-5-ylmethyl)-2-nitroiminoimidazolidine weighed 1.1 g.

mp. 154–156° C.

Example 31

(Compound No. 31)

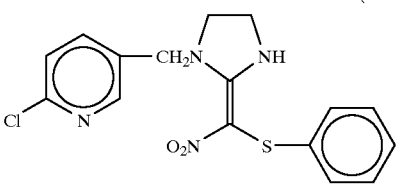

0.2 g of sodium hydride 60% in oil was added to a solution of 1.3 g of 1-(2-chloro-5-pyridylmethyl)-2-nitromethyleneimidazolidine in 15 ml of dry dimethylformamide, and the mixture was stirred at room temperature until the generation of hydrogen gas ceased. 0.9 g of 4-chlorobenzenesulfenylchloride was then drop into the solution at 0° C. with stirring. After stirring for 1 hour at room temperature, the reaction mixture was poured into ice water. The precipitated crystal was filtered and recrystalized from ethyl acetate to give 1-(2-chloro-5-pyridylmethyl)-2-{(4-chlorophenylthio)nitromethylene}imidazolidine. The yield was 1.3 g.

mp. 159–161° C.

Example 32

(Compound No. 32)

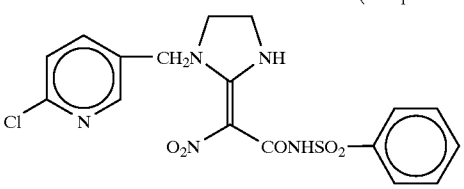

A solution of 0.9 g of benzenesulfonylisocyanate in 10 ml of dry dichloromethane was added dropwise to a solution of 1.3 g of 1-(2-chloro-5-pyridylmethyl)-2-nitromethyleneimidazolidine in 25 ml of dry dichloromethane at room temperature. The solution was stirred for 2 hours at the same temperature and then about a half volume of dichloromethane was evaporated under reduced pressure. The product which crystallized was filtered and washed with ether. The desired N-benzenesulfonyl-2-{1-(2-chloro-5-pyridylmethyl)imidazolidin-2-ylidene}-2-nitroacetamide weighed 1 g.

mp. 95–100°C.

Example 33

(Compound No. 33)

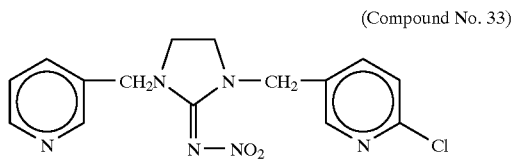

A mixture of 2.2 g of 2-nitroimino-1-(3-pyridylmethyl)imidazolidine, 1.6 g of 2-chloro-5-chloromethylpyridine, 1.4 g of anhydrous potassium carbonate in 30 ml of acetonitrile was refluxed for 16 hours with stirring. The acetonitrile was then removed under reduced pressure, dichloromethane was added to the residue and was washed with water and 1% sodium hydroxide solution. The residue after removing dichloromethane under reduced pressure was purified by chromatography on a silicagel column to give 1-(2-chloro-5-pyridylmethyl-2-nitroimino-3-(3-pyridylmethyl)imidazolidine. The yield was 2.1 g.

mp. 143–144° C.

Example 34

(Compound No. 34)

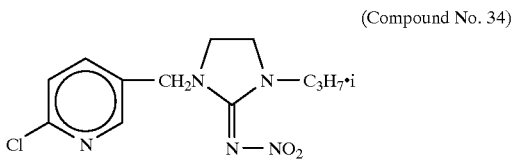

0.4 g of sodium hydride 60% in oil was added portionwise to a solution of 2.6 g of 1-(2-chloro-5-pyridylmethyl)-2-nitroiminoimidazolidine in 20 ml of dry dimethylformamide. The mixture was stirred at room temperature until the evolution of hydrogen ceased. A solution of 1.5 g of isopropyl bromide in 5 ml of dry dimethylformamide was added dropwise to the mixture at room temperature and stirred for 3 hours at room temperature after the addition. The reaction mixture was then poured into ice water, and the precipitated crystals filtered. This was recrystallized from ethanol to give 1-(2-chloro-5-pyridylmethyl)-3-isopropyl-2-nitroiminoimidazolidine. The yield was 1.5 g.

mp. 138–142° C.

Example 35

(Compound No. 35)

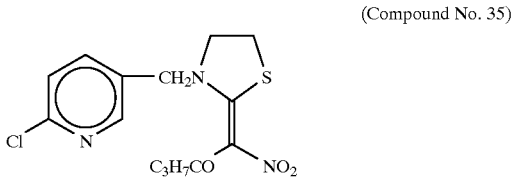

A mixture of 2.7 g of 3-(2-chloro-5-pyridylmethyl)-2-nitromethylenethiazolidine and 8 ml of butyric anhydride stirred for 8 hours at 60° C. under nitrogen atmosphere. The volatile material was then removed by distillation at 1 mmHg, keeping the bath temperature below 60° C. The residue was dissolved in dichloromethane and washed with 1% sodium hydroxide solution. The dichloromethane layer was then purified by chromatography on a silicagel column to give viscous oily 1-{3-(2-chloro-5-pyridylmethyl)thiazolidine-2-ylidene}-1-nitro-2-pentanone. The yield was 0.15 g.

$n_D^{20}$ 1.6342

In accordance with the same method as in the above examples, the compounds of the formula (I) are shown in the following tables.

In the tables, "—" for $R^3$ and $R^4$ means n is 0 and in such case, the corresponding ring-structure is 5-membered heterocyclic ring.

The case where X is a sulfur atom and the formula (I) represents the following formula: —(table 1)

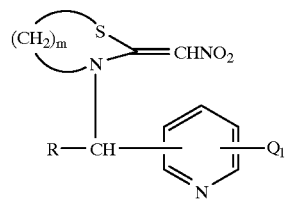

TABLE 1

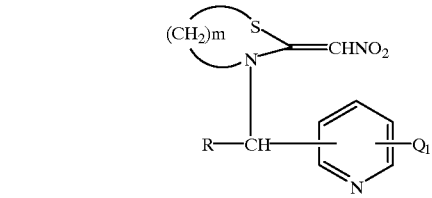

| Compound No. | m | R | Bonding positions of the pyridine ring | $Q_1$ |
|---|---|---|---|---|
| 36 | 2 | H | 5- | 2-F |
| 37 | 3 | H | 5- | 2-F |
| 38 | 2 | —CH₃ | 5- | 2-Cl |
| 39 | 2 | H | 5- | 2-Br |
| 40 | 2 | R | 5- | 2,3-Cl₂ |
| 41 | 2 | H | 5- | 2,3,4,6-F₄ |
| 42 | 2 | H | 4- | 2-Cl |
| 43 | 3 | R | 5- | 2-Br |
| 44 | 2 | R | 5- | 2-F, 3-Cl |
| 45 | 2 | H | 2- | 3-Cl |
| 46 | 3 | H | 2- | 5-Cl |
| 47 | 2 | H | 2- | 3,5-Cl₂ |
| 48 | 3 | H | 2- | 5-F |
| 49 | 2 | R | 2- | 6-Br |
| 50 | 3 | H | 3- | 2-Cl |
| 51 | 3 | H | 3- | 5-Cl |
| 52 | 2 | H | 3- | 5-Br |
| 53 | 2 | H | 3- | 5-F |
| 54 | 2 | —CH₃ | 5- | 2-F |
| 55 | 3 | H | 5- | 2,4-Cl₂ |
| 56 | 2 | H | 5- | 2,4-Br₂ |
| 57 | 2 | H | 4- | 2,6-F₂ |
| 58 | 3 | H | 4- | 2-F |
| 59 | 2 | H | 4- | 2,6-Br₂ |
| 60 | 2 | H | 5- | 2-F, 3-Br |
| 61 | 2 | H | 5- | 2-Cl, 3-F |
| 62 | 2 | —C₂H₅ | 5- | 2-Cl₃ |
| 63 | 2 | H | 4- | — |
| 64 | 3 | H | 4- | — |
| 65 | 2 | H | 5- | 2-CH₃ |
| 66 | 3 | H | 5- | 2-CH₃ |

TABLE 1-continued

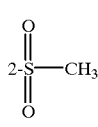

| Compound No. | m | R | Bonding positions of the pyridine ring | Q₁ |
|---|---|---|---|---|
| 67 | 2 | H | 5- | 2-$C_2H_5$ |
| 68 | 2 | H | 5- | 2-$CH_2CH=CH_2$ |
| 69 | 2 | H | 5- | 2-$CH_2C\equiv CH$ |
| 70 | 3 | H | 5- | 2-$OCH_3$ |
| 71 | 2 | H | 5- | 2-$SCH_3$ |
| 72 | 2 | H | 5- | 2-$S(O)_2CH_3$ |
| 73 | 2 | H | 5- | 2-Cl, 3-$CH_3$ |
| 74 | 2 | —$CH_3$ | 3- | — |
| 75 | 2 | H | 5- | 2-$CF_3$ |
| 76 | 3 | H | 5- | 2-$CF_3$ |
| 77 | 2 | H | 5- | 2-$NO_2$ |
| 78 | 3 | H | 5- | 2-$NO_2$ |
| 79 | 2 | H | 5- | 2-CN |
| 80 | 3 | H | 5- | 2-CN |
| 81 | 2 | H | 5- | 2-$S(O)CH_3$ |
| 82 | 2 | H | 5- | 2-$C_6H_5$ |
| 83 | 2 | H | 5- | 2-$CH_2C_6H_5$ |

TABLE 1-continued

| Compound No. | m | R | Bonding positions of the pyridine ring | Q₁ |
|---|---|---|---|---|
| 84 | 3 | H | 5- | 2-$OC_6H_5$ |
| 85 | 2 | H | 5- | 2-$CCl_3$ |
| 86 | 3 | H | 5- | 2-$C_2H_4OC_2H_5$ |
| 87 | 2 | H | 5- | 2-$CH_2OCH_3$ |
| 88 | 2 | H | 5- | 2-$OCHF_2$ |
| 89 | 2 | H | 5- | 2-$OCF_3$ |
| 90 | 2 | B | 5- | 2-$OCH_2CF_3$ |
| 91 | 3 | H | 5- | 2-$SCClF_2$ |
| 92 | 2 | H | 5- | 2-$SCF_3$ |
| 93 | 2 | H | 5- | 2-$CHF_2$ |
| 94 | 2 | H | 5- | 2-$S(O)_2CF_3$ |
| 95 | 2 | H | 5- | 2-$S(O)CF_3$ |
| 96 | 2 | H | 5- | 2-$CH=CCl_2$ |

Besides table 1, the case where X is a sulfur atom: —(table 2)

TABLE 2

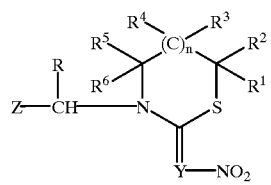

| Comp. No. | Z | R | R¹ | R² | R³ | R⁴ | R⁵ | R⁶ | n | Y |
|---|---|---|---|---|---|---|---|---|---|---|
| 97 | 3-pyridyl | H | H | H | — | — | H | H | 0 | N |

TABLE 2-continued
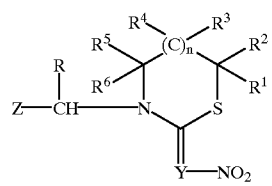
| Comp. No. | Z | R | R¹ | R² | R³ | R⁴ | R⁵ | R⁶ | n | Y | |
|---|---|---|---|---|---|---|---|---|---|---|---|
| 98 | 2-F-5-pyridyl | H | H | H | — | — | H | H | 0 | N | |
| 99 | 2-CF₃-5-pyridyl | H | H | H | — | — | H | H | 0 | N | |
| 100 | 2-FCl₂C-5-pyridyl | H | H | H | H | H | H | H | 1 | N | |
| 101 | 4,5-diCl-2-thienyl | H | H | H | — | — | H | H | 0 | N | |
| 102 | 1-methyl-pyrazol-4-yl | H | H | H | — | — | H | H | 0 | N | |
| 103 | 1-methyl-pyrazol-4-yl | H | H | H | H | H | H | H | 1 | N | |
| 104 | 1-propargyl-pyrazol-4-yl | H | H | H | — | — | H | H | 0 | N | |
| 105 | 3-methyl-isoxazol-5-yl | H | H | H | — | — | H | H | 0 | N | mp. 143–145° C. |
| 106 | 2-Cl-thiazol-5-yl | H | H | H | — | — | H | H | 0 | N | |
| 107 | 2-Cl-thiazol-5-yl | H | H | H | H | H | H | H | 1 | N | |

TABLE 2-continued

| Comp. No. | Z | R | R¹ | R² | R³ | R⁴ | R⁵ | R⁶ | n | Y |
|---|---|---|---|---|---|---|---|---|---|---|
| 108 | 2-CF₃-5-thiazolyl | H | H | H | — | — | H | H | 0 | N |
| 109 | 4-methyl-1,2,3-thiadiazol-5-yl | H | H | H | — | — | H | H | 0 | N |
| 110 | 5-methyl-1,3,4-thiadiazol-2-yl | H | H | H | H | H | H | H | 1 | N |
| 111 | 5-methyl-1,2,3-thiadiazol-4-yl | H | H | H | — | — | H | H | 0 | N |
| 112 | 5-pyrimidinyl | H | H | H | — | — | H | H | 0 | CH |
| 113 | 2-chloro-5-pyrimidinyl | H | H | H | — | — | H | H | 0 | CH |
| 114 | 2-methyl-5-pyrimidinyl | H | H | H | H | H | H | H | 1 | CH |
| 115 | 6-chloro-3-pyridazinyl | H | H | H | — | — | H | H | 0 | CH |
| 116 | 5-pyrimidinyl | H | H | H | — | — | H | H | 0 | N |
| 117 | 2-chloro-5-pyrimidinyl | H | H | H | — | — | H | H | 0 | N |
| 118 | 5-methyl-2-pyrazinyl | H | H | H | — | — | H | H | 0 | N |

TABLE 2-continued
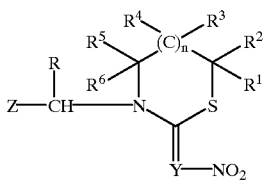
| Comp. No. | Z | R | R¹ | R² | R³ | R⁴ | R⁵ | R⁶ | n | Y |
|---|---|---|---|---|---|---|---|---|---|---|
| 119 | 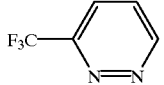 | H | H | H | — | — | H | H | 0 | N |
| 120 | 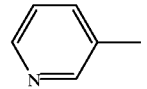 | H | H | H | H | H | H | H | 1 | C—CH₃ |
| 121 | 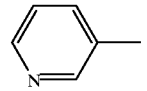 | H | H | H | — | — | H | H | 0 | C—CH₂F |
| 122 | 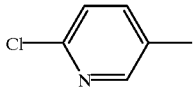 | H | H | H | — | — | H | H | 0 | C—CF₃ |
| 123 | 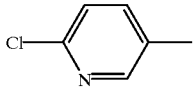 | H | H | H | — | — | H | H | 0 | C—CH₂OCH₃ |
| 124 | 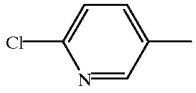 | H | H | H | — | — | H | H | 0 | C—CH₂SC₂H₅ |
| 125 | 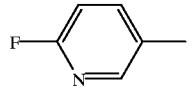 | H | H | H | H | H | H | H | 1 | C—CH₂N(CH₃)₂ |
| 126 | 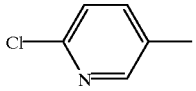 | H | H | H | H | H | H | H | 1 | C—CH₂CH=CH₂ |
| 127 | 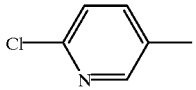 | H | H | H | — | — | H | H | 0 | C—(CH₂)₂CN |
| 128 | 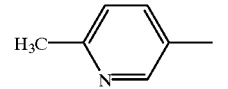 | H | H | H | — | — | H | H | 0 | C—(CH₂)₂COOCH₃ |
| 129 | 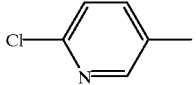 | H | H | H | — | — | H | H | 0 | C—CHCCl₃ with OH |

TABLE 2-continued

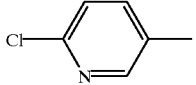

| Comp. No. | Z | R | R¹ | R² | R³ | R⁴ | R⁵ | R⁶ | n | Y | |
|---|---|---|---|---|---|---|---|---|---|---|---|
| 130 | 2-Cl-pyridin-5-yl | H | H | H | H | H | H | H | 1 | C—C₆H₅ | |
| 131 | 2-Cl-pyridin-5-yl | H | H | H | — | — | H | H | 0 | C—COCH₃ | $n_D^{25}$ 1.6358 |
| 132 | pyridin-3-yl | H | H | H | H | H | H | H | 1 | C—COCH₂OCH₃ | |
| 133 | 2-F-pyridin-5-yl | H | H | H | — | — | H | H | 0 | C—COCCl₃ | |
| 134 | 2-Cl-pyridin-5-yl | H | H | H | — | — | H | H | 0 | C—CO—C₆H₅ | |
| 135 | 2-CH₃-pyridin-5-yl | H | H | H | H | H | H | H | 1 | C—CO—C₆H₄—Br (4-) | |
| 136 | pyridin-4-yl | H | H | H | H | H | H | H | 1 | C—COOCH₃ | |
| 137 | 2-F-pyridin-5-yl | H | H | H | H | H | H | H | 1 | C—COOC₂H₅ | |
| 138 | 2-Cl-pyridin-5-yl | H | H | H | — | — | H | H | 0 | C—COOC₂H₅ | |
| 139 | 2-CF₃-pyridin-5-yl | H | H | H | — | — | H | H | 0 | C—COO—C₆H₄—Cl (4-) | |
| 140 | 2-Cl-pyridin-5-yl | H | H | H | — | — | H | H | 0 | C—S—(CH₂)₃CH₃ | |

TABLE 2-continued

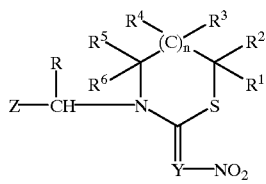

| Comp. No. | Z | R | R¹ | R² | R³ | R⁴ | R⁵ | R⁶ | n | Y | |
|---|---|---|---|---|---|---|---|---|---|---|---|
| 141 | 6-chloropyridin-3-yl | H | H | H | — | — | H | H | 0 | C—S—phenyl | |
| 142 | 6-chloropyridin-3-yl | H | H | H | — | — | H | H | 0 | C—CONHCO-(2-methylphenyl) | |
| 143 | 6-chloropyridin-3-yl | H | H | H | — | — | H | H | 0 | C—CONHSO₂-(2-chlorophenyl) | |
| 144 | 6-chloropyridin-3-yl | H | H | CH₃ | — | — | H | H | 0 | N | |
| 145 | 1-methylpyrazol-4-yl | H | H | H | — | — | H | H | 0 | C—COO-phenyl | |
| 146 | 3,5-dimethylisoxazol-4-yl | H | H | H | H | H | H | H | 1 | C—COOC₂H₅ | $n_D^{24}$ 1.5978 |
| 147 | 2-methylpyrimidin-5-yl | H | H | H | — | — | H | H | 0 | C—COCH₃ | |
| 148 | 2-chloropyrimidin-5-yl | H | H | H | — | — | H | H | 0 | C—COOCH₃ | |
| 149 | 6-methylpyrazin-3-yl | H | H | H | — | — | H | H | 0 | C—COOCH₂CF₃ | |
| 150 | 1-methylpyrrol-3-yl | H | H | H | — | — | H | H | 0 | CH | |

TABLE 2-continued $$Z-CH(R)-N(R^6)-C(=Y-NO_2)-S-C(R^1)(R^2)-(C(R^3)(R^4))_n-C(R^5)(R^6)?$$

Structure:
$$\begin{array}{c} R^4\ R^3 \\ R^5\text{--}(C)_n\text{--}R^2 \\ Z\text{--}CH(R)\text{--}N(R^6)\text{--}C(=Y\text{--}NO_2)\text{--}S\text{--}C(R^1) \end{array}$$

| Comp. No. | Z | R | R¹ | R² | R³ | R⁴ | R⁵ | R⁶ | n | Y |
|---|---|---|---|---|---|---|---|---|---|---|
| 151 | 3-CF₃-4-methylisoxazol-5-yl | H | H | H | H | H | H | H | 1 | CH |
| 152 | 1-methyl-4-methylpyrazol-3-yl | H | H | H | H | H | H | H | 1 | CH |
| 153 | 1-allyl-4-methylpyrazol-3-yl | H | H | H | — | — | H | H | 0 | CH |
| 154 | 3-methyl-5-methylisoxazol-4-yl | H | H | H | H | H | H | H | 1 | CH |
| 155 | 2-fluoro-5-methylthiazol-4-yl | H | H | H | H | H | H | H | 1 | CH |
| 156 | 2-chloro-5-methylthiazol-4-yl | H | H | H | H | H | H | H | 1 | CH |
| 157 | 2-(Cl₃CCONH)-5-methylthiazol-4-yl | H | H | H | — | — | H | H | 0 | CH |
| 158 | 2-chloro-5-methyloxazol-4-yl | H | H | H | — | — | H | H | 0 | CH |
| 159 | 4-methyl-1,2,3-thiadiazol-5-yl | H | H | H | — | — | H | H | 0 | CH |
| 160 | 5-methyl-1,2,3-thiadiazol-4-yl | H | H | H | H | H | H | H | 1 | CH | the case where X is CH—R⁸: —(table 3)

TABLE 3
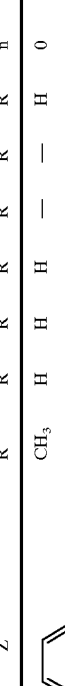
| Comp. No. | Z | R | R¹ | R² | R³ | R⁴ | R⁵ | R⁶ | n | R⁸ | Y |
|---|---|---|---|---|---|---|---|---|---|---|---|
| 161 | 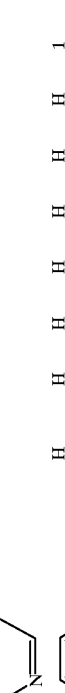 | CH₃ | H | H | H | — | — | H | 0 | H | CH |
| 162 |  | H | H | H | H | — | H | H | 1 | H | CH |
| 163 |  | H | H | H | — | — | H | H | 0 | H | CH |
| 164 |  | H | H | H | — | — | H | H | 0 | H | CH |
| 165 |  | H | H | H | — | — | H | H | 0 | H | CH |
| 166 |  | H | H | H | — | — | H | H | 0 | H | CH |
| 167 | 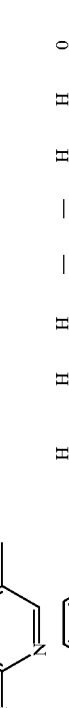 | H | H | H | — | — | H | H | 0 | H | CH |
| 168 | | H | H | H | — | — | H | H | 0 | H | CH |

TABLE 3-continued

| Comp. No. | Z | R | $R^1$ | $R^2$ | $R^3$ | $R^4$ | $R^5$ | $R^6$ | n | $R^8$ | Y | |
|---|---|---|---|---|---|---|---|---|---|---|---|---|
| 169 | 2-Cl-5-pyridyl | H | H | H | H | H | H | H | 1 | H | N | |
| 170 | 2-Cl-5-pyridyl | H | H | H | H | H | H | H | 1 | H | N | |
| 171 | 2-Br-5-pyridyl | H | H | H | — | — | H | H | 0 | H | N | |
| 172 | 2-CF₃-5-pyridyl | H | H | H | — | — | H | H | 0 | H | N | |
| 173 | 4-CH₃-pyrazolyl | CH₃ | H | H | — | — | H | H | 0 | H | CH | |
| 174 | 5-CH₃-isoxazolyl | H | H | H | — | — | H | H | 0 | H | CH | |
| 175 | 5-CHF₂-isoxazolyl | H | H | H | H | H | H | H | 1 | H | CH | $n_D^{20}$ 1.5995 |

TABLE 3-continued $$\underset{R}{Z-CH} \overset{R^5}{\underset{R^6}{\bigg\langle}} \overset{R^4}{\underset{(C_n)}{\bigg\rangle}} \overset{R^3}{\underset{N}{\bigg\langle}} \overset{R^2}{\underset{CH-R^8}{\bigg\rangle}} Y-NO_2$$

| Comp. No. | Z | R | $R^1$ | $R^2$ | $R^3$ | $R^4$ | $R^5$ | $R^6$ | n | $R^8$ | Y |
|---|---|---|---|---|---|---|---|---|---|---|---|
| 176 | 5-methyl-2-chlorothiazole | H | H | H | — | — | H | H | 0 | H | CH |
| 177 | 5-methyl-2-methoxythiophene | H | H | H | — | — | H | H | 0 | H | CH |
| 178 | 5-methyl-oxazole | H | H | H | H | H | H | H | 1 | H | CH |
| 179 | 4-methyl-isothiazole | H | H | H | — | — | H | H | 0 | H | CH |
| 180 | 3-methyl-pyrazole | H | H | H | — | — | H | H | 0 | H | N |
| 181 | methyl-pyrazole-CH₂-CCl₂ | H | H | H | H | H | H | H | 1 | H | N |
| 182 | 5-methyl-isoxazole | H | H | H | — | — | H | H | 0 | H | N |

TABLE 3-continued

| Comp. No. | Z | R | R¹ | R² | R³ | R⁴ | R⁵ | R⁶ | n | R⁸ | Y |
|---|---|---|---|---|---|---|---|---|---|---|---|
| 183 | 2-chloro-5-thiazolyl | H | H | H | — | — | H | H | 0 | tolyl | N |
| 184 | 3-methyl-1,2,5-thiadiazolyl | H | H | H | — | — | H | H | 0 | H | N |
| 185 | 6-methyl-3-pyridyl | H | H | H | — | — | H | H | 0 | H | CH |
| 186 | 6-methyl-3-pyridyl | H | H | H | — | — | H | H | 0 | H | CH |
| 187 | 6-methyl-3-pyridyl | $CH_3$ | H | H | — | — | H | H | 0 | H | CH |
| 188 | 2,5-dimethylpyrazinyl | H | H | H | — | — | H | H | 0 | benzyl | CH |
| 189 | 6-methyl-3-pyridazinyl | H | H | H | — | — | H | H | 0 | H | N |
| 190 | 6-methyl-3-pyridazinyl | H | H | H | — | — | H | H | 0 | H | N |

TABLE 3-continued
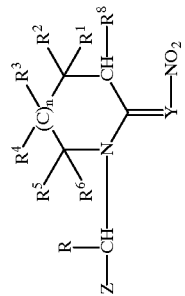
| Comp. No. | Z | R | R¹ | R² | R³ | R⁴ | R⁵ | R⁶ | n | R⁸ | Y |
|---|---|---|---|---|---|---|---|---|---|---|---|
| 191 | 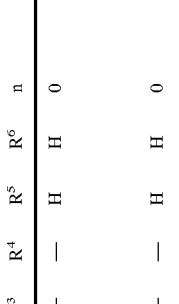 | H | H | H | — | — | H | H | 0 | H | N |
| 192 | 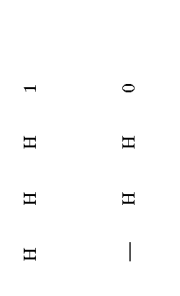 | H | H | H | — | — | H | H | 0 | H | N |
| 193 | 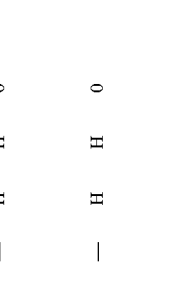 | H | H | H | H | H | H | H | 1 | CH₃ | CH |
| 194 | 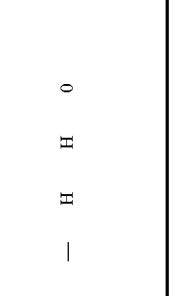 | H | H | H | — | — | H | H | 0 | H | C—COOC₂H₅ |
| 195 | 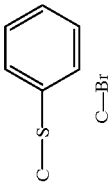 | H | H | H | — | — | H | H | 0 | H | C—S—C₆H₅ |
| 196 | 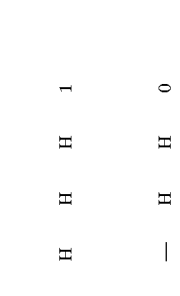 | H | H | H | — | — | H | H | 0 | H | C—Br |
| 197 |  | H | H | H | — | — | H | H | 1 | H | C—S—C₆H₄Cl |
| 198 | 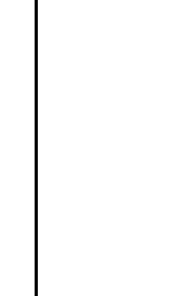 | H | H | H | — | — | H | H | 0 | CH₃ | H |

The case where X is an oxygen atom: —(table 4)
TABLE 4
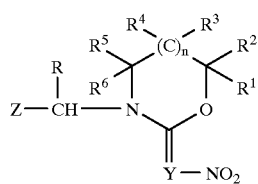
| Comp. No. | Z | R | R¹ | R² | R³ | R⁴ | R⁵ | R⁶ | n | Y | |
|---|---|---|---|---|---|---|---|---|---|---|---|
| 199 | 3-pyridyl | H | H | H | — | — | H | H | 0 | CH | mp. 137–140° C. |
| 200 | 4-pyridyl | H | H | H | H | H | H | H | 1 | CH | |
| 201 | 2-NC-5-pyridyl | H | H | H | — | — | H | H | 0 | CH | |
| 202 | 2-H₃C-5-pyridyl | H | H | H | — | — | H | H | 0 | CH | |
| 203 | 2-F₃C-5-pyridyl | H | H | H | — | — | H | H | 0 | CH | |
| 204 | 2-F-5-pyridyl | H | H | H | — | — | H | H | 0 | N | |
| 205 | 2-Cl-5-pyridyl | H | H | H | — | — | H | H | 0 | N | |
| 206 | 2-F₃CS-5-pyridyl | H | H | H | — | — | H | H | 0 | N | |
| 207 | 2-H₃C-5-pyridyl | H | H | H | — | — | H | H | 0 | N | |
| 208 | 2-Cl-4-methyl-furyl | H | H | H | — | — | H | H | 0 | CH | |
| 209 | 1-methyl-pyrazolyl | H | H | H | — | — | H | H | 0 | CH | |

TABLE 4-continued
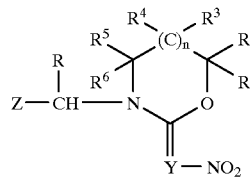
| Comp. No. | Z | R | R¹ | R² | R³ | R⁴ | R⁵ | R⁶ | n | Y |
|---|---|---|---|---|---|---|---|---|---|---|
| 210 | 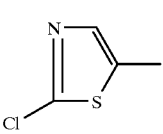 | H | H | H | — | — | H | H | 0 | CH |
| 211 | 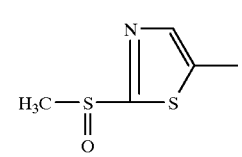 | H | H | H | — | — | H | H | 0 | CH |
| 212 | 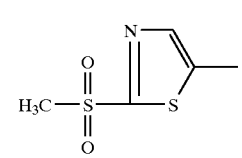 | H | H | H | H | H | H | H | 1 | CH |
| 213 | 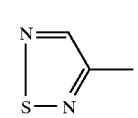 | H | H | H | H | H | H | H | 1 | CH |
| 214 | 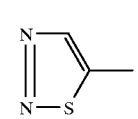 | H | H | H | — | — | H | H | 0 | CH |
| 215 | 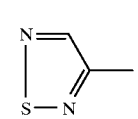 | H | H | H | H | H | H | H | 1 | CH |
| 216 | 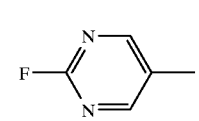 | H | H | H | — | — | H | H | 0 | N |
| 217 | 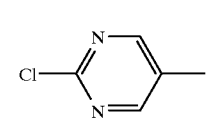 | H | H | H | — | — | H | H | 0 | CH |
| 218 | 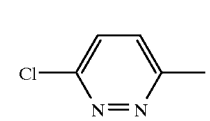 | H | H | H | — | — | H | H | 0 | CH |
| 219 |  | H | H | H | — | — | H | H | 0 | CH |

TABLE 4-continued
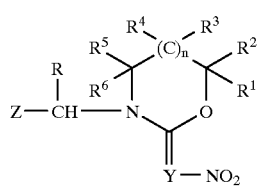
| Comp. No. | Z | R | R¹ | R² | R³ | R⁴ | R⁵ | R⁶ | n | Y |
|---|---|---|---|---|---|---|---|---|---|---|
| 220 | 6-Cl-pyridin-3-yl | H | H | H | — | — | H | H | 0 | C—CH₃ |
| 221 | 6-CH₃-pyridin-3-yl | H | H | H | — | — | CH₃ | H | 0 | CH |
| 222 | 6-Cl-pyridin-3-yl | H | H | H | — | — | H | H | 0 | C—COO—Ph |
| 223 | furan-2-yl | H | H | H | — | — | H | H | 0 | C—CO—Ph |
| 224 | 3-CH₃-isoxazol-5-yl | H | H | H | — | — | H | H | 0 | C—CO—(CH₂)₂CH₃ |
The case where the formula (I) represents the following formula: —(table 5)
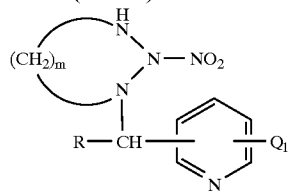
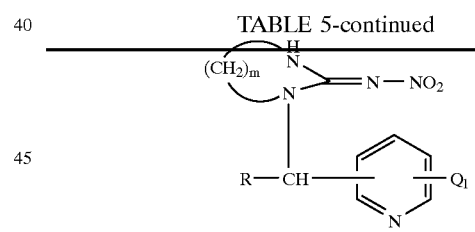
TABLE 5
| Compound No. | m | R | Bonding position on the pyridine ring | Q₁ | |
|---|---|---|---|---|---|
| 225 | 2 | H | 3- | — | m.p. 90–94° C. (dec.) |
| 226 | 3 | H | 3- | — | |
| 227 | 2 | —CH₃ | 3- | — | |
| 228 | 2 | —C₂H₅ | 3- | — | |
| 229 | 2 | —CH(CH₃)₂ | 3- | — | |
| 230 | 2 | H | 4- | — | m.p. 154–157° C. |
| 231 | 3 | H | 4- | — | m.p. 163–165° C. |
| 232 | 2 | H | 2- | 5-Cl | |
| 233 | 3 | H | 5- | 2-F | |
| 234 | 2 | —CH₃ | 5- | 2-Cl | |
| 235 | 2 | H | 5- | 2-Br | |

TABLE 5-continued

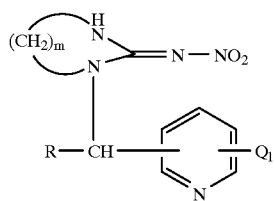

| Compound No. | m | R | Bonding position on the pyridine ring | Q₁ | |
|---|---|---|---|---|---|
| 236 | 2 | H | 5- | 2-CH₃ | m.p. 157–160° C. |
| 237 | 3 | H | 5- | 2-CH₃ | m.p. 155.5–158.5° C. |
| 238 | 2 | H | 5- | 2-C₂H₅ | |
| 239 | 2 | H | 5- | 2-OCH₃ | |
| 240 | 2 | H | 5- | 2-OC₂H₅ | |
| 241 | 2 | H | 5- | 2-SCH₃ | |
| 242 | 2 | H | 5- | 2-NO₂ | |
| 243 | 2 | H | 5- | 2-CN | |
| 244 | 2 | H | 5- | 2-NH₂ | |
| 245 | 3 | H | 5- | 2-NHC(O)CH₃ | |
| 246 | 2 | H | 5- | 2-N(CH₃)₂ | |
| 247 | 2 | H | 5- | 2-C(O)—OC₂H₅ | |
| 248 | 2 | H | 5- | 2-C(O)—CH₃ | |
| 249 | 2 | H | 5- | 2-S(O)—CH₃ | |
| 250 | 2 | H | 5- | 2-S(O)₂—CH₃ | |
| 251 | 2 | H | 5- | 2-CHF₂ | |
| 252 | 2 | H | 5- | 2-CF₃ | mp. 134–146° C. |
| 253 | 3 | H | 5- | 2-CF₃ | |
| 254 | 2 | H | 5- | 2-CCl₃ | |
| 255 | 2 | H | 5- | 2-CF₂Cl | |

TABLE 5-continued

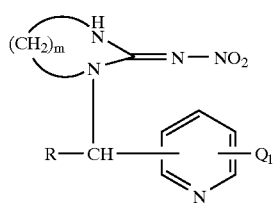

| Compound No. | m | R | Bonding position on the pyridine ring | Q₁ | |
|---|---|---|---|---|---|
| 256 | 2 | H | 5- | 2-CH₂CH₂F | |
| 257 | 2 | H | 5- | 2-CH₂CH₂Cl | |
| 258 | 2 | H | 5- | 2-CH₂CF₃ | |
| 259 | 3 | H | 5- | 2-OCHF₂ | |
| 260 | 2 | H | 5- | 2-OCF₃ | |
| 261 | 3 | H | 5- | 2-OCH₂CF₃ | |
| 262 | 2 | H | 5- | 2-SCF₃ | |
| 263 | 2 | H | 5- | 2-SCF₂Cl | |
| 264 | 2 | H | 5- | 3-Br | m.p. 198–201° C. |
| 265 | 2 | H | 2- | 5-CF₃ | |
| 266 | 2 | H | 5- | 2-CH₂C≡CH | |
| 267 | 2 | H | 5- | 2-CH₂CH=CH₂ | |
| 268 | 2 | H | 5- | 2-CH=C(Cl)₂ | |
| 269 | 2 | H | 5- | 2,3-Cl₂ | |
| 270 | 2 | H | 5- | 2-Cl, 3-CH₃ | |
| 271 | 2 | H | 4- | 2,3,5,6-F₄ | |
| 272 | 2 | H | 5- | 2-CHO | |
| 273 | 2 | H | 5- | 2-CF₂Br | |

The case where Z is optionally substituted-pyridyl and X is N—R⁷: —(table 6)

The formula (I) has the following formula;

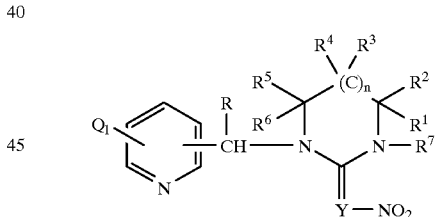

In the table 5, "—" for $Q_l$ means no substituent and "—" for both $R^2$ and $R^5$ mean that $R^2$ forms a single bond, together with $R^5$.

TABLE 6

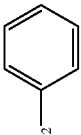

| Comp. No. | positions $Q_1$ | Bonding of the pyridine ring | R | $R^1$ | $R^2$ | $R^3$ | $R^4$ | $R^5$ | $R^6$ | n | $R^7$ | Y | |
|---|---|---|---|---|---|---|---|---|---|---|---|---|---|
| 274 | — | 4-position | H | H | $CH_3$ | — | — | H | H | 0 | H | CH | mp. 184–187° C. |
| 275 | — | 3-position | $CH_3$ | $CH_3$ | H | — | — | H | H | 0 | H | CH | |
| 276 | — | 3-position | H | H | $CH_3$ | $CH_3$ | — | H | H | 0 | H | CH | mp. 177–180° C. |
| 277 | — | 4-position | H | H | H | OH | $CH_3$ | H | H | 1 | H | CH | mp. 190–191° C. |
| 278 | — | 4-position | H | H | $CH_3$ | — | $CH_3$ | H | H | 1 | H | CH | mp. 209–212° C. |
| 279 | 2-F | 5-position | H | H | H | H | — | H | H | 0 | H | CH | |
| 280 | 2-Cl | 5-position | H | H | $C_2H_5$ | — | — | $CH_3$ | H | 1 | H | CH | |
| 281 | 2-Cl | 5-position | H | H | $CH_3$ | — | — | H | H | 0 | H | CH | |
| 282 | 2-Br | 5-position | H | H | $CH_3$ | — | — | H | H | 0 | H | CH | |
| 283 | 2-CF$_3$ | 5-position | H | H | $CH_3$ | — | — | H | H | 0 | H | CH | |
| 284 | 2-CH$_3$ | 5-position | H | H | $CH_3$ | — | — | H | H | 0 | H | CH | |
| 285 | 2-CF$_3$ | 5-position | H | H | $CH_3$ | — | — | H | H | 0 | H | CH | |
| 286 | 2-NO$_2$ | 5-position | H | H | $CH_3$ | — | — | H | H | 0 | H | CH | |
| 287 | 3-OCH$_3$ | 5-position | H | H | $CH_3$ | — | — | H | H | 0 | H | CH | |
| 288 | — | 3-position | H | H | H | — | — | H | H | 0 | $CH_3$ | CH | |
| 289 | 2-F | 5-position | H | H | H | — | — | H | H | 0 | $CH(CH_3)_2$ | CH | |
| 290 | 2-Cl | 5-position | H | H | H | — | — | H | H | 0 | $CH_3$ | CH | mp. 107–110° C. |
| 291 | 2-Cl | 5-position | H | H | H | H | H | H | H | 1 | $CH_3$ | CH | mp. 128–130° C. |
| 292 | 2-Cl | 5-position | H | H | H | — | — | H | H | 0 | OH | CH | |
| 293 | 2-Cl | 5-position | H | H | H | — | — | H | H | 0 | $OC_2H_5$ | CH | |
| 294 | 2-Cl | 5-position | H | H | H | — | — | H | H | 0 | $OCH_2$-C$_6$H$_5$ | CH | |
| 295 | 2-Cl | 5-position | H | H | H | — | — | H | H | 0 | $CH_2OC_2H_5$ | CH | |
| 296 | 2-Cl | 5-position | H | H | H | — | — | H | H | 0 | $CH_2CH_2OC_4H_9$ | CH | |
| 297 | 2-Cl | 5-position | H | H | H | — | — | H | H | 0 | $CH_2CH_2SC_2H_5$ | CH | |
| 298 | 2-Cl | 5-position | H | H | H | — | — | H | H | 0 | $CH_2CH=CH_2$ | CH | |
| 299 | 2-Cl | 5-position | H | H | H | — | — | H | H | 0 | $CH_2CH_2CN$ | CH | |

TABLE 6-continued
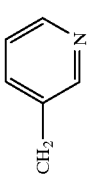
| Comp. No. | Q₁ | Bonding of the pyridine ring | R | R¹ | R² | R³ | R⁴ | R⁵ | R⁶ | n | R⁷ | Y | |
|---|---|---|---|---|---|---|---|---|---|---|---|---|---|
| 300 | — | 3-position | H | H | H | — | — | H | H | 0 | 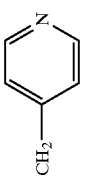 | CH | mp. 175–178° C. |
| 301 | — | 4-position | H | H | H | — | — | H | H | 0 | 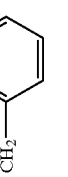 | CH | mp. 176–180° C. |
| 302 | 2-F | 5-position | H | H | H | H | H | H | H | 1 | 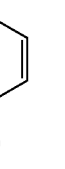 | CH | |
| 303 | 2-Cl | 5-position | H | H | H | — | — | H | H | 0 | 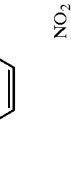 | CH | mp. 152–153° C. |
| 304 | 2-Cl | 5-position | H | H | H | — | — | H | H | 0 | 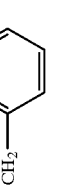 | CH | mp. 158–160° C. |
| 305 | 2-Cl | 5-position | H | H | H | — | — | H | H | 0 |  | CH | |

TABLE 6-continued

[Structure: Q₁-pyridine-CH(R)-N(R⁵R⁶)-(C)ₙ(R³R⁴)-N(R¹R²)-C(=N-R⁷)-Y-NO₂]

| Comp. No. | positions Q₁ | Bonding of the pyridine ring | R | R¹ | R² | R³ | R⁴ | R⁵ | R⁶ | n | R⁷ | Y | |
|---|---|---|---|---|---|---|---|---|---|---|---|---|---|
| 306 | 2-CH₃ | 5-position | H | H | H | — | — | H | H | 0 | -CH₂-C₆H₄-OCH₃ (4-) | CH | |
| 307 | 2-Cl | 5-position | H | H | H | — | — | H | H | 0 | -CH₂-(3-pyridyl) | CH | $n_D^{20}$ 1.6495 |
| 308 | 2-Cl | 5-position | H | H | H | — | — | H | H | 0 | -CH₂-(6-chloro-3-pyridyl) | CH | mp. 154–156° C. |
| 309 | 2-F | 5-position | H | H | H | — | — | H | H | 0 | -CH₂-(3-methylisoxazol-5-yl) | CH | |
| 310 | 2-Cl | 5-position | H | H | H | — | — | H | H | 0 | -CH₂-(1-methylpyrrol-3-yl) | CH | $n_D^{20}$ 1.6480 |
| 311 | 2-Br | 5-position | H | H | H | — | — | H | H | 0 | -CH₂-(1,2,5-thiadiazol-3-yl) | CH | |

TABLE 6-continued

[Structure: pyridine-CH(R)-N(R⁵R⁶)(Cₙ)(R³R⁴)-C(=N-NO₂)-N(R¹R²)-R⁷, with Q₁ on pyridine and Y]

| Comp. No. | positions Q₁ | Bonding of the pyridine ring | R | R¹ | R² | R³ | R⁴ | R⁵ | R⁶ | n | R⁷ | Y | |
|---|---|---|---|---|---|---|---|---|---|---|---|---|---|
| 312 | 2-Cl | 5-position | H | H | H | — | — | H | H | 0 | ![pyrazine-CH₃-CH₂] | CH | |
| 313 | 2-Cl | 5-position | H | H | H | — | — | H | H | 0 | ![pyrimidine-CH₂] | CH | |
| 314 | — | 3-position | H | H | H | — | — | H | H | 0 | H | C—Cl | |
| 315 | 2-Cl | 5-position | H | H | H | — | — | H | H | 0 | H | C—F | |
| 316 | 2-Cl | 5-position | H | H | CH₃ | — | — | H | H | 0 | H | C—Br | |
| 317 | — | 4-position | H | H | H | H | H | H | H | 1 | H | C—CH₃ | |
| 318 | 2-Cl | 5-position | H | H | H | — | — | H | H | 0 | H | C—CH₃ | |
| 319 | 2-Cl | 5-position | H | H | H | — | — | H | H | 0 | H | C—CH₂F | |
| 320 | 2-Cl | 5-position | H | H | H | — | — | H | H | 0 | H | C—CF₃ | |
| 321 | — | 3-position | H | H | H | — | — | H | H | 0 | H | C—CH₂OH | |
| 322 | 2-F | 5-position | H | H | H | — | H | H | H | 1 | H | OH<br>C—CHCCl₃ | mp. 135–140° C. |
| 323 | 2-Cl | 5-position | H | H | H | — | — | H | H | 0 | H | OH<br>C—CHCCl₃ | |

TABLE 6-continued

| Comp. No. | positions $Q_1$ | Bonding of the pyridine ring | R | $R^1$ | $R^2$ | $R^3$ | $R^4$ | $R^5$ | $R^6$ | n | $R^7$ | Y |
|---|---|---|---|---|---|---|---|---|---|---|---|---|
| 324 | 2-Cl | 5-position | H | H | H | — | — | H | H | 0 | H | (2-chloropyridin-5-yl-CH$_2$-N-tetrahydropyrimidine with CH$_2$NO$_2$ substituent); mp. 155–158° C. |
| 325 | — | 3-position | H | H | H | H | H | H | H | 1 | H | C—OH |
| 326 | 2-Cl | 5-position | H | H | H | — | — | H | H | 0 | H | C—OCH$_3$ |
| 327 | 2-Cl | 5-position | H | H | H | — | — | H | H | 0 | H | C—OCH$_2$-phenyl |
| 328 | — | 4-position | H | H | H | — | — | H | H | 0 | H | C—S—C$_3$H$_7$ |
| 329 | 2-CH$_3$ | 5-position | H | H | H | — | — | H | H | 0 | H | C—S-phenyl |
| 330 | — | 3-position | H | H | H | — | — | H | H | 0 | H | C—S(=O)$_2$—CH$_2$Cl |

TABLE 6-continued

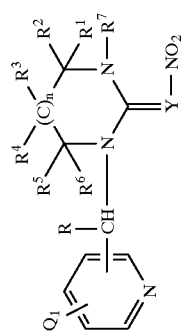

| Comp. No. | positions $Q_1$ | Bonding of the pyridine ring | R | $R^1$ | $R^2$ | $R^3$ | $R^4$ | $R^5$ | $R^6$ | n | $R^7$ | Y | |
|---|---|---|---|---|---|---|---|---|---|---|---|---|---|
| 331 | 2-Cl | 5-position | H | H | H | — | — | H | H | 0 | H | 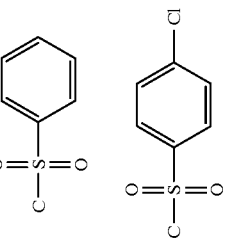 | |
| 332 | 2-CF$_3$ | 5-position | H | H | H | — | — | H | H | 0 | H | 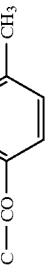 | |
| 333 | 2-Cl | 5-position | H | H | H | — | — | H | H | 0 | H | C—COCH$_3$ | mp. 102–105° C. |
| 334 | 2-F | 5-position | H | H | H | — | — | H | H | 0 | H | C—COCCl$_3$ | |
| 335 | 2-NO$_2$ | 5-position | H | H | H | — | — | H | H | 0 | H | C—COCH=CH$_2$ | |
| 336 | 2-Cl | 5-position | H | H | H | — | — | H | H | 0 | H | C—COC$_3$H$_7$ | |
| 337 | 2-Cl | 5-position | H | H | H | — | — | H | H | 0 | H | 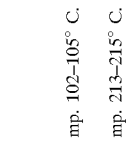 | mp. 213–215° C. |
| 338 | — | 3-position | H | H | H | H | H | H | H | 1 | H |  | |
| 339 | — | 4-position | CH$_3$ | H | H | — | — | H | H | 0 | H | C—COOCH$_3$ | mp. 169–171° C. |
| 340 | 2-Cl | 5-position | H | H | H | — | — | H | H | 0 | H | C—COOC$_2$H$_5$ | |
| 341 | 2-CN | 5-position | H | H | H | — | — | H | H | 0 | H | C—COOC$_4$H$_9$ | |

TABLE 6-continued

| Comp. No. | positions Q₁ | Bonding of the pyridine ring | R | R¹ | R² | R³ | R⁴ | R⁵ | R⁶ | n | R⁷ | Y | |
|---|---|---|---|---|---|---|---|---|---|---|---|---|---|
| 342 | 2-F | 5-position | H | H | H | — | — | H | H | 0 | H | C—COO—⟨C₆H₄⟩—CH₃ | |
| 343 | 2-Cl | 5-position | H | H | H | — | — | H | H | 0 | H | C—COO—⟨C₆H₄⟩—NO₂ | |
| 344 | 2-Cl | 5-position | H | H | H | — | — | H | H | 0 | H | C—COS—C₄H₉ | |
| 345 | 2-Cl | 5-position | H | H | H | — | — | H | H | 0 | H | C—CONHCO—⟨2-Cl-C₆H₄⟩ | |
| 346 | 2-CF₃ | 5-position | H | H | H | — | — | H | H | 0 | H | C—CONHCO—⟨2,6-F₂-C₆H₃⟩ | mp. 89–94° C. (decomp.) |
| 347 | 2,3-Cl₂ | 5-position | H | H | H | — | — | H | H | 0 | H | C—CONHS(=O)₂—CH₃ | |

TABLE 6-continued

| Comp. No. | positions Q₁ | Bonding of the pyridine ring | R | R¹ | R² | R³ | R⁴ | R⁵ | R⁶ | n | R⁷ | Y | |
|---|---|---|---|---|---|---|---|---|---|---|---|---|---|
| 348 | 2-CHF₂ | 5-position | H | H | H | — | — | H | H | 0 | H | C—CONHS(O)₂—C₆H₄—CH₃ | |
| 349 | — | 3-position | H | H | H | — | — | H | H | 0 | CH₃ | C—COCH₃ | |
| 350 | 2-Cl | 5-position | H | H | H | — | — | H | H | 0 | CH₃ | C—COC₃H₇ | |
| 351 | 2-Cl | 5-position | H | H | H | — | — | H | H | 0 | COCH₃ | C—COCH₃ | |
| 352 | 2-CH₃ | 5-position | H | H | H | — | — | H | H | 0 | Cl | C—Cl | |
| 353 | — | 3-position | H | H | H | H | H | H | H | 1 | COOC₂H₅ | C—COOC₂H₅ | |
| 354 | 2-Cl | 5-position | H | H | H | — | — | H | H | 0 | C₆H₄—COO | C—COO—C₆H₅ | mp. 100–105° C. |
| 355 | 2-CF₃ | 5-position | H | H | H | — | — | H | H | 0 | o-CH₃-C₆H₃—COO | C—COO—C₆H₄-o-CH₃ | glass |
| 356 | — | 4-position | H | H | H | — | — | H | H | 0 | C₆H₅—COS | C—COS—C₆H₅ | |
| 357 | 2-Cl | 5-position | H | H | H | — | — | H | H | 0 | C₆H₅—S | C—S—C₆H₅ | |

TABLE 6-continued

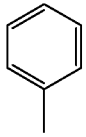

| Comp. No. | positions Q₁ | Bonding of the pyridine ring | R | R¹ | R² | R³ | R⁴ | R⁵ | R⁶ | n | R⁷ | Y | |
|---|---|---|---|---|---|---|---|---|---|---|---|---|---|
| 358 | — | 3-position | H | H | H | CH₃ | H | H | H | 1 | H | N | |
| 359 | 2-Cl | 5-position | H | H | CH₃ | — | — | H | H | 0 | H | N | |
| 360 | 2-Cl | 5-position | H | CH₃ | CH₃ | — | — | H | H | 0 | H | N | |
| 361 | 2-Cl | 5-position | H | H | H | — | — | H | H | 0 | CH₃ | N | |
| 362 | 2-SCN | 5-position | H | H | H | — | — | H | H | 0 | CH(CH₃)₂ | N | |
| 363 | 2-F | 5-position | H | H | H | — | — | H | H | 0 | CH₂CH₂Cl | N | |
| 364 | 2-Cl | 5-position | H | H | H | — | — | H | H | 0 | CH₂CH=CH₂ | N | |
| 365 | 2-Cl | 5-position | H | H | H | — | — | H | H | 0 | CH₂CCl=CCl₂ | N | |
| 366 | 2-Cl | 5-position | H | H | H | — | — | H | H | 0 | CH₂CH₂CN | N | |
| 367 | 2-F | 5-position | H | H | H | — | — | H | H | 0 | CH₂C≡CH | N | |
| 368 | 2-CF₃ | 5-position | H | H | H | H | H | H | H | 1 | CH₂CH₂N(C₂H₅)₂ | N | |
| 369 | 2-Cl | 5-position | H | H | H | — | — | H | H | 0 | CH₂OCH₃ | N | |
| 370 | — | 3-position | H | H | H | — | — | H | H | 0 | CH₂CH₂SC₂H₅ | N | |
| 371 | 2-CH₂F | 5-position | H | H | H | — | — | H | H | 0 | CH₂SC₄H₉ | N | |
| 372 | 2-Cl | 5-position | H | H | H | — | — | H | H | 0 | CH₂CN | N | |
| 373 | 2-Cl | 5-position | H | H | H | — | — | H | H | 0 | CH₂Si(CH₃)₃ | N | |
| 374 | 5-CF₃ | 2-position | H | H | H | — | — | H | H | 0 | CH₂Si(CH₃)₃ | N | |
| 375 | 2-Cl | 5-position | H | H | H | H | H | H | H | 1 | 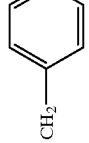 | N | $n_D^{30}$ 1.5854 |
| 376 | 2-NO₂ | 5-position | H | H | H | — | — | H | H | 0 | 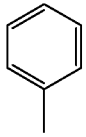 | N | |

TABLE 6-continued
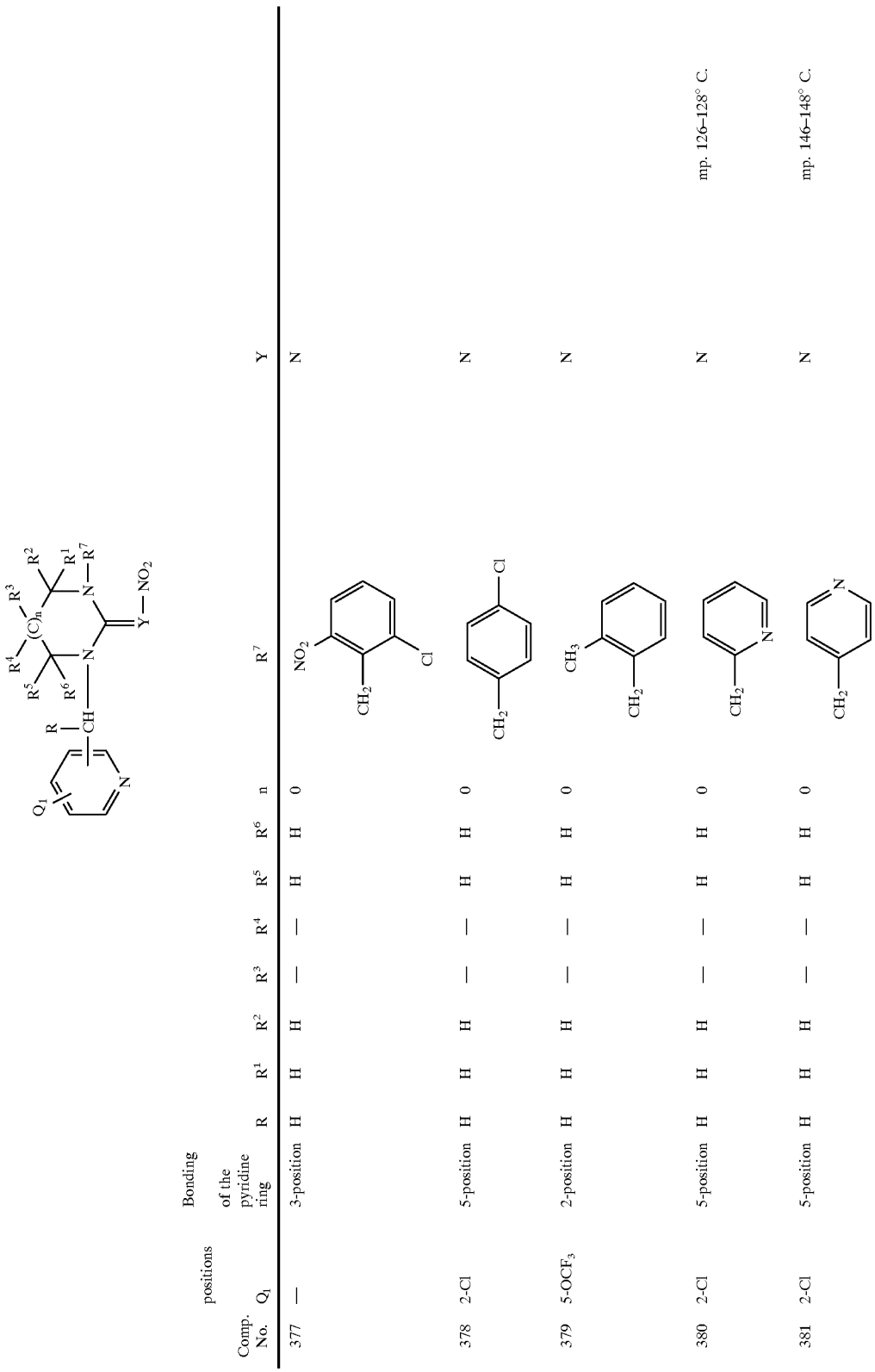
| Comp. No. | Q₁ positions | Bonding of the pyridine ring | R | R¹ | R² | R³ | R⁴ | R⁵ | R⁶ | n | R⁷ | Y | |
|---|---|---|---|---|---|---|---|---|---|---|---|---|---|
| 377 | — | 3-position | H | H | H | — | — | H | H | 0 | CH₂–(2-NO₂,3-Cl-C₆H₃) | N | |
| 378 | 2-Cl | 5-position | H | H | H | — | — | H | H | 0 | CH₂–(4-Cl-C₆H₄) | N | |
| 379 | 5-OCF₃ | 2-position | H | H | H | — | — | H | H | 0 | CH₂–(2-CH₃-C₆H₄) | N | |
| 380 | 2-Cl | 5-position | H | H | H | — | — | H | H | 0 | CH₂–(2-pyridyl) | N | mp. 126–128° C. |
| 381 | 2-Cl | 5-position | H | H | H | — | — | H | H | 0 | CH₂–(4-pyridyl) | N | mp. 146–148° C. |

TABLE 6-continued

| Comp. No. | $Q_1$ positions | Bonding of the pyridine ring | R | $R^1$ | $R^2$ | $R^3$ | $R^4$ | $R^5$ | $R^6$ | n | $R^7$ | Y | |
|---|---|---|---|---|---|---|---|---|---|---|---|---|---|
| 382 | 2-Cl | 5-position | H | H | H | — | — | H | H | 0 | $CH_2$–(6-chloropyridin-3-yl) | N | mp. 128–131° C. |
| 383 | — | 3-position | H | H | H | — | — | H | H | 0 | $CH_2$–(2,5-dimethylthiophen-yl) | N | |
| 384 | 2-$CH_3$ | 5-position | H | H | H | H | H | H | H | 1 | $CH_2$–(3-methylisoxazol-5-yl) | N | |
| 385 | 2-Cl | 5-position | H | H | H | H | H | H | H | 1 | $CH_2$–(1-methylpyrazol-yl) | N | |
| 386 | 2-Cl | 5-position | H | H | H | H | H | H | H | 1 | $CH_2$–(2-chlorothiazol-5-yl) | N | |
| 387 | 2-F | 5-position | H | H | H | — | — | H | H | 0 | $CH_2$–(1,2,4-thiadiazol-3-yl) | N | |

TABLE 6-continued structure

| Comp. No. | Q₁ | Bonding positions of the pyridine ring | R | $R^1$ | $R^2$ | $R^3$ | $R^4$ | $R^5$ | $R^6$ | n | $R^7$ | Y | |
|---|---|---|---|---|---|---|---|---|---|---|---|---|---|
| 388 | 2-Cl | 5-position | H | H | H | — | — | H | H | 0 | 2-chloropyrimidin-5-yl-CH₂ | N | |
| 389 | 2-Cl | 5-position | H | H | H | — | — | H | H | 0 | pyridazin-4-yl-CH₂ | N | |
| 390 | 2-CH₃ | 5-position | H | H | H | — | — | H | H | 0 | 2,5-dimethylpyrazin-... -CH₂ | N | |
| 391 | 2-F | 5-position | H | H | H | — | — | H | H | 0 | CH₂COCH₃ | N | |
| 392 | 2-Cl | 5-position | H | H | H | — | — | H | H | 0 | 4-Cl-C₆H₄-CH₂CO | N | |
| 393 | 2-Cl | 5-position | H | H | H | — | — | H | H | 0 | C₆H₅-OCH₂ | N | |
| 394 | — | 5-position | CH₃ | H | H | — | — | H | H | 0 | COCH₃ | N | |
| 395 | 2-Cl | 5-position | H | H | H | — | — | H | H | 0 | CHO | N | |
| 396 | 2-Cl | 5-position | H | H | H | — | — | H | H | 0 | COCH₃ | N | |
| 397 | 2-Cl | 5-position | H | H | H | H | H | H | H | 1 | COCH₃ | N | |
| 398 | 2-F | 5-position | H | H | H | — | — | H | H | 0 | COCCl₃ | N | mp. 144.5–146° C. |

TABLE 6-continued

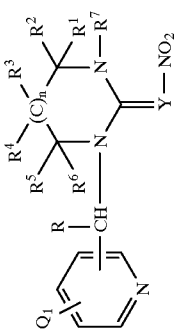

| Comp. No. | Q₁ positions | Bonding of the pyridine ring | R | R¹ | R² | R³ | R⁴ | R⁵ | R⁶ | n | R⁷ | Y |
|---|---|---|---|---|---|---|---|---|---|---|---|---|
| 399 | 2-Cl, 4-F | 5-position | H | H | H | — | — | H | H | 0 | COC₃H₇ | N |
| 400 | 2-C₂H₅ | 5-position | H | H | H | — | — | H | H | 0 | COCH₃ | N |
| 401 | 2-Cl | 5-position | H | H | H | — | — | H | H | 0 | COC(CH₃)₃ | N |
| 402 | 2-CH₃ | 5-position | H | H | H | — | — | H | H | 0 | COCH—C(CH₃)₃ with Br | N |
| 403 | 2,3-F₂ | 5-position | H | H | H | — | — | H | H | 0 | COCH₂OCH₃ | N |
| 404 | 2-Br | 5-position | H | H | H | — | — | H | H | 0 | COCH=CH₂ | N |
| 405 | 2-Cl | 5-position | H | H | H | — | — | H | H | 0 | CO-(2,4-diCl-phenyl-OCH₂O) | N |
| 406 | — | 3-position | H | H | H | — | — | H | H | 0 | CO-phenyl | N |
| 407 | — | 4-position | H | H | H | H | H | H | H | 1 | CO-(3-NO₂-phenyl) | N |

TABLE 6-continued
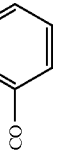
| Comp. No. | positions $Q_1$ | Bonding of the pyridine ring | R | $R^1$ | $R^2$ | $R^3$ | $R^4$ | $R^5$ | $R^6$ | n | $R^7$ | Y | |
|---|---|---|---|---|---|---|---|---|---|---|---|---|---|
| 408 | 2-Cl | 5-position | H | H | H | — | — | H | H | 0 | 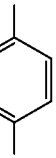 | N | mp. 146–150° C. |
| 409 | 2-F | 5-position | H | H | H | — | — | H | H | 0 | 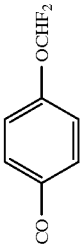 | N | mp. 149–152° C. |
| 410 | 2-Cl | 5-position | H | H | H | — | — | H | H | 0 | 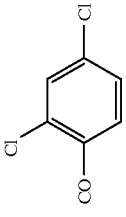 | N | |
| 411 | 2-Cl | 5-position | H | H | H | — | — | H | H | 0 | 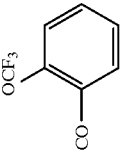 | N | |
| 412 | — | 3-position | H | H | H | — | — | H | H | 0 |  | N | |

TABLE 6-continued

| Comp. No. | positions $Q_1$ | Bonding of the pyridine ring | R | $R^1$ | $R^2$ | $R^3$ | $R^4$ | $R^5$ | $R^6$ | n | $R^7$ | Y |
|---|---|---|---|---|---|---|---|---|---|---|---|---|
| 413 | 2-CH=CCl$_2$ | 5-position | H | H | H | — | — | H | H | 0 | 2-CH$_3$-C$_6$H$_4$-CO- | N |
| 414 | 2-CF$_3$ | 5-position | H | H | H | — | — | H | H | 0 | 2,4-Cl$_2$-3-CH$_3$-C$_6$H$_2$-CO- | N |
| 415 | 2-CH$_3$ | 5-position | H | H | H | — | — | H | H | 0 | 4-OCH$_3$-C$_6$H$_4$-CO- | N |
| 416 | 2-Cl | 5-position | H | H | H | — | — | H | H | 0 | 2-CF$_3$-C$_6$H$_4$-CO- | N |
| 417 | 2-Cl | 5-position | H | H | H | — | — | H | H | 0 | 4-C(CH$_3$)$_3$-C$_6$H$_4$-CO- | N |

TABLE 6-continued

![Structure showing Q1-substituted pyridine ring connected via CHR to N(R4,R5,R6)(Cn)(R2,R3)N-R1 with C=N-Y-NO2 and R7]

| Comp. No. | positions Q₁ | Bonding of the pyridine ring | R | R¹ | R² | R³ | R⁴ | R⁵ | R⁶ | n | R⁷ | Y |
|---|---|---|---|---|---|---|---|---|---|---|---|---|
| 418 | 2-Cl | 5-position | H | H | H | — | — | H | H | 0 | COCH₂-C₆H₅ | N |
| 419 | — | 3-position | H | H | H | H | H | H | H | 1 | 2-furyl-CO | N |
| 420 | 2-F | 5-position | H | H | H | — | — | H | H | 0 | 5-Br-2-furyl-CO | N |
| 421 | 2-CH₃ | 5-position | H | H | H | — | — | H | H | 0 | 2-thienyl-CO | N |
| 422 | 2-Cl | 5-position | H | H | H | — | — | H | H | 0 | 2-methyl-thiazolyl-CO | N |
| 423 | 2,6-Cl₂ | 4-position | H | H | H | — | — | H | H | 0 | 2-pyridyl-CO | N |

TABLE 6-continued

Structure:

$$Q_1\text{-pyridine-CH}(R)\text{-N}(R^6)(R^5)\text{-C}(R^4)_n\text{-N}(R^3)(R^2,R^1)\text{-N}(R^7)=\text{Y-NO}_2$$

| Comp. No. | positions $Q_1$ | Bonding of the pyridine ring | R | $R^1$ | $R^2$ | $R^3$ | $R^4$ | $R^5$ | $R^6$ | n | $R^7$ | Y | |
|---|---|---|---|---|---|---|---|---|---|---|---|---|---|
| 424 | 2-Cl | 5-position | H | H | H | — | — | H | H | 0 | 2-chloropyridin-5-yl | N | mp. 118–122° C. |
| 425 | 2-Cl | 5-position | H | H | H | — | — | H | H | 0 | 2-chloropyrimidin-5-yl | N | |
| 426 | — | 3-position | H | H | H | H | CH$_3$ | H | H | 1 | COOCH$_3$ | N | |
| 427 | 2-F | 5-position | H | H | H | — | — | H | H | 0 | COOC$_2$H$_5$ | N | |
| 428 | 2-Cl | 5-position | H | H | H | — | — | H | H | 0 | COOC$_2$H$_5$ | N | mp. 125–126° C. |
| 429 | 2-CH$_3$ | 5-position | H | H | H | — | — | H | H | 0 | COOC$_4$H$_9$ | N | |
| 430 | 2-Cl | 5-position | H | H | H | — | — | H | H | 0 | COOCH$_2$CF$_3$ | N | |
| 431 | 2-Cl | 5-position | H | H | H | — | — | H | H | 0 | phenyl-OCO- | N | mp. 135–140° C. |
| 432 | 2-Cl | 5-position | CH$_3$ | H | H | — | — | H | H | 0 | 4-methylphenyl-OCO- | N | |
| 433 | 2-Cl | 5-position | H | H | H | — | — | H | H | 0 | 2,4-dichlorophenyl-OCO- | N | |

TABLE 6-continued

[Structure: pyridine ring with Q₁ substituent, connected via CH(R) to N, forming a ring with R¹-R⁶ substituents and (C)ₙ, with C(=Y-NO₂)-N-R⁷ group]

| Comp. No. | positions Q₁ | Bonding of the pyridine ring | R | R¹ | R² | R³ | R⁴ | R⁵ | R⁶ | n | R⁷ | Y | |
|---|---|---|---|---|---|---|---|---|---|---|---|---|---|
| 434 | 2-CHF₂ | 5-position | H | H | H | — | — | H | H | 0 | 4-Cl-C₆H₄-COOCH₂- | N | |
| 435 | 2-Cl | 5-position | H | H | H | — | — | H | H | 0 | COSC₂H₅ | N | |
| 436 | 2-Cl | 5-position | H | H | H | — | — | H | H | 0 | 2-CH₃-C₆H₄-COS- | N | |
| 437 | 2,3-F₂ | 5-position | H | H | H | — | — | H | H | 0 | CH₃SO₂- | N | |
| 438 | 2-Cl | 5-position | H | H | H | — | — | H | H | 0 | CH₃SO₂- | N | |
| 439 | 2-Cl | 5-position | H | H | H | — | — | H | H | 0 | ClCH₂SO₂- | N | mp. 191–192° C. |

TABLE 6-continued
| Comp. No. | Q₁ | Bonding positions of the pyridine ring | R | R¹ | R² | R³ | R⁴ | R⁵ | R⁶ | n | R⁷ | Y | |
|---|---|---|---|---|---|---|---|---|---|---|---|---|---|
| 440 | 2-Cl | 5-position | H | H | H | — | — | H | H | 0 | S(=O)(=O)CH₂CH₂Cl | N | |
| 441 | 2-COOCH₃ | 6-position | H | H | H | — | — | H | H | 0 | S(=O)(=O)-phenyl | N | |
| 442 | 2-Cl | 5-position | H | H | H | — | — | H | H | 0 | S(=O)(=O)-(4-Cl-phenyl) | N | |
| 443 | 2-Cl | 5-position | H | H | H | — | — | H | H | 0 | S(=O)(=O)-(2-CH₃-5-NO₂-phenyl) | N | |
| 444 | 2-Cl | 5-position | H | H | H | — | — | H | H | 0 | CON(CH₃)₂ | N | mp. 186–188° C. |

TABLE 6-continued

Structure: pyridine ring with Q₁ substituent, connected via R-CH to N-C(=Y-NO₂)-N-R⁷ with R¹-R⁶ substituents and (C)ₙ bridge.

| Comp. No. | positions Q₁ | Bonding of the pyridine ring | R | R¹ | R² | R³ | R⁴ | R⁵ | R⁶ | n | R⁷ | Y | |
|---|---|---|---|---|---|---|---|---|---|---|---|---|---|
| 445 | 2-Cl | 5-position | H | H | H | — | — | H | H | 0 | 3-Cl-C₆H₄-CONH- | N | mp. 120–123° C. |
| 446 | 2-F | 5-position | H | H | H | — | — | H | H | 0 | 4-CH₃-C₆H₄-N(CH₃)CO- | N | |
| 447 | 2-Cl, 6-F | 5-position | H | H | H | — | — | H | H | 0 | C₆H₅-CONHCO- | N | |
| 448 | 2-CN | 5-position | H | H | H | — | — | H | H | 0 | 2,6-Cl₂-C₆H₃-CONHCO- | N | |
| 449 | — | 4-position | H | H | H | H | H | H | H | 1 | CH₃-SO₂-NHS(=O)(=O)-CH₃ | N | |

TABLE 6-continued
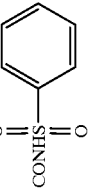
| Comp. No. | positions Q₁ | Bonding of the pyridine ring | R | R¹ | R² | R³ | R⁴ | R⁵ | R⁶ | n | R⁷ | Y | |
|---|---|---|---|---|---|---|---|---|---|---|---|---|---|
| 450 | 2-Cl | 5-position | H | H | H | — | — | H | H | 0 | 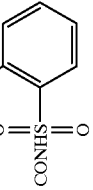 | N | |
| 451 | 2-Cl | 5-position | H | H | H | — | — | H | H | 0 |  | N | |
| 452 | — | 3-position | H | H | H | — | — | H | H | 0 |  | N | $n_D^{24}$ 1.5760 |
| 453 | 2-Cl | 5-position | H | H | H | — | — | H | H | 0 | 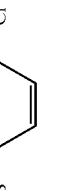 | N | $n_D^{20}$ 1.5615 |
| 454 | 2-Cl | 5-position | H | H | H | — | — | H | H | 0 |  | N | |
| 455 | 2-Cl | 5-position | H | H | H | — | — | H | H | 0 |  | N | |

TABLE 6-continued
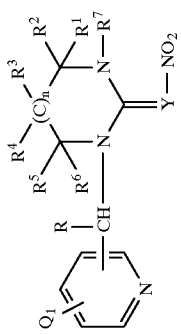
| Comp. No. | positions Q₁ | Bonding of the pyridine ring | R | R¹ | R² | R³ | R⁴ | R⁵ | R⁶ | n | R⁷ | Y |
|---|---|---|---|---|---|---|---|---|---|---|---|---|
| 456 | 2-Cl | 5-position | H | H | — | H | H | — | H | 1 | H | CH |

In addition to table 5, there follow: the case (table 7) where the formula (I) represents the following formula;

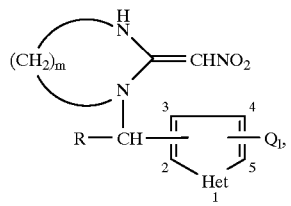

the case (table 8) where the formula (I) represents the following formula;

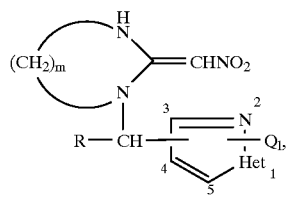

the case (table 9) where the formula (I) represents the following formula;

the case (table 10) where the formula (I) represents the following formula;

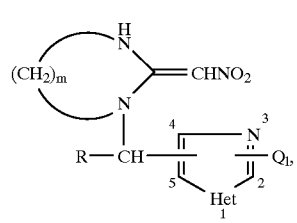

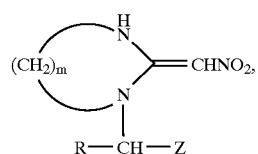

TABLE 7

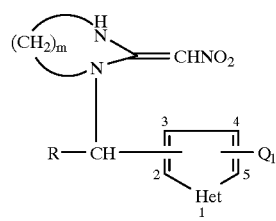

| Compound No. | Het | Bonding potition of the heterocycle | $Q_1$ | R | m | |
|---|---|---|---|---|---|---|
| 457 | O | 2 | — | H | 2 | |
| 458 | O | 2 | — | H | 3 | mp. 194~196° C. |
| 459 | O | 3 | — | H | 3 | |
| 460 | S | 2 | — | H | 2 | |
| 461 | S | 2 | — | H | 3 | mp. 189~190° C. |
| 462 | S | 3 | — | H | 3 | mp. 196~198° C. |
| 463 | S | 3 | — | —$CH_3$ | 2 | |
| 464 | N | 2 | 1-H | H | 2 | mp. 201~205° C. |
| 465 | N | 2 | 1-H | H | 3 | mp. 183~185° C. |
| 466 | N | 3 | 1-H | H | 3 | |
| 467 | N | 2 | 1-$CH_3$ | H | 2 | |
| 468 | N | 2 | 1-$CH_3$ | H | 3 | mp. 207~213° C. |
| 469 | N | 2 | 1-$C_2H_5$ | H | 2 | |
| 470 | N | 3 | 1-$CH_3$ | H | 3 | |
| 471 | O | 2 | 5-$CH_3$ | H | 2 | mp. 151~152° C. |
| 472 | O | 2 | 5-$CH_3$ | H | 3 | |
| 473 | O | 3 | 5-$CH_3$ | H | 2 | |
| 474 | S | 2 | 5-$CH_3$ | H | 2 | |
| 475 | S | 3 | 5-$CH_3$ | H | 3 | |
| 476 | N | 3 | 1-H, 5-$CH_3$ | H | 3 | |
| 477 | N | 2 | 1-H, 5-$CH_3$ | H | 2 | |
| 478 | O | 3 | 2,5-$(CH_3)_2$ | H | 3 | |
| 479 | S | 3 | 2,5-$(CH_3)_2$ | H | 3 | |
| 480 | O | 3 | 5-F | H | 2 | |
| 481 | O | 2 | 4-Cl | H | 2 | |
| 482 | O | 2 | 5-Cl | H | 2 | mp. 130~131° C. |
| 483 | O | 3 | 5-Cl | H | 3 | |
| 484 | S | 3 | 5-Cl | H | 2 | |
| 485 | N | 3 | 1-$CH_3$, 5-Cl | H | 3 | |
| 486 | O | 3 | 5-Br | H | 2 | |
| 487 | S | 2 | 5-Br | H | 3 | mp. 184~186° C. |

TABLE 7-continued

[Structure: (CH2)m-N(H)-N=CHNO2 ring attached to N-CH(R)-Het1 ring with positions 2,3,4,5 and Q1]

| Compound No. | Het | Bonding position of the heterocycle | Q₁ | R | m | |
|---|---|---|---|---|---|---|
| 488 | O | 2 | 4,5-Cl₂ | H | 2 | |
| 489 | S | 3 | 4,5-Cl₂ | H | 2 | |
| 490 | S | 2 | 4,5-Br₂ | H | 2 | |
| 491 | O | 2 | 5-NO₂ | H | 2 | |
| 492 | S | 2 | 4-NO₂ | H | 3 | |
| 493 | S | 2 | 5-NO₂ | H | 2 | |
| 494 | N | 3 | 1-CH₃, 5-NO₂ | H | 3 | |
| 495 | O | 2 | 5-CN | H | 2 | mp. 212~215° C. |
| 496 | O | 3 | 5-CN | H | 3 | |
| 497 | S | 3 | 5-CN | H | 2 | |
| 498 | N | 3 | 1-CH₃, 5-CN | H | 2 | |
| 499 | O | 2 | 5-CF₃ | H | 2 | |
| 500 | O | 2 | 5-CHF₂ | H | 3 | |
| 501 | S | 3 | 5-CF₂ | H | 3 | |
| 502 | N | 3 | 1-CH₃, 5-CF₃ | H | 2 | |
| 503 | S | 2 | 5-OCH₃ | H | 2 | |
| 504 | O | 2 | 5-SCH₃ | H | 3 | |
| 505 | S | 3 | 2,5-(SCH₃)₂ | H | 2 | |
| 506 | O | 2 | 5-SCF₃ | H | 2 | mp. 143~144° C. |
| 507 | O | 2 | 5-SCF₃ | H | 3 | mp. 120~124° C. |
| 508 | S | 2 | 5-CH=CCl₂ | H | 2 | |
| 509 | O | 2 | 5-O-phenyl | H | 2 | mp. 127~129° C. |
| 510 | O | 2 | 5-COOC₂H₅ | H | 2 | |
| 511 | S | 2 | 5-CHO | H | 2 | |
| 512 | S | 2 | 4-CH₃ | —CH₃ | 2 | mp. 170~171.5° C. |

TABLE 8

[Structure: (CH2)m-N(H)-N=CHNO2 ring attached to N-CH(R)-Het1 ring with positions 3,4,5 and N at position 2, Q1]

| Compound No. | Het | Bonding position of the hetero-cycle | Q₁ | R | m | |
|---|---|---|---|---|---|---|
| 513 | O | 3 | — | H | 3 | |
| 514 | O | 4 | — | H | 2 | |
| 515 | O | 4 | — | H | 3 | |
| 516 | O | 4 | — | —CH₃ | 2 | |
| 517 | O | 5 | — | H | 3 | |
| 518 | O | 3 | 5-CH₃ | H | 3 | mp. 186~188° C. |
| 519 | O | 5 | 3-CH₃ | H | 3 | mp. 200~201° C. |
| 520 | O | 5 | 3-C₂H₅ | H | 2 | |
| 521 | O | 5 | 3-C₃H₇-iso | H | 2 | |
| 522 | O | 5 | 3-F | H | 3 | |
| 523 | O | 5 | 3-Cl | H | 2 | |
| 524 | O | 5 | 3-Br | H | 2 | |

TABLE 8-continued

| Compound No. | Het | Bonding position of the heterocycle | Q₁ | R | m | |
|---|---|---|---|---|---|---|
| 525 | O | 5 | 3-OH | H | 2 | |
| 526 | O | 5 | 3-NO₂ | H | 3 | |
| 527 | O | 5 | 3-CN | H | 3 | |
| 528 | O | 5 | 3-CF₃ | H | 2 | |
| 529 | O | 5 | 3-CF₃ | H | 3 | mp. 177~180° C. |
| 530 | O | 5 | 3-CHF₂ | H | 2 | |
| 531 | O | 5 | 3-CF₂Cl | H | 2 | |
| 532 | O | 5 | 3-CH₂Cl | H | 2 | |
| 533 | O | 5 | 3-CH₂OCH₃ | H | 2 | |
| 534 | O | 5 | 3-CH₂OCH(CH₃)₂ | H | 2 | |
| 535 | O | 5 | 3-CCl₃ | H | 2 | |
| 536 | O | 5 | 3-OCH₃ | H | 3 | |
| 537 | O | 5 | 3-OCF₃ | H | 2 | |
| 538 | O | 4 | 2,5-(CH₃)₂ | H | 2 | |
| 539 | S | 3 | — | H | 3 | |
| 540 | S | 4 | — | H | 2 | |
| 541 | S | 5 | — | H | 2 | |
| 542 | S | 3 | 5-CH₃ | H | 3 | |
| 543 | S | 5 | 3-CH₃ | H | 2 | |
| 544 | S | 5 | 3-F | H | 2 | |
| 545 | S | 3 | 5-Cl | H | 2 | |
| 546 | S | 5 | 3-Cl | H | 2 | |
| 547 | S | 3 | 5-Br | H | 2 | |
| 548 | S | 5 | 3-NO₂ | H | 3 | |
| 549 | S | 5 | 3-SCF₃ | H | 2 | |
| 550 | N | 5 | 1-H | H | 2 | mp. 190~193° C. |
| 551 | N | 5 | 1-H | H | 3 | |
| 552 | N | 4 | 1-H | H | 2 | mp. 196~198° C. |
| 553 | N | 4 | 1-H | —CH₃ | 2 | |
| 554 | N | 4 | 1-H | H | 3 | mp. 222~225° C. |
| 555 | N | 3 | 1-CH₃ | H | 2 | mp. 212~215° C. |
| 556 | N | 4 | 1-CH₃ | H | 2 | mp. 179~180° C. |
| 557 | N | 4 | 1-CH₃ | —CH₃ | 3 | |
| 558 | N | 5 | 1-CH₃ | H | 2 | |
| 559 | N | 4 | 1-C₂H₅ | H | 2 | |
| 560 | N | 4 | 1-C₂H₅ | H | 3 | mp. 145~148° C. |
| 561 | N | 4 | 1-C₃H₇ | H | 3 | mp. 99~101° C. |
| 562 | N | 4 | 1-C₃H₇-iso | H | 2 | |
| 563 | N | 4 | 1-C₃H₇-iso | H | 3 | mp. 136~137° C. |
| 564 | N | 4 | 1-CH₂CH=CH₂ | H | 3 | mp. 109~112° C. |
| 565 | N | 4 | 1-CHC≡CH | H | 2 | |
| 566 | N | 4 | 1-C₄H₉-tert | H | 2 | mp. 126~128° C. |
| 567 | N | 4 | 1-C₄H₉-tert | H | 3 | mp. 153~156° C. |
| 568 | N | 4 | 1-C₆H₅ | H | 2 | mp. 151~153° C. |
| 569 | N | 4 | 1-C₆H₅ | H | 3 | mp. 177~180° C. |
| 570 | N | 4 | 1-CH₂-C₆H₅ | H | 2 | mp. 111~113° C. |

TABLE 8-continued

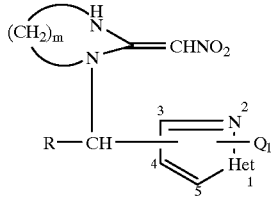

| Compound No. | Het | Bonding position of the heterocycle | Q₁ | R | m | |
|---|---|---|---|---|---|---|
| 571 | N | 4 | 1-CH₂-(phenyl) | H | 3 | mp. 159~163° C. |
| 572 | N | 4 | 1-CF₃ | H | 2 | |
| 573 | N | 3 | 1-CH₂CF₃ | H | 2 | |
| 574 | N | 4 | 1-CH₂CF₃ | H | 2 | |
| 575 | N | 5 | 1-H, 3-CH₃ | H | 2 | mp. 183~185° C. |
| 576 | N | 5 | 1-H, 3-CH₃ | H | 3 | |
| 577 | N | 3 | 1-H, 5-Cl | H | 2 | |
| 578 | N | 3 | 1-CH₃, 5-F | H | 2 | |
| 579 | N | 3 | 1-CH₃, 5-Cl | H | 2 | mp. 195~198° C. |
| 580 | N | 3 | 1-CH₃, 5-Cl | H | 3 | mp. 222~224° C. |
| 581 | N | 3 | 1-C₂H₅, 5-Cl | H | 2 | |
| 582 | N | 3 | 1-C₃H₇-iso, 5-Cl | H | 2 | |
| 583 | N | 5 | 1-CH₃, 5-Cl | H | 2 | |
| 584 | N | 3 | 1-H, 5-CF₃ | H | 2 | |
| 585 | N | 3 | 1-CH₃, 5-CF₃ | H | 2 | |
| 586 | N | 5 | 1-CH₃, 5-CF₃ | H | 2 | |
| 587 | N | 4 | 1,3,5-(CH₃)₃ | H | 3 | mp. 192~194° C. |
| 588 | N | 5 | 1-CH₂CF₃ | H | 2 | mp. 165~168° C. |

TABLE 9

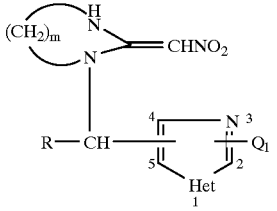

| Compound No. | Het | Bonding position of the heterocycle | Ql | R | m | |
|---|---|---|---|---|---|---|
| 589 | O | 4 | — | H | 2 | |
| 590 | O | 5 | — | H | 2 | |
| 591 | O | 5 | — | H | 3 | |
| 592 | O | 4 | 2-CH₃ | H | 2 | |
| 593 | O | 5 | 2-CH₃ | H | 2 | |
| 594 | O | 5 | 2-CH₃ | H | 3 | |
| 595 | O | 5 | 4-CH₃ | H | 2 | mp. 200~202° C. |
| 596 | O | 5 | 4-CH₃ | H | 3 | mp. 221~224° C. |
| 597 | O | 5 | 2-F | H | 2 | |
| 598 | O | 5 | 2-Cl | H | 2 | |
| 599 | O | 5 | 2-Cl | H | 3 | |
| 600 | O | 5 | 2-CF₃ | H | 2 | |
| 601 | O | 5 | 2-SCF₃ | H | 2 | |
| 602 | O | 5 | 2-OCF₃ | H | 2 | |
| 603 | O | 5 | 2,4-(CH₃)₂ | H | 2 | |
| 604 | O | 2 | 5-COOC₂H₅ | H | 3 | |
| 605 | S | 4 | — | H | 2 | mp. 213~216° C. |
| 606 | S | 4 | — | H | 3 | mp. 181~183° C. |
| 607 | S | 5 | — | H | 2 | mp. 169~174° C. |
| 608 | S | 5 | — | —CH₃ | 2 | |

TABLE 9-continued $$\begin{array}{c} (CH_2)_m \overset{H}{\underset{N}{\bigcap}} \\ \underset{R-CH}{\overset{}{\bigcap}} \overset{4}{\underset{5}{\bigcap}} \overset{N}{\underset{Het}{\bigcap}} \overset{3}{\underset{1}{\bigcap}} Q_1 \end{array}$$

| Compound No. | Het | Bonding position of the heterocycle | Ql | R | m | |
|---|---|---|---|---|---|---|
| 609 | S | 5 | — | —$C_3H_7$-iso | 2 | |
| 610 | S | 5 | — | H | 3 | |
| 611 | S | 4 | 2-$CH_3$ | H | 2 | mp. 170~172° C. |
| 612 | S | 4 | 2-$CH_3$ | H | 3 | mp. 203~206° C. |
| 613 | S | 5 | 2-$CH_3$ | H | 2 | mp. 162~166° C. |
| 614 | S | 5 | 2-$CH_3$ | —$CH_3$ | 2 | |
| 615 | S | 5 | 2-$CH_3$ | —$CH_3$ | 3 | |
| 616 | S | 5 | 2-$C_2H_5$ | H | 2 | |
| 617 | S | 5 | 2-$C_3H_7$-iso | H | 3 | |
| 618 | S | 5 | 4-$CH_3$ | H | 2 | |
| 619 | S | 4 | 2-F | H | 2 | |
| 620 | S | 4 | 2-Cl | H | 2 | mp. 162~165° C. |
| 621 | S | 4 | 2-Cl | H | 3 | mp. 190~194° C. |
| 622 | S | 5 | 2-F | H | 3 | |
| 623 | S | 5 | 2-Cl | H | 2 | mp. 191~192° C. |
| 624 | S | 5 | 2-Cl | H | 3 | mp. 203~205° C. |
| 625 | S | 5 | 2-Cl | —$CH_3$ | 3 | |
| 626 | S | 5 | 2-Cl | —$C_2H_5$ | 3 | |
| 627 | S | 5 | 2,4-$Cl_2$ | H | 2 | mp. 179~181° C. |
| 628 | S | 4 | 2-$NO_2$ | H | 2 | |
| 629 | S | 5 | 2-$NO_2$ | H | 3 | |
| 630 | S | 4 | 2-CN | H | 2 | |
| 631 | S | 5 | 2-CN | H | 2 | |
| 632 | S | 4 | 2-$SCH_3$ | H | 3 | |
| 633 | S | 5 | 2-SH | H | 2 | |
| 634 | S | 5 | 2-$SCH_3$ | H | 3 | |
| 635 | S | 5 | 2-$SCHF_2$ | H | 2 | |
| 636 | S | 5 | 2-$SCF_3$ | H | 2 | |
| 637 | S | 5 | 2-$SCF_2Cl$ | H | 2 | |
| 638 | S | 5 | 2-$SCH_2CF_3$ | H | 2 | |
| 639 | S | 5 | 2-$SCH_2C(Cl)=CCl_2$ | H | 2 | |
| 640 | S | 5 | 2-SCN | H | 2 | |
| 641 | S | 4 | 2-$NH_2$ | H | 2 | mp. 165~167° C. |
| 642 | S | 4 | 2-$NHCOCH_3$ | H | 2 | |
| 643 | S | 4 | 2-$OCH_3$ | H | 3 | |
| 644 | S | 5 | 2-$OCH_3$ | H | 3 | |
| 645 | S | 5 | 2-$OCF_3$ | H | 2 | |
| 646 | S | 5 | 2-$OCHF_2$ | H | 3 | |
| 647 | S | 5 | 2-$CH_2Cl$ | H | 2 | |
| 648 | S | 5 | 2-$CHF_2$ | H | 2 | |
| 649 | S | 5 | 2-$CF_3$ | H | 2 | |
| 650 | S | 5 | 2-$CF_3$ | H | 3 | |
| 651 | S | 5 | 2-$CF_2CHF_2$ | H | 2 | |
| 652 | S | 5 | 2-cyclopropyl | H | 3 | |
| 653 | S | 4 | 2-phenyl | H | 2 | mp. 169~172° C. |

TABLE 9-continued
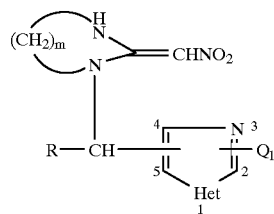
| Compound No. | Het | Bonding position of the heterocycle | Ql | R | m | |
|---|---|---|---|---|---|---|
| 654 | S | 4 | 2-[phenyl] | H | 3 | mp. 158~159° C. |
| 655 | N | 2 | 1-H | H | 2 | mp. 239~240° C. |
| 656 | N | 4 | 1-H | H | 2 | |
| 657 | N | 4 | 1-H | H | 3 | mp. 169~173° C. |
| 658 | N | 2 | 1-$CH_3$ | H | 2 | mp. 248~252° C. |
| 659 | N | 5 | 1-$CH_3$ | H | 2 | |
| 660 | N | 2 | 1-$CH_2$-[phenyl] | H | 2 | mp. 142~145° C. |
| 661 | N | 5 | 1-H, 4-$CH_3$ | H | 2 | |
| 662 | N | 4 | 1-H, 2-F | H | 3 | |
| 663 | N | 4 | 1-H, 2-Cl | H | 2 | |
| 664 | N | 2 | 1-H, 4-$NO_2$ | H | 2 | |
| 665 | N | 4 | 1-H, 2-$SCF_3$ | H | 2 | |
| 666 | N | 4 | 1,2-$(CH_3)_2$ | H | 2 | |
| 667 | N | 4 | 1-$CH_3$, 2-$CF_3$ | H | 2 | |
| 668 | O | 2 | 5-COOH | H | 3 | |
| 669 | S | 5 | 2-$NHCH_3$ | H | 2 | |
| 670 | S | 5 | 2-$NI(CH_3)_2$ | H | 3 | mp. 188~191° C. |
| 671 | S | 5 | 2-NHCOCF$_3$ | H | 2 | |
| 672 | S | 5 | 2-$CH_3$ | H | 4 | |
| 673 | S | 2 | 5-$CONH_2$ | H | 2 | |
| 674 | S | 2 | 5-$CONHCH_3$ | H | 2 | |
| 675 | S | 2 | 5-$CON(CH_3)_2$ | H | 3 | |
| 676 | S | 5 | 2-$SOCH_3$ | H | 2 | |
| 677 | S | 5 | 2-$SO_2CH_3$ | H | 2 | |
| 678 | S | 5 | 2-$N(CH_3)_2$ | H | 2 | mp. 149~150° C. |
| 679 | S | 5 | 2-$SCH_3$ | H | 2 | mp. 150~153° C. |
| 680 | S | 5 | 2-Br | H | 3 | |

TABLE 10
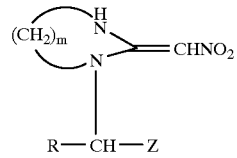
| Compound No. | Z | R | m | |
|---|---|---|---|---|
| 681 | 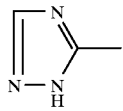 | H | 2 | mp. 206~210° C. |
| 682 | 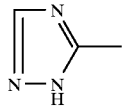 | H | 3 | |
| 683 | 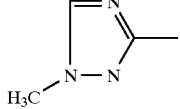 | H | 2 | mp. 265~267° C. |
| 684 | 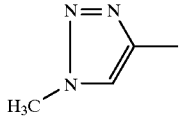 | H | 2 | |
| 685 | 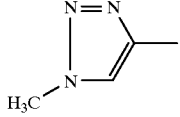 | H | 3 | |
| 686 | 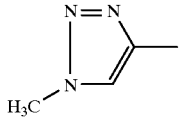 | —CH$_3$ | 2 | |
| 687 | 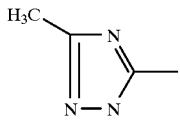 | H | 2 | |
| 688 | 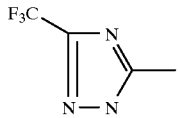 | H | 2 | |
| 689 | 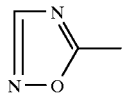 | H | 2 | |
| 690 | 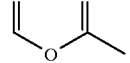 | H | 3 | |

TABLE 10-continued
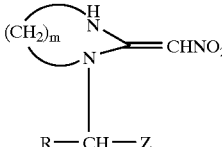
| Compound No. | Z | R | m | |
|---|---|---|---|---|
| 691 | 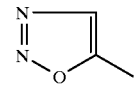 | H | 2 | |
| 692 | 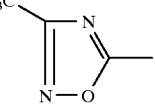 | H | 2 | mp. 221~225° C. |
| 693 | 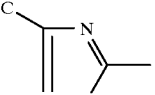 | H | 2 | |
| 694 | 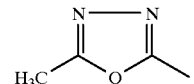 | H | 2 | mp. 178~180° C. |
| 695 | 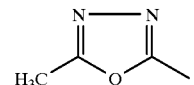 | H | 3 | |
| 696 | 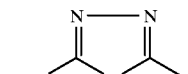 | H | 2 | |
| 697 | 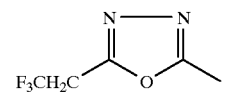 | H | 2 | |
| 698 | 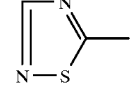 | H | 2 | |
| 699 | 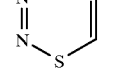 | H | 2 | |
| 700 | 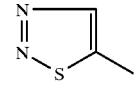 | H | 2 | |
| 701 | 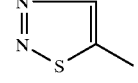 | H | 3 | |
| 702 | 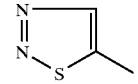 | —CH$_3$ | 2 | |

TABLE 10-continued
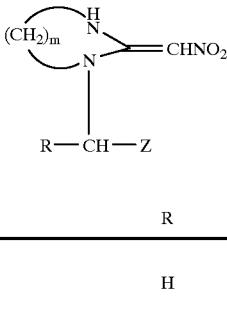
| Compound No. | Z | R | m | |
|---|---|---|---|---|
| 703 |  | H | 2 | |
| 704 |  | —CH₃ | 3 | |
| 705 |  | H | 2 | mp. 188~190° C. |
| 706 | 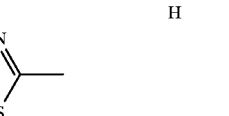 | H | 3 | mp. 207~210° C. |
| 707 | 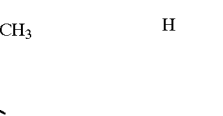 | H | 2 | |
| 708 | 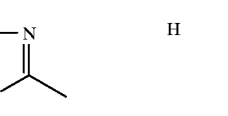 | H | 2 | |
| 709 | 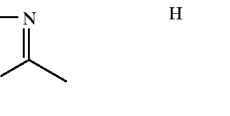 | H | 2 | |
| 710 |  | H | 3 | |
| 711 | 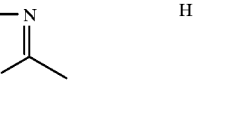 | H | 2 | |
| 712 |  | H | 2 | |
| 713 | | H | 2 | |

TABLE 10-continued
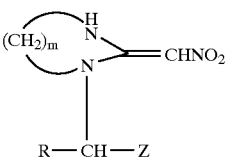
| Compound No. | Z | R | m |
|---|---|---|---|
| 714 | 3-chloro-5-methyl-1,2,4-oxadiazol-yl | H | 2 |
| 715 | 2-methylthio-5-methyl-1,3,4-thiadiazol-yl | H | 2 |
| 716 | 2-methylsulfonyl-5-methyl-1,3,4-thiadiazol-yl | H | 2 |
| 717 | 2-methyl-5-methyl-2H-tetrazol-yl | H | 2 |
| 718 | tetrahydrofuran-2-yl | H | 2 mp. 163~166° C. |
| 719 | 2,5-dimethyltetrahydrofuran-yl | H | 2 |
| 720 | tetrahydrofuran-3-yl | H | 3 |
| 721 | tetrahydrofuran-3-yl | —CH₃ | 3 |
| 722 | tetrahydrothiophen-3-yl | H | 2 |
| 723 | tetrahydrothiophen-3-yl | —CH₃ | 2 |

TABLE 10-continued
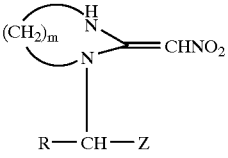
| Compound No. | Z | R | m | |
|---|---|---|---|---|
| 724 | 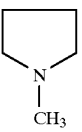 | H | 2 | |
| 725 |  | H | 3 | |
| 726 | 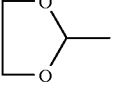 | H | 3 | mp. 144~148° C. |
| 727 | 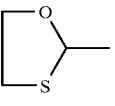 | H | 2 | |
| 728 | 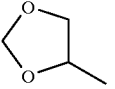 | H | 3 | |
| 729 | 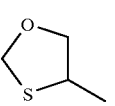 | H | 2 | |
| 730 | 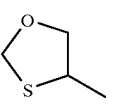 | H | 3 | |
| 731 | 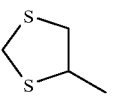 | H | 3 | |
| 732 | 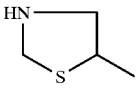 | H | 2 | |
| 733 | 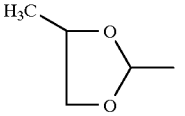 | H | 2 | |
| 734 | 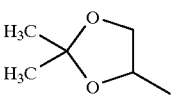 | H | 2 | mp. 142~143° C. |

TABLE 10-continued
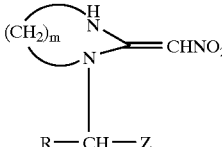
| Compound No. | Z | R | m |
|---|---|---|---|
| 735 | 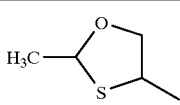 | H | 2 |
| 736 | 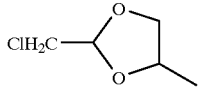 | H | 3 |
| 737 | 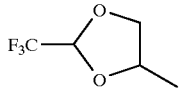 | H | 2 |
| 738 | 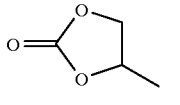 | H | 2 |
| 739 | 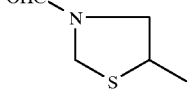 | H | 2 |
| 740 | 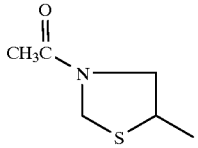 | H | 3 |
| 741 | 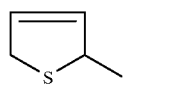 | H | 2 |
| 742 | 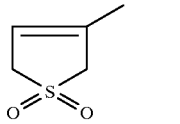 | H | 2 |
| 743 | 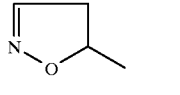 | H | 2 |
| 744 | 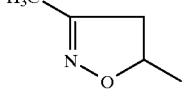 | H | 2 mp. 212~215° C. |
| 745 | 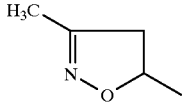 | H | 3 |

TABLE 10-continued
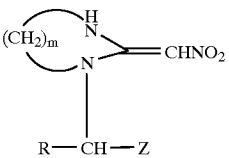
| Compound No. | Z | R | m |
|---|---|---|---|
| 746 | 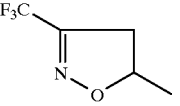 | H | 2 |
| 747 | 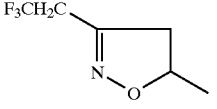 | H | 2 |
| 748 | 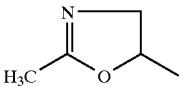 | H | 3 |
| 749 | 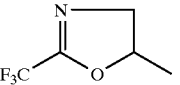 | H | 2 |
| 750 | 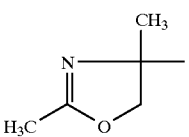 | H | 2 |
| 751 | 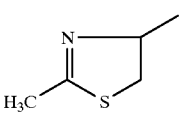 | H | 2 |
| 752 | 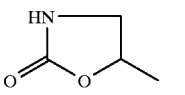 | H | 2 |
| 753 | 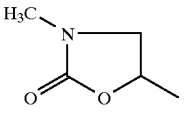 | H | 2 |
| 754 | 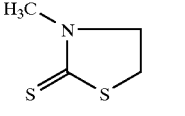 | H | 2 |
| 755 | 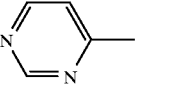 | H | 2  m.p. 185–187° C. |

TABLE 10-continued

| Compound No. | Z | R | m | |
|---|---|---|---|---|
| 756 | 2,4-dimethylpyrimidin-... (2-CH₃, 4-yl pyrimidine) | H | 2 | m.p. 216–217° C. |
| 757 | 2-methyl-6-methyl-4-oxo-1,2-dihydropyrimidin-... | H | 3 | |
| 758 | 2-methylpyrimidin-5-yl | H | 2 | m.p. 188–189° C. |
| 759 | 2-(dimethylamino)pyrimidin-5-yl | H | 2 | m.p. 200–203° C. |
| 760 | 2-(dimethylamino)pyrimidin-5-yl | H | 3 | m.p. 219–222° C. |
| 761 | 2,4,6-trichloro-5-methylpyrimidin-... | H | 2 | |
| 762 | pyrazin-2-yl | H | 2 | m.p. 259–260° C. |
| 763 | pyrazin-2-yl | —CH₃ | 2 | m.p. 173–174° C. |
| 764 | pyridazin-3-yl | H | 2 | m.p. 216–218° C. |
| 765 | 2-chloropyrimidin-4-yl | H | 2 | |

TABLE 10-continued
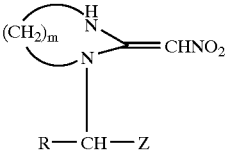
| Compound No. | Z | R | m |
|---|---|---|---|
| 766 | 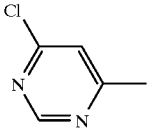 | H | 2 |
| 767 | 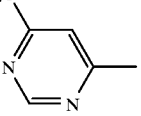 | H | 3 |
| 768 | 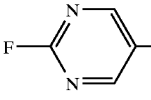 | H | 2 |
| 769 | 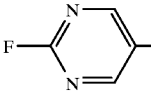 | H | 3 |
| 770 | 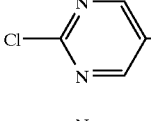 | H | 2 |
| 771 | 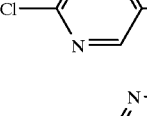 | H | 3 |
| 772 | 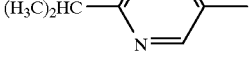 | H | 2 |
| 773 | 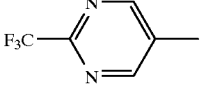 | H | 2 |
| 774 | 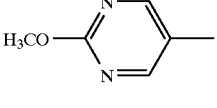 | H | 2 |
| 775 | 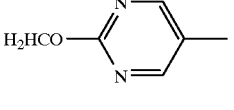 | H | 2 |
| 776 | 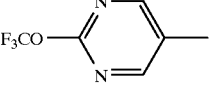 | H | 2 |

TABLE 10-continued
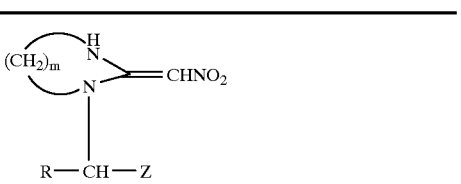
| Compound No. | Z | R | m |
|---|---|---|---|
| 777 | F₃CH₂CO-pyrimidin-5-yl | H | 3 |
| 778 | H₃CS-pyrimidin-5-yl | H | 2 |
| 779 | H₅C₂S-pyrimidin-5-yl | H | 2 |
| 780 | F₂HCS-pyrimidin-5-yl | H | 2 |
| 781 | F₃CS-pyrimidin-5-yl | H | 2 |
| 782 | F₃CH₂CS-pyrimidin-5-yl | H | 2 |
| 783 | O₂N-pyrazin-5-yl | H | 2 |
| 784 | NC-pyrazin-5-yl | H | 3 |
| 785 | Cl-pyrazin-5-yl | H | 2 |
| 786 | F₃C-pyrazin-5-yl | H | 2 |
| 787 | F-pyridazin-6-yl | H | 2 |

TABLE 10-continued
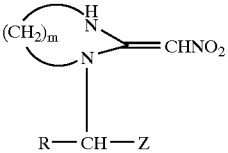
| Compound No. | Z | R | m |
|---|---|---|---|
| 788 | 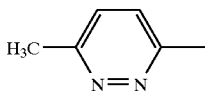 | H | 3 |
| 789 | 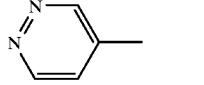 | H | 2 |
| 790 | 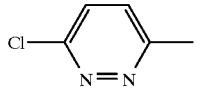 | H | 2 m.p. 172–175° C. |
| 791 | 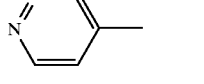 | H | 3 |
| 792 | 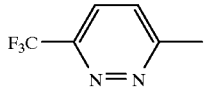 | H | 2 |
| 793 | 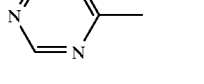 | H | 2 |
| 794 | 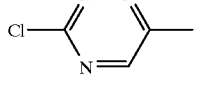 | H | 2 |
| 795 | 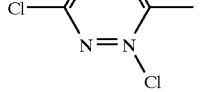 | H | 2 |
| 796 | 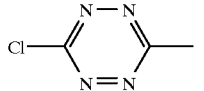 | H | 2 |
| 797 | 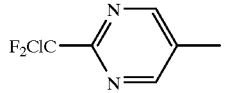 | H | 2 |
| 798 | 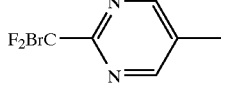 | H | 2 |
Besides table Nos. 5 to 10, there follows the case where X is N—$R^7$: —(table 11)

TABLE 11
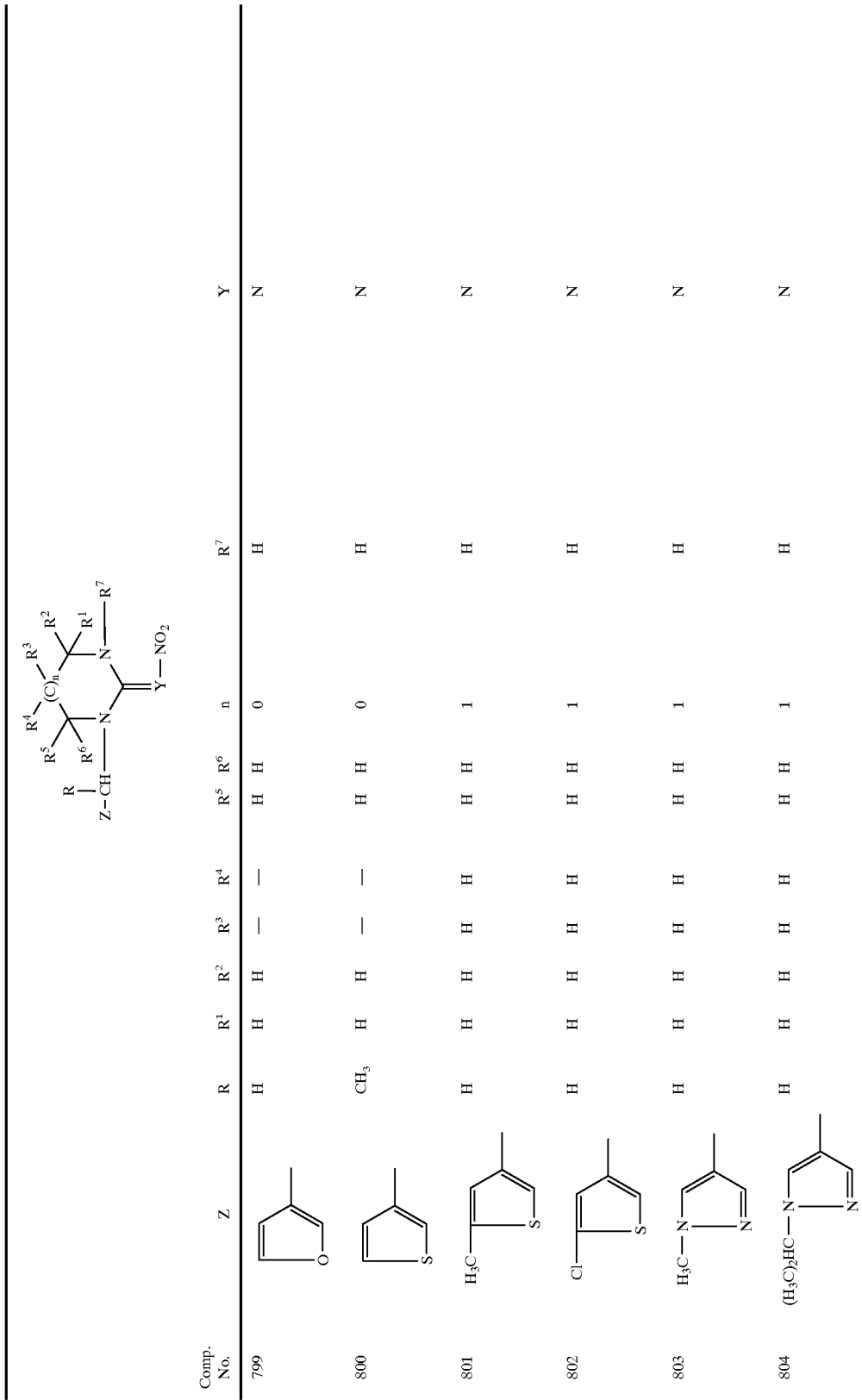
| Comp. No. | Z | R | R¹ | R² | R³ | R⁴ | R⁵ | R⁶ | n | R⁷ | Y |
|---|---|---|---|---|---|---|---|---|---|---|---|
| 799 | 3-methylfuran | H | H | H | — | — | H | H | 0 | H | N |
| 800 | 3-methylthiophene | CH₃ | H | H | — | — | H | H | 0 | H | N |
| 801 | 4-methyl-5-yl thiophene (H₃C-) | H | H | H | H | H | H | H | 1 | H | N |
| 802 | 4-methyl-5-chloro thiophene (Cl-) | H | H | H | H | H | H | H | 1 | H | N |
| 803 | 4-methyl-1-methyl pyrazole (H₃C-N) | H | H | H | H | H | H | H | 1 | H | N |
| 804 | 4-methyl-1-isopropyl pyrazole ((H₃C)₂HC-N) | H | H | H | H | H | H | H | 1 | H | N |

TABLE 11-continued

| Comp. No. | Z | R | R¹ | R² | R³ | R⁴ | R⁵ | R⁶ | n | R⁷ | Y | |
|---|---|---|---|---|---|---|---|---|---|---|---|---|
| 805 | 5-methyl-3-methylisoxazole | H | H | H | — | — | H | H | 0 | H | N | mp. 149–150° C. |
| 806 | 3-chloro-5-methylisoxazole | H | H | H | — | — | H | H | 0 | H | N | |
| 807 | 3-trifluoromethyl-5-methylisoxazole | H | H | H | — | — | H | H | 0 | H | N | |
| 808 | 5-methyloxazole | H | H | H | H | H | H | H | 1 | H | N | |
| 809 | 2-fluoro-5-methyloxazole | H | H | H | — | — | H | H | 0 | H | N | |

TABLE 11-continued
| Comp. No. | Z | R | R¹ | R² | R³ | R⁴ | R⁵ | R⁶ | n | R⁷ | Y | |
|---|---|---|---|---|---|---|---|---|---|---|---|---|
| 810 |  | H | H | H | — | — | H | H | 0 | H | N | |
| 811 | 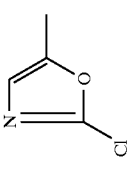 | H | H | H | H | H | H | H | 1 | H | N | |
| 812 | 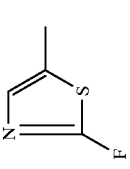 | H | H | H | — | — | H | H | 0 | H | N | |
| 813 | 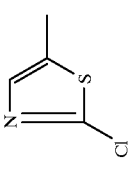 | H | H | H | H | H | H | H | 1 | H | N | mp. 123–128° C. |
| 814 | 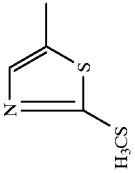 | H | H | H | H | H | H | H | 1 | H | N | |

TABLE 11-continued $$Z-CH(R)-N(R^1R^2)-C(R^3)(C_n)(R^4)(R^5)(R^6)-N(R^7)-C(=Y-NO_2)$$

| Comp. No. | Z | R | $R^1$ | $R^2$ | $R^3$ | $R^4$ | $R^5$ | $R^6$ | n | $R^7$ | Y | |
|---|---|---|---|---|---|---|---|---|---|---|---|---|
| 815 | 2-methyl-thiazol-5-yl (H₃C-) | H | H | H | H | H | H | H | 1 | H | N | |
| 816 | 5-(F₂HCS)-thiazol-2-yl | H | H | H | H | H | H | H | 1 | H | N | |
| 817 | 5-(F₂HCO)-thiazol-2-yl | H | H | H | H | H | H | H | 1 | H | N | |
| 818 | 4-methyl-2-chloro-thiazol-5-yl | H | H | H | — | — | H | H | 0 | H | N | |
| 819 | 5-methyl-1,2,3-thiadiazol-4-yl | H | H | H | H | H | H | H | 1 | H | N | mp. 141–145° C. |

TABLE 11-continued $$\text{Z—CH} \overset{R}{\underset{}{\mid}} \begin{array}{c} R^5 \\ R^6 \end{array} \overset{R^4}{\underset{}{(C)_n}} \overset{R^3}{\underset{}{\mid}} \overset{R^2}{\underset{}{\mid}} \overset{R^1}{\underset{}{\mid}} N \overset{R^7}{\underset{}{\mid}} C \overset{}{=} Y\text{—NO}_2$$

| Comp. No. | Z | R | R¹ | R² | R³ | R⁴ | R⁵ | R⁶ | n | R⁷ | Y |
|---|---|---|---|---|---|---|---|---|---|---|---|
| 820 | 2-methyl-5-fluoro-oxazole | H | H | H | H | H | H | H | 1 | H | N |
| 821 | 5-methyl-3-H₃C-oxadiazole | H | H | H | H | H | H | H | 1 | H | N |
| 822 | 5-methyl-3-F₃C-oxadiazole | H | H | H | H | H | H | H | 1 | H | N |
| 823 | 5-methylpyrimidine | H | H | H | — | — | H | H | 0 | H | N |
| 824 | 5-methylpyrimidine | CH₃ | H | H | — | — | H | H | 0 | H | N |
| 825 | 2-methyl-5-pyrimidine | H | H | H | — | — | H | H | 0 | H | N |

TABLE 11-continued

| Comp. No. | Z | R | R¹ | R² | R³ | R⁴ | R⁵ | R⁶ | n | R⁷ | Y | |
|---|---|---|---|---|---|---|---|---|---|---|---|---|
| 826 | 5-methyl-2-fluoropyrimidine | H | H | H | — | — | H | H | 0 | H | N | |
| 827 | 5-methyl-2-chloropyrimidine | H | H | H | — | — | H | H | 0 | H | N | mp. 181–183° C. |
| 828 | 5-methyl-2-chloropyrimidine | H | H | H | — | — | H | H | 1 | H | N | |
| 829 | 4-methylpyridazine | H | H | H | H | H | H | H | 0 | H | N | |
| 830 | 2-methylpyrazine | H | H | H | — | — | H | H | 0 | H | N | |
| 831 | 5-methyl-2-methylpyrazine | H | H | H | — | — | H | H | 0 | H | N | mp. 142–144° C. |
| 832 | 5-methyl-2-chloropyrazine | H | H | H | — | — | H | H | 0 | H | N | |

TABLE 11-continued $$Z-CH \begin{matrix} R \\ | \\ \end{matrix} \begin{matrix} R^5 \\ R^6 \end{matrix} (C)_n \begin{matrix} R^3 \\ R^4 \end{matrix} \begin{matrix} R^1 \\ R^2 \end{matrix} N-R^7 \\ N=C \\ Y-NO_2$$

| Comp. No. | Z | R | $R^1$ | $R^2$ | $R^3$ | $R^4$ | $R^5$ | $R^6$ | n | $R^7$ | Y | |
|---|---|---|---|---|---|---|---|---|---|---|---|---|
| 833 | 6-chloro-pyridazin-3-yl | H | H | H | — | — | H | H | 0 | H | N | mp. 216–219° C. |
| 834 | 6-trifluoromethyl-pyridazin-3-yl | H | H | H | — | — | H | H | 0 | H | N | |
| 835 | 1-methyl-4-methyl-pyrazolyl | H | H | H | $CH_3$ | $CH_3$ | H | H | 1 | H | CH | mp. 210–213° C. |
| 836 | 2-chloro-5-methyl-thiazol-yl | H | H | H | H | H | H | H | 1 | $CH_3$ | CH | |
| 837 | 3-methyl-isothiazol-5-yl | H | H | H | H | H | H | H | 1 | $C_2H_5$ | CH | |
| 838 | 5-methyl-furan-2-yl | H | H | H | — | — | H | H | 0 | $CH_2$-furyl | CH | |

TABLE 11-continued

Structure:
Z—CH(R)—N(R¹R²)—C(R³)(Cₙ)(R⁴)—N(R⁶R⁵)—... N—C(=Y—NO₂)—N—R⁷

| Comp. No. | Z | R | R¹ | R² | R³ | R⁴ | R⁵ | R⁶ | n | R⁷ | Y | |
|---|---|---|---|---|---|---|---|---|---|---|---|---|
| 839 | 2-methyl-furan-5-yl (H₃C-furan) | H | H | H | — | — | H | H | 0 | CH₂-(furan-2-yl) | CH | |
| 840 | 2-methyl-thiophen-5-yl | H | H | H | — | — | H | H | 0 | CH₂-(thiophen-2-yl) | CH | mp. 154–156° C. |
| 841 | 3-methyl-thiophen-yl | H | H | H | — | — | H | H | 0 | CH₂-(thiophen-3-yl) | CH | glass |
| 842 | 3-methyl-thiophen-yl | H | H | H | H | H | H | H | 1 | CH₂-(thiophen-3-yl) | CH | $n_D^{20}$ 1.5980 |
| 843 | 3-methyl-5-H₃C-isoxazol-yl | H | H | H | — | — | H | H | 0 | CH₂-(1-CH₃-pyrazol-4-yl) | CH | |
| 844 | 3-methyl-5-F₃C-isoxazol-yl | H | H | H | H | H | H | H | 1 | CH₂-(thiadiazol-5-yl) | CH | |

TABLE 11-continued
| Comp. No. | Z | R | R¹ | R² | R³ | R⁴ | R⁵ | R⁶ | n | R⁷ | Y |
|---|---|---|---|---|---|---|---|---|---|---|---|
| 845 | 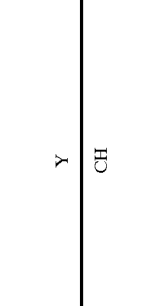 | H | H | H | H | H | H | H | 1 |  | CH |
| 846 | 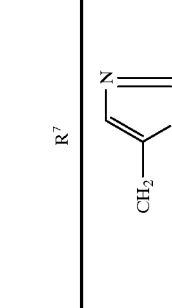 | H | H | H | — | — | H | H | 0 | 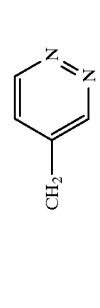 | CH |
| 847 | 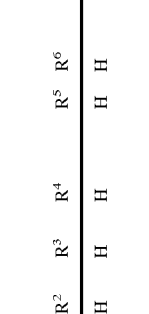 | H | H | H | — | — | H | H | 0 |  | CH |
| 848 | 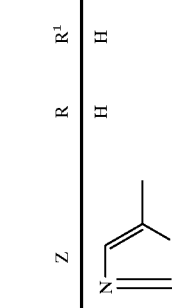 | H | H | H | — | — | H | H | 0 | H | C—COOC₂H₅ mp. 153–155° C. |
| 849 | 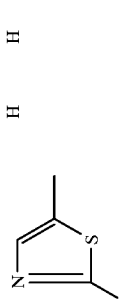 | H | H | H | H | H | H | H | 1 | H | 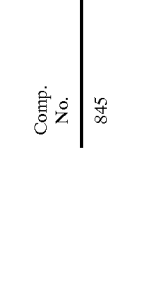 |

TABLE 11-continued

| Comp. No. | Z | R | R¹ | R² | R³ | R⁴ | R⁵ | R⁶ | n | R⁷ | Y |
|---|---|---|---|---|---|---|---|---|---|---|---|
| 850 | 5-methyl-2-fluoro-thiazol-4-yl | H | H | H | H | H | H | H | 1 | H | C—COO-(2-methoxyphenyl) |
| 851 | 3-methyl-1,2,5-thiadiazol-4-yl | H | H | H | — | — | H | H | 1 | H | C—CO(CH₂)₃CH₃ |
| 852 | 4-methyl-thiazol-3-yl | H | H | H | — | — | H | H | 0 | H | C—S-phenyl |
| 853 | 4-methyl-1-ethyl-pyrazol-5-yl | H | H | H | — | — | H | H | 0 | CH₃ | N |
| 854 | 4-methyl-2-chloro-thiazol-5-yl | H | H | H | — | — | H | H | 0 | C(CH₃)₃ | N |
| 855 | 5-methyl-2-chloro-oxazol-4-yl | H | H | H | H | H | H | H | 1 | CH₂SCH₃ | N |

TABLE 11-continued

| Comp. No. | Z | R | R¹ | R² | R³ | R⁴ | R⁵ | R⁶ | n | R⁷ | Y |
|---|---|---|---|---|---|---|---|---|---|---|---|
| 856 | H₃C-[5-methylisoxazol-3-yl] | H | H | H | H | H | H | H | 1 | CH₂CH₂OC₂H₅ | N |
| 857 | CH₃CONH-[5-methylthiazol-2-yl] | H | H | H | — | — | H | H | 0 | CH₂COCH₃ | N |
| 858 | H₃C-[4-methylpyrazol-1-yl] | H | H | H | — | — | H | H | 0 | COCH₃ | N |
| 859 | F₃C-[5-methylthiazol-2-yl] | H | H | H | H | H | H | H | 1 | CHO | N |
| 860 | Cl-[5-methylthiazol-2-yl] | H | H | H | H | H | H | H | 1 | COCH₃ | N |

TABLE 11-continued

| Comp. No. | Z | R | R¹ | R² | R³ | R⁴ | R⁵ | R⁶ | n | R⁷ | Y | |
|---|---|---|---|---|---|---|---|---|---|---|---|---|
| 861 | 2-methyl-1,3-thiazole-5-sulfonyl | H | H | H | — | — | H | H | 0 | CON(C₂H₅)₂ | N | |
| 862 | isothiazol-3-yl | H | H | H | — | — | H | H | 0 | 4-NO₂-C₆H₄-CO- | N | |
| 863 | 3-methylisoxazol-5-yl | H | H | H | — | — | H | H | 0 | COCH₃ | N | |
| 864 | 3-methylisoxazol-5-yl | H | H | H | — | — | H | H | 0 | 2-CH₃-C₆H₄-CO- | N | |
| 865 | 3-methylisothiazol-5-yl | H | H | H | — | — | H | H | 0 | 2,4-Cl₂-C₆H₃-CO- | N | |
| 866 | 5-methylisothiazol-3-yl | H | H | H | — | — | H | H | 0 | 4-Cl-C₆H₄-CH₂CO- | N | mp. 134–136° C. |

TABLE 11-continued $$Z-CH \underset{R}{\overset{R^5}{\underset{R^6}{|}}} \overset{R^4}{\underset{(C)_n}{|}} \overset{R^3}{\underset{R^2}{|}} \overset{R^1}{\underset{N}{|}} \overset{R^7}{\underset{Y-NO_2}{|}}$$

| Comp. No. | Z | R | R¹ | R² | R³ | R⁴ | R⁵ | R⁶ | n | R⁷ | Y | |
|---|---|---|---|---|---|---|---|---|---|---|---|---|
| 867 | 2-chloro-5-methylthiazol-yl | H | H | H | — | — | H | H | 0 | COOC₂H₅ | N | |
| 868 | 2-fluoro-5-methylthiazol-yl | H | H | H | H | H | H | H | 1 | 4-Cl-C₆H₄-C(O)S- | N | |
| 869 | 1-methyl-pyrazol-yl | H | H | H | — | — | H | H | 0 | C₆H₅-C(O)O- | N | |
| 870 | 3-methyl-isoxazol-yl | H | H | H | — | — | H | H | 0 | CH₃SO₂- | N | |
| 871 | 2-NCS-5-methylthiazol-yl | H | H | H | — | — | H | h | 1 | ClCH₂SO₂- | N | |
| 872 | 3-methyl-pyrazin-yl | H | CH₃ | H | — | — | H | H | 0 | H | CH | mp. 156–158° C. |

TABLE 11-continued

[Structure: Z—CH(R)—C(R⁵)(R⁶)—(C)ₙ(R³)(R⁴)—C(R¹)(R²)—N(R⁷)—C(=N—Y—NO₂)—N]

| Comp. No. | Z | R | R¹ | R² | R³ | R⁴ | R⁵ | R⁶ | n | R⁷ | Y |
|---|---|---|---|---|---|---|---|---|---|---|---|
| 873 | 4-methylpyrimidin-... | H | H | H | — | — | H | H | 0 | H | C—COOCH₂—(phenyl) |
| 874 | 5-methyl-2-... pyrazine (H₃C, N, N) | H | H | H | — | — | H | H | 0 | H | C—S—(4-methylphenyl) |
| 875 | 5-methyl-2-chloropyrimidine | H | H | H | — | — | H | H | 0 | CH₃ | N |
| 876 | 3-methyl-6-chloropyridazine | H | H | H | — | — | H | H | 0 | COCH₂OCH₃ | N |
| 877 | 5-methyl-2-... pyrazine (H₃C, N, N) | H | H | H | — | — | H | H | 0 | COCH(Br)—C(CH₃)₃ | N |
| 878 | 4-methylpyridazine | H | H | H | — | — | H | H | 0 | CO—(4-chlorophenyl) | N |

TABLE 11-continued
| Comp. No. | Z | R | R¹ | R² | R³ | R⁴ | R⁵ | R⁶ | n | R⁷ | Y |
|---|---|---|---|---|---|---|---|---|---|---|---|
| 879 | 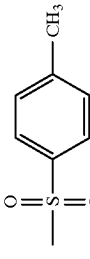 | H | H | H | — | — | H | H | 0 |  | N |
| 880 | 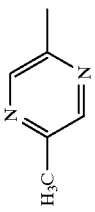 | H | H | H | — | — | H | H | 0 | 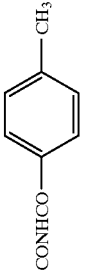 | N |
| 881 | 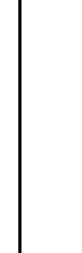 | H | H | H | — | — | H | H | 0 | 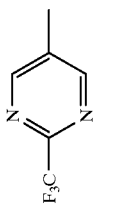 | N |

The case where the formula (I) represents the following formula: —(table 12)

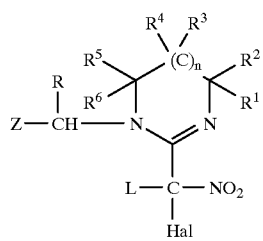

TABLE 12

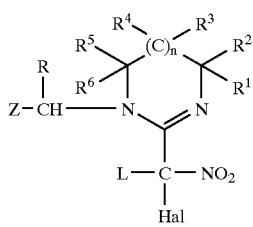

| Comp. No. | Z | R | R¹ | R² | R³ | R⁴ | R⁵ | R⁶ | n | L | Hal | |
|---|---|---|---|---|---|---|---|---|---|---|---|---|
| 882 | 4-pyridyl | H | H | H | — | — | H | H | 0 | Cl | Cl | |
| 883 | 6-chloro-3-pyridyl | H | H | H | — | — | H | H | 0 | Cl | Cl | |
| 884 | 6-chloro-3-pyridyl | H | H | H | — | — | H | H | 0 | Br | Br | mp. 140–143° C. (decomp.) |
| 885 | 6-chloro-3-pyridyl | H | H | H | — | — | H | H | 0 | Cl | Br | |

The case where the formula (I) represents the following formula: —(table 13)

TABLE 13

| Comp. No. | Compounds | |
|---|---|---|
| 886 | 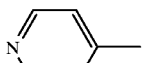 | mp. 170–175° C. (decomp.) |

TABLE 13-continued

| Comp. No. | Compounds |
|---|---|
| 887 | 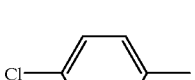 |

Typical examples of synthesizing the intermediate compound of the formula (II) are shown below. Example 36.

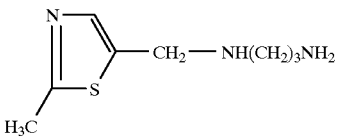

Trimethylenediamine (37 g) was dissolved in 120 ml of acetonitrile, and a solution of 14.8 g of 5-chloromethyl-2-methylthiazole in 30 ml of acetonitrile was added dropwise at 10 to 15° C. After the addition, the mixture was stirred at 30 to 40° C. for a while, and then 8 g of a 50% aqueous solution of sodium hydroxide was added. Subsequently, the volatile materials were removed at a bath temperature of less than 50 ° C. under 5 mmHg. The inorganic materials were removed from the residue by filtration to give 16.7 g of N-(2-methyl-5-thiazolylmethyl) trimethylenediamine (purity about 90%) as a colorless oil.

$n_D^{22}$: 1.5126

Example 37

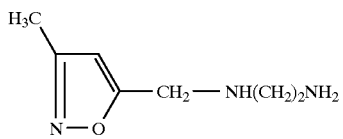

Ethylenediamine (30 g) was dissolved in 120 g of acetonitrile, and a solution of 17.6 g of 5-bromomethyl-3-methylisoxazole in 30 ml of acetonitrile was added dropwise at 5 to 10° C. After the addition, the mixture was stirred for 1 hour with a care taken not to permit the temperature of the reaction system to rise above 20° C. Then, most of the volatile materials were removed under vacuum (less than 2 mmHg) while maintaining the bath temperature at 20° C. Ice water was added to the residue, and the mixture was extracted With dichloromethane. The dichloromethane layer was dehydrated, and dichloromethane was distilled off under reduced pressure to give 10.0 g of N-(3-methyl-5-isoxazolylmethyl)ethylenediamiine (purity about 95%) as a colorless oil.

NMR spectrum (δ in CDCl₃):
 NH, NH₂: 1.47 (ppm)
 —CH₂CH₂—: 2.23
 —CH₃: 2.7
 —CH₂—: 5.8
 Hetero-H: 5.9

Example 38

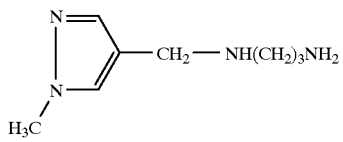

At room temperature 11 g of 1-methyl-4-pyrazole carbaldehyde was slowly added to 37 g of ethylenediamine in 150 ml of dry acetonitrile. Molecular sieves 4A (a product of Wako Pure Chemicals, Co.) were added as a dehydrating agent to the solution. The mixture was stirred at room temperature for 2 hours, and filtered. Acetonitrile was distilled off under reduced pressure from the filtrate. To the residue was added 100 ml of ethanol, and then 4 g of sodium borohydride was added little by little at room temperature. The mixture was then stirred at room temperature for 2 hours, and ethanol was distilled off under reduced pressure. Water was added to the residue, and the mixture was extracted with dichloromethane. The solvent was distilled off from the: dichloromethane layer, and the residue was vacuum-distilled to give 10 g of N-(1-methyl-4-pyrazolylmethyl)trimethylenediamine as a colorless oil.

bp.: 120–125° C./0.8 mmHg

Example 39

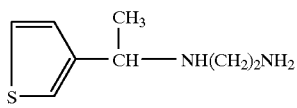

A solution composed of 12.6 g of 3-acetylthiophene, 30 g of ethylenediamine and 150 ml of benzene was refluxed with stirring while removing water as an azeotrope. When formation of water was no longer observed, benzene was distilled off under reduced pressure. Ethanol (100 ml) was added to the residue, and subsequently, 4 g of sodium borohydride was added little by little. The mixture was then stirred at 40° C. for 2 hours. Ethanol was distilled off under reduced pressure. A small amount of the inorganic matter was removed from the residue. Subsequent vacuum distillation have 8.2 g of N-[1-(3-thienyl)ethyl]ethylenediamine.

bp.: 102–105° C./3.5 mmHg

Novel compounds of the formula (II) obtained by the same methods as described in Examples 36 to 39 are shown below.

TABLE 14

$$H_2N-(CH_2)_m-NH-\underset{R}{\overset{|}{CH}}-Z$$

| Z | R | m | |
|---|---|---|---|
| (3-thienyl) | H | 3 | |
| (2-pyrrolyl, NH) | H | 2 | $n_D^{20}$ 1.5523 |
| (2-methyl-pyrrolyl, NH) | H | 3 | $n_D^{20}$ 1.5495 |
| (N-methyl-pyrrolyl) | H | 3 | |
| (5-methyl-2-thienyl) | H | 2 | bp 108~110° C./ 4 mmHg |
| (5-bromo-2-thienyl) | H | 3 | bp 135~140° C./ 0.5 mmHg |
| (5-cyano-2-furyl) | H | 2 | |
| (5-trifluoromethylthio-2-thienyl) | H | 2 | $n_D^{20}$ 1.4775 |
| (5-trifluoromethylthio-2-thienyl) | H | 3 | $n_D^{23}$ 1.4752 |

TABLE 14-continued $$H_2N-(CH_2)_m-NH-\underset{\underset{R}{|}}{CH}-Z$$

| Z | R | m | |
|---|---|---|---|
| 3,5-dimethylisoxazol-4-yl (O-N, H3C, CH3) | H | 3 | |
| 5-methylisoxazol-3-yl | H | 3 | |
| 4-methylisoxazol-3-yl | H | 3 | |
| 3,5-dimethylisoxazol-4-yl (H3C, N-O, CH3) | H | 3 | |
| 3-trifluoromethyl-5-methylisoxazol-4-yl (F3C, N-O, CH3) | H | 3 | $n_D^{20}$ 1.4683 |
| 3-chloro-5-methylisoxazol-4-yl (Cl, N-O, CH3) | H | 2 | |
| 5-methylisothiazol-3-yl (N-S, CH3) | H | 3 | |
| 5-methyl-1H-pyrazol-3-yl (N-NH, CH3) | H | 2 | $n_D^{20}$ 1.5335 |
| 5-methyl-1H-pyrazol-3-yl | H | 3 | $n_D^{20}$ 1.5230 |
| 4-methyl-1H-pyrazol-3-yl (HN-N, CH3) | H | 2 | |
| 4-methyl-1H-pyrazol-3-yl | H | 3 | |
| 1,4-dimethylpyrazol-3-yl (H3C-N, CH3) | H | 2 | bp 125~127° C./ 1 mmHg |
| 1,4-dimethylpyrazol-3-yl | —CH3 | 2 | bp 133~135° C./ 1.2 mmHg |
| 1-ethyl-4-methylpyrazol-3-yl (H3C2-N, CH3) | H | 3 | $n_D^{20}$ 1.5251 |
| 1-isopropyl-4-methylpyrazol-3-yl (iso-H7C3-N, CH3) | H | 3 | |
| 1-allyl-4-methylpyrazol-3-yl (H2C=HCH2C-N, CH3) | H | 3 | $n_D^{20}$ 1.5085 |
| 1-tert-butyl-4-methylpyrazol-3-yl (tert-H9C4-N, CH3) | H | 2 | $n_D^{20}$ 1.5045 |
| 1-(2,2,2-trifluoroethyl)-5-methylpyrazol-3-yl (N-N, CH3, CH2CF3) | H | 2 | $n_D^{20}$ 1.4651 |
| 3,5-dimethylpyrazol-1-yl (H3C-N-N-CH3) | H | 2 | |
| 5-chloro-1,3-dimethylpyrazol-4-yl (Cl, H3C-N-N, CH3) | H | 2 | $n_D^{20}$ 1.4940 |
| 5-chloro-1,3-dimethylpyrazol-4-yl | H | 3 | $n_D^{20}$ 1.4904 |
| 1,3,4,5-tetramethylpyrazol-... (H3C-N-N-CH3, CH3, CH3) | H | 3 | |
| 5-methyloxazol-2-yl | H | 2 | $n_D^{20}$ 1.5003 |

TABLE 14-continued $$H_2N-(CH_2)_m-NH-\underset{R}{\overset{|}{CH}}-Z$$

| Z | R | m | |
|---|---|---|---|
| oxazol-2-yl (5-methyl) | H | 3 | |
| 4,5-dimethyl-oxazol-2-yl | H | 2 | $n_D^{27}$ 1.5160 |
| 4,5-dimethyl-oxazol-2-yl | H | 3 | $n_D^{27}$ 1.5130 |
| 4-methyl-thiazol-2-yl | H | 2 | $n_D^{20}$ 1.5722 |
| 5-methyl-thiazol-2-yl | H | 2 | |
| 5-methyl-thiazol-2-yl | H | 3 | |
| 2-methyl-5-methyl-thiazol | H | 2 | $n_D^{24}$ 1.5205 |
| 2-chloro-4-methyl-thiazol | H | 2 | $n_D^{24}$ 1.5691 |
| 2-chloro-5-methyl-thiazol | H | 3 | |
| 2-trifluoromethyl-5-methyl-thiazol | H | 2 | |
| 2-bromo-5-methyl-thiazol | H | 2 | |
| 2,4-dichloro-5-methyl-thiazol | H | 2 | $n_D^{20}$ 1.5788 |
| 4-methyl-imidazol-2-yl (NH) | H | 3 | |
| 1,2-dimethyl-imidazol | H | 2 | |
| 5-methyl-1H-1,2,4-triazol | H | 2 | |
| 1,3-dimethyl-1,2,4-triazol | H | 2 | |
| 4-methyl-1,2,3-thiadiazol | H | 2 | $n_D^{20}$ 1.5457 |
| 5-methyl-1,2,3-thiadiazol | H | 2 | |
| 5-methyl-1,2,3-thiadiazol | H | 3 | |
| 3,5-dimethyl-1,2,4-oxadiazol | H | 2 | |
| 2-methyl-1,3-dioxolan | H | 3 | bp 90° C./25 mmHg |
| 2,2-dimethyl-4-methyl-1,3-dioxolan | H | 2 | $n_D^{17}$ 1.4715 |
| 2-methyl-5-methyl-oxazoline | H | 2 | |

TABLE 14-continued $$H_2N-(CH_2)_m-NH-\overset{\overset{R}{|}}{C}H-Z$$

| Z | R | m |
|---|---|---|
| 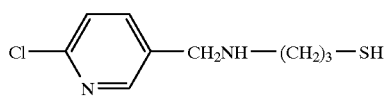 | H | 2 |

Example 40

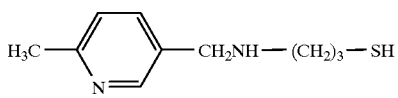

A solution composed of 6-chloronicotinaldehyde (14.2 g), 2-aminoethanethiol (7.7 g) and benzene (80 ml) was heated with stirring for 5 hours while removing water as an azeotrope. After the reaction, benzene was distilled off under reduced pressure, and further volatile materials were removed at 1 mmHg and 70° C. to give 2-(2-chloro-5-pyridyl)thiazolidine (18 g) as a residue. Ten grams of 2-(2-chloro-5-pyridyl)thiazolidine was dissolved in 100 ml of ethanol, and sodium borohydride was added. With stirring, the mixture was gradually heated and thereafter re-fluxed for 1 hour. Ethanol was distilled off under reduced pressure, and chloroform was added to the residue. Insoluble materials were separated by filtration and the chloroform layer was washed with water and dehydrated. Chloroform was distilled off under reduced pressure to give the desired N-(2-chloro-5-pyridylmethyl)2-aminoethanethiol (8.3 g).

$n_D^{24}$: 1.5917.

Example 41

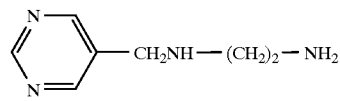

A solution composed of 6-methylnicotinaldehyde (12.1 g, 3-aminopropanethiol (9.1 g) and benzene (120 ml) was refluxed for 5 hours with stirring while removing water as an azeotrope. After the reaction, benzene was distilled off under reduced pressure, and volatile materials were removed at 1 mmHg and 70° C. As a residue, 3-pyridyltetrahydrothiazine (16.5 g) was obtained. Then, 3-pyridyltetrahydrothiazine (10 g) was dissolved in 100 ml of ethanol, and sodium borohydride was added. The mixture was gradually heated with stirring, and subsequently refluxed for 1 hour. Ethanol was distilled off under reduced-pressure. Chloroform was added to the residue, and insoluble materials were separated by filtration. The chloroform layer was washed with water and dehydrated. On distilling off chloroform under reduced pressure, the desired N-(3-pyridyl)3-aminopropanethiol (6.2 g) was obtained.

$n_D^{20}$: 1.5733

Compund No. II of the following formula was also prepared by the same method as in Examples 40 and 41.

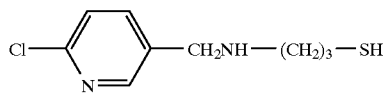

N-(2-chloro-5-pyridylmethyl)3-aminopropanethiol ($n_D^{22}$: 1.5890)

(No. II-4)

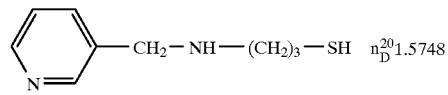

(No. II-5)

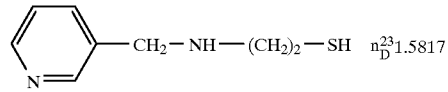

Example 42

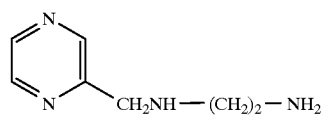

Ethylenediamine (60 g) was dissolved in benzene (200 ml), and 5-formylpyrimidine (21.6 g) was added at room temperature. Subsequently, the mixture was heated, and refluxed for 3 hours while removing water as an azeotrope. After the reaction, benzene and the excess of ethylenediamine were distilled off under reduced pressure. The residue was dissolved in ethanol (200 ml). Sodium borohydride (8.4 g) was added portionwise to this solution at room temperature, and subsequently the mixture was stirred at room temperature for 5 hours. Ethanol was distilled off under reduced pressure. Dichloromethane (100 ml) was added to the residue, and a dichloromethane-soluble portion was separated. Dichloromethane was distilled off from the dichloromethane layer under reduced pressure to give N-(5-pyrimidinylmethyl)ethylenediamine (25.8 g) as a colorless oil. $n_D^{25}$=1.5532.

Example 43

Ethylenediamine (30 g) was dissolved in acetonitrile (200 ml), and pyrazinylmethyl chloride (12.9 g) was added dropwise to this solution at 5 to 10° C. After addition, the mixture was stirred at room temperature for 1 hour. Then, a 50% aqueous solution of sodium hydroxide (8 g) was added, and thereafter, volatile materials were removed at a bath temperature of 60° C. under 5 mmHg. The inorganic salt was then removed by filtration. Thus, N-(pyrazinylmethyl) ethylenediamine (14.1 g) was obtained as a colorless oil. $n_D^{20}$=1.5359.

Example 44

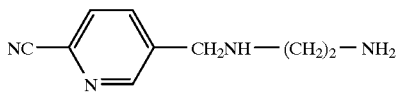

A solution of 2-cyano-5-pyridylmethyl chloride (4.6 g) in acetonitrile (20 ml) was added dropwise to a solution of ethylenediamine (9 g) in acetonitrile (50 ml) at 5 to 10° C. After the addition, the mixture was stirred at room temperature for 3 hours. Acetonitrile and the excess of ethylenediamine were distilled off under reduced pressure from the reaction mixture. Dichloromethane was added to the residue, and a portion of it soluble in dichloromethane was separated. Dichloromethane was distilled off under reduced pressure. Volatile materials were removed at 50° C. and 1 mmHg to give N-(2-cyano-5-pyridylmethyl) ethylenediamine (4.5 g) as a colorless oil.

$n_D^{20} = 1.5718$

Example 45

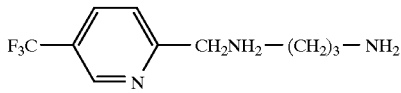

5-Trifluoromethylpicoline aldehyde (3.5 g) was added dropwise at room temperature to a solution of trimethylenediamine (7.4 g) in benzene (70 ml). After the addition, the mixture was gradually heated with stirring, and then while separating water as an azeotrope, refluxed for 2 hours. Benzene was distilled off under reduced pressure, and then the residue was dissolved in ethanol (100 ml). With stirring at 10 to 15° C., sodium borohydride (0.9 g) was added little by little. The mixture was then stirred at room temperature for 2 hours. Ethanol was distilled off at less than 30° C. Dichloromethane was added to the residue, and a portion of it soluble in dichloromethane was separated. Dichloromethane was distilled off under reduced pressure, and volatile materials were removed at 1 mmHg and less than 60° C. to give N-(5-trifluoromethyl-2-pyridylmethyl) trimethylenediamine (3.5 g) as a colorless oil.

$n_D^{20} 1.465$

Example 46

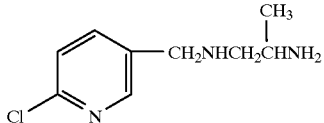

A solution of 8.1 g of 2-chloro-5-chloromethylpyridine in 30 ml of acetonitrile was added dropwise to a mixture of 14.8 g of 1,2-diaminopropane, 5 g of 40% sodium hydroxide solution, and 100 ml of acetonitrile at 0° C. during 2 hours with vigorous stirring. After stirring for a short time at room temperature, the acetonitrile, water and excess 1,2-diaminopropane were removed under reduced pressure. Inorganic salt was filtered off with suction from the residue. The filtrate was the desired product, 2-amino-1-(2-chloro-5-pyridylmethylamino)propane (9.3 g).

$n_D^{17} 1.5450$

In the same way as in Example 46, the following compounds were produced.

N-methyl-N'-3-pyridylmethylethylenediamine
bp. 140° C./2.5 mmHg 2-amino-2-methyl-1-(3-pyridylmethylamino) propane
bp. 115° C./1.5 mmHg 2-aminomethyl-2-methyl-1-(1-methyl-4-pyrazolylmethyl)propane
$n_D^{25} 1.5109$ Example 47

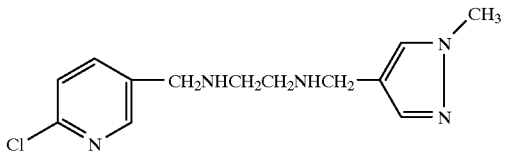

A solution of 18.6 g of N-(2-chloro-5-pyridylmethyl) ethylenediamine, 11 g of 1-methylpyrazole-4-carbaldehyde in 150 ml of benzene was stirred on warm water bath. After a short time, water was separated from the solution and the Schiff base was obtained. The benzene and water were then removed under reduced pressure and 100 ml of ethanol was added to the residue. To the solution 3.8 g of sodiumborohydride was added portionwise at room temperature and the mixture was stirred for 1 day. After removing the ethanol under reduced pressure, the residue was dissolved in dichloromethane and washed with water. The treatment of dichloromethane solution the usual way gave the desired intermediate, N-(2-chloro-5-pyridylmethyl)-N'-(1-methyl-4-pyrazolylmethyl)ethylenediamine as a viscous oil. The yield was 23.5 g.

$n_D^{20} 1.5655$

In the same way as in Example 47, the following compounds, for example, were produced.

N-(3-pyridylmethyl)-N'-(2-chloro-5-pyridylmethyl) ethylenediamine
$n_D^{20} 1.5846$ N-(3-methyl-5-isoxazolylmethyl)-N'-(1-methyl-4-pyrazolylmethyl) trimethylenediamine
$n_D^{20} 1.5224$ Example 48

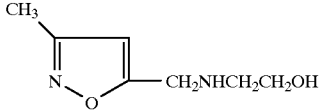

A solution of 7 g of 5-bromomethyl-3-methylisoxazole in 20 ml of acetonitrile was added dropwise to a solution of 12.2 g of 2-aminoethanol in 100 ml of acetonitrile below 10° C. After stirring for a while at room temperature, the acetonitrile and excess-2-aminoethanol were removed under reduced pressure. Chloroform was added to the residue, and it was washed with a small quantity of water. The treatment of the chloroform solution the usual way gave the desired 2-(2-methyl-5-isoxazolylmethylamino)ethanol. The yield was 4.4 g.

$n_D^{20} 1.5130$

In the same way as in Example 48, the following compounds, for example, were produced.

3-(2-chloro-5-pyridylmethylamino)propanol
$n_D^{27} 1.539$

N-(4-pyridylmethyl) ethanolamine
bp. 148–150° C./3 mmHg

Example 49

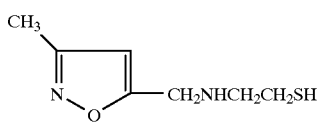

To a solution of 15.6 g of 2-(3-methyl-5-isoxazolylmethylamino)ethanol in 100 ml of chloroform was added catalytic pyridine and then 15 g of thionylchloride at room temperature. After the addition, the mixture was refluxed for 30 minutes, and the evaporation of volatile material in vaccum yielded crude chlorinated compound as its hydrochloride.

mp. 136–139° C.

An ethanolic potassium hydrosulfide solution was prepared by saturating hydrogen sulfide gas in a solution of 13.4 g of potassium hydroxide in 120 ml of ethanol. To the resulting solution was added portionwise the above chloride hydrochloride at 25–30° C. with stirring. The reaction mixture was warmed up slowly, then was stirred for 2 hours at 60° C. After cooling to room temperature, inorganic salt was quickly filtered off with suction. The solvent was removed from the filtrate under reduced pressure to give 2-(3-methyl-5-isoxazolylmethylamino)ethanethiol (12.9 g) as an oil.

$n_D^{25} 1.5490$

In the same way as in Example 49, the following compound, for example, was produced.

2-(2-methyl-5-pyrazinylamino)ethylmercaptan $n_D^{28} 1.5581$

Example 50

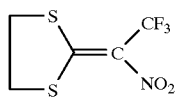

2.72 g of ethylenetrithiocarbonate and 2.52 g of dimethylsulfate were mixed and heated to 100° C. for 1 hour. 10 ml of acetic acid and 2.029 of triethylamine were added to the resulting 2-methylmercapto-1,3-dithiolaniummethylsulfate. 2.69 of 2,2,2-trifluoronitroethane was then added dropwise to the mixture with cooling in an ice bath. The whole mixture was heated slowly to 100° C. and maintained at this temperature for 4 hours. After standing overnight at room temperature, 100 ml of water was added to the reaction mixture. The precipitated crystal was filtered and recrystallized from ethanol to give 1-nitro-2,2-ethylenedimercapto-1-trifluoromethylethylene. The yield was 4.35 g.

mp. 130–133° C.

Example 51

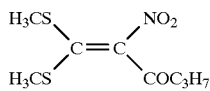

To a solution of 13.1 g of 1-nitro-2-pentanone in 200 ml of dimethylsulfoxide was added dropwise 44 g of 20% sodium hydroxide solution at 10–20° C. 12 g of carbon disulfide was then added dropwise to the solution at 10° C. and the mixture was stirred for 2 hours at 0–10° C. 57 g of methyliodide was dropped into the mixture with ice cooling and the reaction mixture was allowed to stand overnight at room temperature. This was then poured into ice water and the organic layer was extracted with dichloromethane. The extract was washed with water a few times, and after removing the solvent the residue was purified by chromatography on a silicagel column to give desired 1-butyroyl-1-nitro-2,2-bis (methylthio)ethylene. The yield is 3.0 g.

$n_D^{22} 1.5880$

In the same way as in Example 51, the following compound, for example, was produced.

1-benzenesulfonyl-1-nitro-2,2-bis(methylthio) ethylene $n_D^{20} 1.5868$

Example 52

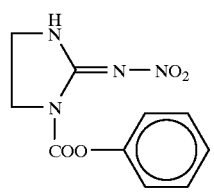

2.5 g of sodium hydride 60% in oil was added in small portions to a solution of 3.9 g of 2-nitroiminoimidazolidine in dry dimethylformamide. After the addition, the mixture was stirred until the generation of hydrogen gas ceased. The mixture was cooled at −5° C. and 4.7 g of phenyl chloroformate was added dropwise below 0° C. After stirring for 1 hour at room temperature, the reaction mixture was poured into ice water, adjusted to pH 7, and extracted with dichloromethane. The white crystals which remained after removing the dichloromethane, and washing with ether were 1-(phenoxycarbonyl)-2-nitroiminoimidazolidine and weighed 5.1 g.

mp. 171–175° C.

In the same way as in Example 52, the following compounds, for example, were produced.

1-(2-methyl-5-nitrobenzenesulfonyl)-2-(nitroimino) imidazolidine mp. 193–197° C.

1-(2,4-dichlorobenzoyl)-2-(nitroimino)imidazolidine mp. 184–186° C.

Example 53

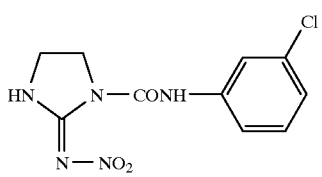

A solution of 3.9 g of 2-nitroiminoimidazolidine and 4.6 g of 3-chlorophenylisocyanate in 80 ml of dry acetonitrile was refluxed for 3 hours. After cooling to room temperature, the precipitated crystals were filtered, and washed with ether to give desired 1-(3-chlorophenylcarbamoyl)-2-nitroiminoimidazolidine. The yield was 4.7 g.

mp. 214–216° C.

Use Example

Comparative compound A-1:

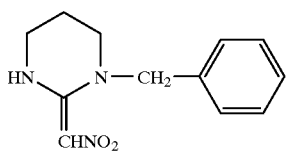

(Compound described in West German OLS No. 2,514, 402)

Comparative compound A-2:

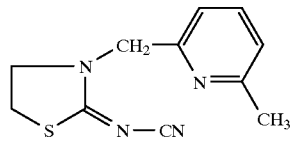

(described in Japanese Laid-Open Patent Publication NO. 196877/1984))

Comparative compound A- 3:

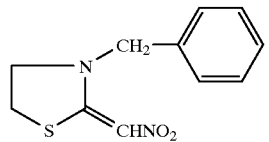

(described in the same patent document as above)

Comparative Compound A-4:

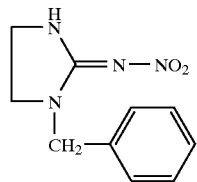

(Compound described in Can. J. Chem., vol. 38, pages 1787–1796)

Example 54

Test on *Nephotettix cincticeps* having resistance to organophosphorus agents:

Preparation of a test chemical
Solvent: 3 parts by weight of xylene
Emulsifier: 1 part by weight of polyoxyethylene alkyl phenyl ether To form a suitable preparation, 1 part by weight of the active compound was mixed with the aforesaid amount of the solvent containing the aforesaid amount of the emulsifier. The mixture was diluted with water to a predetermined concentration.

Testing method

Onto rice plants, about 10 cm tall, planted in pots each having a diameter of 12 cm was sprayed 10 ml per pot of the water-dilution of each active compound in a predetermined concentration prepared as above. The sprayed chemical was dried, and a wire net having a diameter of 7 cm and a height of 14 cm was put over each pot, and 30 female imagoes of *Nerhotettix cincticeps* showing resistance to organophosphorus agents were released into the net. The pots were each placed in a constant temperature chamber and the number of dead insects was examined 2 days later, and the kill ratio was calculated.

As the result, for instance, Compound Nos. 1, 2, 3, 4, 5, 6, 6, 9, 10, 11, 13, 14, 15, 16, 17, 19, 20, 22, 26, 27, 31, 32, 33, 34, 35, 36, 39, 65, 66, 75, 76, 105, 164, 290, 304, 323, 336, 340, 396, 409, 431, 444, 453, 518, 556, 612, 623, 624, 705, 706, 755, 762, 813, 827, 831, 884 showed 100% kill at 8 ppm A.I.

On the other hand, as comparison,
A-1 showed 65% kill at 40 ppm A.I.,
A-2 40% kill at 200 ppm A.I. and
0% kill at 40 ppm A.I.,
A-3 0% kill at 200 ppm A.I., and
A-4 30% kill at 200 ppm A.I Example 55

Test on planthoppers:

Testing method

A water dilution in a predetermined concentration of the active compound prepared as in Example 54 was sprayed onto rice plants, about 10 cm tall, grown in pots with a diameter of 12 cm in an amount of 10 ml per pot. The sprayed chemical was dried, and a wire net, 7 cm in diameter and 14 cm tall, was put over each of the pots. Thirty female imagoes of *Nilaparvata lugens* Stal of a strain which showed resistance to oraanophosphorus chemicals were released into the net. The pots were left to stand in a constant temperature chamber and the number of dead insects was examined two days later. The kill ratio was then calculated.

In the same way as above, the kill ratio was calculated on *Sogatella furcifera* Horvath and organophosphorus-resistant *Laodelphax striatellus* Fallen.

As the result, for instance, Compound Nos. 1, 2, 3, 4, 5, 6, 7, 8, 9, 10, 11, 12, 13, 14, 15, 16, 17, 18, 19, 20, 22, 29, 35, 37, 39, 43, 65, 70, 75, 79, 146, 164, 230, 303, 308, 324, 331, 350, 396, 409, 424, 453, 518, 529, 550, 556, 579, 612, 623, 624, 649, 701, 705, 706, 755, 756, 758, 848 showed 100% kill at 40 ppm A.I. against each planthopper.

On the other hand, as comparison, A-1 showed, at 40 ppm A.I., 50% kill against *N. lugens,* 40% kill against *S. furcifera* and *L. striatellus,* A-2 at 200 ppm A.I. 30% kill against *N. lugens,* 20% kill against *L. striatellus* and 50% kill against *S. furcifera,* and at 40 ppm A.I. 0% kill against each planthopper, A-3 at 200 ppm A.I. 0% kill against each planthopper, and A-4 at 200 ppm A.I. 100% kill ratio against *N. lugens,* 0% kill against *L. striatellus* and *S. furcifera.*

Example 56

Test on *Myzus persicas* (green peach aphids) having resistance to organophosphorus chemicals and carbamate chemicals:

Testing method

Green peach aphids which had been bred and had resistance to organophosphorus chemicals and carbamate chemicals were inoculated on eggplant seedlings (black elongate eggplants), about 20 cm tall, grown in unglazed pots having a diameter of 15 cm (about 200 aphids per seedling). One day after the inoculation, a water dilution of each active compound at a predetermined concentration prepared as in Example 54 was sprayed in a sufficient amount onto the plants using a spray gun. After the spraying, the pets were left to stand in a greenhouse at 28° C. Twenty-four hours after the spraying, the kill ratio was calculated. For each compound, the test was carried out through two replicates.

As the results, for instance, compound Nos. 1, 2, 3, 4, 5, 6, 7, 8, 9, 10, 11, 12, 13, 14, 15, 16, 17, 18, 19, 20, 21, 22, 24, 25, 26, 27, 28, 29, 30, 31, 32, 33, 35, 71, 74, 75, 98, 105, 164, 230, 231, 373, 396, 409, 518, 529, 550, 556, 579, 612, 623, 624, 649, 705, 706, 755 756, 758, 763, 831 showed 100% kill at 200 ppm A.I.

On the other hand, A-1 showed 80% kill at 1000 ppm A.I. and 30% kill at 200 ppm A.I., A-3 60% kill at 1000 ppm A.I.

and 0% kill at 200 ppm A.I., and A-4 60% kill at 1000 ppm A.I., 0% kill at 200 ppm A.I..

Examples 54, 55 and 56 are typical examples of insecticidal uses, and the compounds of this invention exemplified herein are also typical examples. It should be understood that the present invention is not to be limited to them alone.

We claim:

1. A compound of the formula:

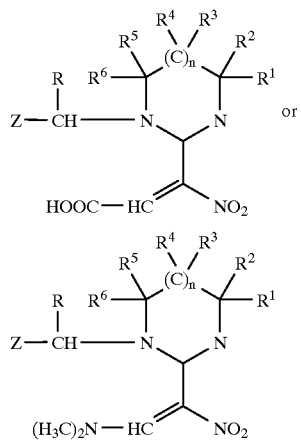

in which n represents 0 or 1;

$R^1$, $R^2$, $R^5$ and $R^6$ independently represent hydrogen or $C_{1-4}$-alkyl;

$R^3$ and $R^4$ independently represent hydrogen, hydroxy or $C_{1-4}$-alkyl;

R represents hydrogen; and

Z represents a 5-membered or 6-membered heterocylic radical, which contains one to three hetero atoms selected from the group consisting of oxygen, sulfur and nitrogen, at least one of said hetero atoms being nitrogen, and said heterocyclic radical being optionally substituted by at least one substituent selected from the group consisting of fluorine; chlorine; bromine; alaly having 1 to 4 carbon atoms which is optionally substituted by fluorine and/or chlorine; nitro; cyano; allylsulfinyl having 1 to 4 carbon atoms; alkylsulfonyl having 1 to 4 carbon atoms; alkoxy having 1 to 4 carbon atoms which is optionally substituted by fluorine and/or chlorine; alkylthio having 1 to 4 carbon atoms which is optionally substituted by fluorine and/or chlorine; alkenyl having 2 or 3 carbon atoms which is optionally substituted by chlorine; acetamido which is optionally substituted by fluorine and/or chlorine; alkoxycarbonyl having 1 to 4 carbon atoms in the alkoxy part; thiocyanato; allynyl having 2 to 4 carbon atoms; amino; methylamino; dimethylamino; acetyl; formyl; carboxyl; hydroxyl; mercapto; cycloalkyl having 3 to 7 carbon atoms; oxo; thioxo; alkenylthio which is optionally substituted by fluorine, chlorine and/or bromine; alkoxyalkyl groups having 2 to 4 carbon atoms in total; alkylaminocarbonyl groups having 1 or 2 carbon atoms in the alkyl part; dialkylaminocarbonyl having 1 or 2 carbon atoms in each alkyl part; phenyl; phenoxy; and benzyl.

2. A compound according to claim 1, which has the formula:

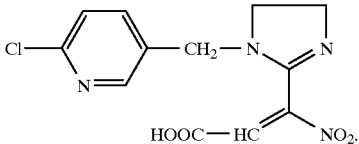

3. A compound according to claim 1, which has the formula:

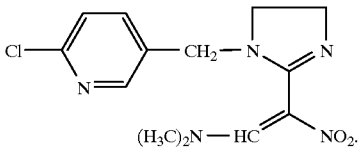

* * * * *